(12) United States Patent
Distelhorst

(10) Patent No.: US 12,138,261 B2
(45) Date of Patent: *Nov. 12, 2024

(54) INHIBITORS OF BCL-2

(71) Applicant: CASE WESTERN RESERVE UNIVERSITY, Cleveland, OH (US)

(72) Inventor: Clark Distelhorst, Cleveland, OH (US)

(73) Assignee: CASE WESTERN RESERVE UNIVERSITY, Cleveland, OH (US)

(*) Notice: Subject to any disclaimer, the term of this patent is extended or adjusted under 35 U.S.C. 154(b) by 144 days.

This patent is subject to a terminal disclaimer.

(21) Appl. No.: 17/583,602

(22) Filed: Jan. 25, 2022

(65) Prior Publication Data

US 2022/0143135 A1 May 12, 2022

Related U.S. Application Data

(63) Continuation of application No. 15/425,865, filed on Feb. 6, 2017, now Pat. No. 11,229,641.

(60) Provisional application No. 62/291,915, filed on Feb. 5, 2016.

(51) Int. Cl.
| | | |
|---|---|---|
| *A61K 31/495* | (2006.01) | |
| *A61K 31/421* | (2006.01) | |
| *A61K 31/44* | (2006.01) | |
| *A61K 31/496* | (2006.01) | |
| *A61K 31/5377* | (2006.01) | |
| *A61K 38/17* | (2006.01) | |
| *A61K 45/06* | (2006.01) | |

(52) U.S. Cl.
CPC .......... *A61K 31/495* (2013.01); *A61K 31/421* (2013.01); *A61K 31/44* (2013.01); *A61K 31/496* (2013.01); *A61K 31/5377* (2013.01); *A61K 38/17* (2013.01); *A61K 45/06* (2013.01)

(58) Field of Classification Search
CPC .................................................. A61K 31/495
See application file for complete search history.

(56) References Cited

U.S. PATENT DOCUMENTS 5,595,756 A * 1/1997 Bally ................... A61K 9/1272
264/4.1
11,229,641 B2 * 1/2022 Distelhorst ............ A61K 45/06

OTHER PUBLICATIONS

Arber et al. (2016, Blood 127:2391-2405) (Year: 2016).*
Swerdlow et al. (2016, Blood 127:2375-2390) (Year: 2016).*
Gura T (Science, 1997, 278(5340) (Year: 1997).*
Freshney (Culture of Animal Cells, a Manual of Basic Technique, Alan R. Liss, Inc., 1983 (Year: 1983).*
Dermer (Bio/Technology, 1994, 12:320) (Year: 1994).*
Zips et al. (2005, In Vivo 19:1-8) (Year: 2005).*
Nature Biotechnology 31:85 (Year: 2013).*
Jain RK (Scientific American, Jul. 1994,58-65) (Year: 1994).*
Sporn et al. (Chemoprevention of Cancer, Carcinogenesis, vol. 21 (2000), 525-530) (Year: 2000).*
Auerbach et al. (Cancer and Metastasis Reviews, 2000, 19: 167-172) (Year: 2000).*
Rong et al. (Molecular Cell. 2008; 31:255-265) (Year: 2008).*
Kirkin et al. (Biochimica et Biophysica Acta. 2004; 1644:229-249). (Year: 2004).*
Dewson et al. (Cell Health and Cytoskeleton. 2010; 2: 9-22) (Year: 2010).*
Baig, S., et al., (Potential of Apoptotic Pathway-Targeted Cancer Therapeutic Research: Where Do We Stand?, Cell Death Dis 7, e2058 (2016). https://doi.org/10.1038/cddis.2015.275) (Year: 2016).*
Hait (Nature Reviews/Drug Discovery, 2010, 9, pp. 253-254) (Year: 2010).*
Gravanis et al. (Chin Clin Oncol, 2014, 3, pp. 1-5). (Year: 2014).*
Beans (PNAS 2018; 115(50): 12539-12543) (Year: 2018).*
Heppner et al. (Cancer Metastasis Review 2:5-23; 1983) (Year: 1983).*
Bowie et al. (Science, 247:1306-1310, 1990) (Year: 1990).*
Whisstock et al. (Quarterly Reviews in Biophysics. 36(3):307-340, 2007) (Year: 2007).*
Lazar et al. (Molecular and Cellular Biology. 1988; 8(3): 1247-1252) (Year: 1988).*

\* cited by examiner

*Primary Examiner* — Gregory S Emch
*Assistant Examiner* — Ashley H. Gao
(74) *Attorney, Agent, or Firm* — Tarolli, Sundheim, Covell & Tummino LLP

(57) ABSTRACT

Compounds and pharmaceutical compositions thereof for inducing apoptosis in a cell expressing Bcl-2 and IP$_3$R and their use in a method for treating neoplastic disorders in a subject.

10 Claims, 6 Drawing Sheets

INHIBITORS OF BCL-2

RELATED APPLICATION

This application claims priority from U.S. Provisional Application No. 62/291,915, filed Feb. 5, 2016, the subject matter of which is incorporated herein by reference in its entirety.

GOVERNMENT FUNDING

This invention was made with government support under CA085804 awarded by the National Institutes of Health. The government has certain rights in the invention.

TECHNICAL FIELD

This application relates generally to compounds that can be used to inhibit the interaction of Bcl-2 to the inositol 1,4,5-triphosphate receptor ($IP_3R$). This application also relates to pharmaceutical compositions containing these compounds and methods of using the compounds for the treatment of Bcl-2 associated diseases and disorders.

BACKGROUND

Apoptosis is an important process in the development of cells and in maintaining the proper number of cells in the body. Candidates for apoptosis include cells that may be a danger to an organism, such as cells with damaged DNA or cells growing at improper rates. However, apoptosis is also applied to normal cells that have simply become obsolete as organisms grow and develop.

Bcl-2 protein is known to inhibit apoptotic cell death. Bcl-2 protein serves as a check on apoptosis allowing healthy and useful cells to survive. Anti-apoptotic molecules, such as Bcl-2 are often overexpressed in cancer cells and their inhibition is an attractive target for selective killing of tumor cells via induction of apoptosis. Bcl-2 overexpression and/or activation has been correlated with resistance to chemotherapy, to radiotherapy and to development of hormone-resistant tumors. Inhibition of apoptosis by Bcl-2 contributes to cancer by inhibiting cell death. Thus, inhibiting Bcl-2 activity in cancer cells can reduce chemotherapeutic resistance and increase the killing of cancer cells.

The Bcl-2 gene was discovered as the translocated locus in a B-cell leukemia. Bcl-2 contains a single transmembrane domain and is localized within a cell to the outer mitochondrial, nuclear, and endoplasmic reticulum membranes. Bcl-2 was first isolated as a breakpoint rearrangement in human follicular lymphomas. In humans, most follicular B-cell lymphomas contain a chromosomal translocation that moves the gene for Bcl-2 from its normal location to a position within the genes for immunoglobulins. In this new location, higher quantities of Bcl-2 are produced. Since Bcl-2 is a potent pro-survival protein, it shields the cancer cells from apoptotic instruction.

The effector molecules in the apoptotic pathway are a family of enzymes known as the caspases. The Bcl-2 protein suppresses apoptosis by preventing the activation of the caspases that carry out the process. Caspase enzymes are cystein proteases that selectively cleave proteins at sites just C-terminal to aspartate residues. These proteases have specific intracellular targets such as proteins of the nuclear lamina and cytoskeleton. The cleavage of these substrates leads to the demise of a cell.

The inositol 1,4,5-triphosphate ($IP_3$) messenger molecule is water soluble, and can diffuse within the cytosol carrying an activated G protein signal from the cell surface to the endoplasmic reticulum (ER) surface. $IP_3$ binds to an $IP_3R$ and induces opening of the channel allowing $Ca^{2+}$ ions to exit from the ER into the cytosol. The released calcium then triggers a mass exodus of cytochrome c from all mitochondria in the cell, thus activating the caspase and nuclease enzymes that finalize the apoptotic process.

It has previously been shown that Bcl-2 interacts with the inositol 1,4,5-triphosphate receptor ($IP_3R$) and inhibits $IP_3$-mediated $Ca^{2+}$ release from the ER, thereby inhibiting anti-CD3 induced apoptosis in immature T cells (JCB 166: 193-203,2004; JCB 172: 127-137, 2006). $IP_3R$ have a broad tissue distribution and are mostly found in the cell integrated into the endoplasmic reticulum. The $IP_3R$ is a large six transmembrane ligand gated ion channel, which mainly transmits calcium ions and thereby facilitates triggers apoptosis.

SUMMARY

This application relates to compounds and pharmaceutical compositions thereof that inhibit binding of Bcl-2 to $IP_3$ receptors ($IP_3R$) of cells that express $IP_3R$ and Bcl-2.

In one aspect, the application provides a method of inducing apoptosis in a cell expressing Bcl-2 and $IP_3R$. The method includes administering to the cell a therapeutically effective amount of a compound that inhibits binding of Bcl-2 to $IP_3$ receptors ($IP_3R$) of cells that express $IP_3R$ and Bcl-2.

In some embodiments, the compound is derived from the Bcl-2 binding domain of $IP^3R$. The Bcl-2 binding domain of $IP_3R$ can include the BH4 binding domain of $IP_3R$. In some aspects, the compound can include a BIRD-2 (Bcl-2-$IP_3R$ interaction Disrupter-2) mimetic agent. In some aspects, the compound can include a non-peptide BIRD-2 mimetic agent. In certain aspects, the compound can reverse the interaction of Bcl-2 with $IP_3R$ of cells that express Bcl-2 and $IP_3R$.

The method can further include administering a second agent to the cell that inhibits binding of Bcl-2 to BH3 pro-apoptotic proteins and in combination with a compound that inhibits binding of Bcl-2 to $IP_3R$, induces synergistic cytotoxicity of cells that express Bcl-2 and $IP_3R$. The second agent can include at least one of a chromene, a thiazolidine, a benzenesulfonyl, a benzenesulfonamide, an antimycin, a dibenzodiazocine, a terphenyl, an indole, gossypol, apogossypol, an epigallocatechingallate, or a theaflavin. The second agent can also include N-(4-(4-(4'-chloro-biphenyl-2-ylmethyl)-piperazin-1-yl)-benzoyl)-4-(3-dimethylamino-1-phenylsulfanylmethyl-propylamino)-3-nitro-benzene-sulfonamide, ABT-737, ABT-263, and ABT-199.

The application further relates to a method of treating a neoplastic disorder, such as chronic lymphocytic leukemia or multiple myeloma, in a subject. The method includes administering to neoplastic cells of the subject expressing $IP_3R$ and Bcl-2 a therapeutically effective amount of a compound that inhibits binding of Bcl-2 to $IP_3$ receptors ($IP_3R$) of cells that express $IP_3R$ and Bcl-2.

In some embodiments, the compound is derived from the Bcl-2 binding domain of $IP_3R$. The Bcl-2 binding domain of $IP_3R$ can include the BH4 binding domain of $IP_3R$. In some aspects, the compound can include a BIRD-2 (Bcl-2-$IP_3R$ interaction Disrupter-2) mimetic agent. In some aspects, the compound can include a non-peptide BIRD-2 mimetic agent. In certain aspects, the compound can reverse the interaction of Bcl-2 with IP$_3$R of cells that express Bcl-2 and IP$_3$R.

The method can further include administering a second agent to the cell that inhibits binding of Bcl-2 to BH3 pro-apoptotic proteins in combination with a compound that inhibits binding of Bcl-2 to IP$_3$R, induces synergistic cytotoxicity of cells that express Bcl-2 and IP$_3$R. The second agent can include at least one of a chromene, a thiazolidine, a benzenesulfonyl, a benzenesulfonamide, an antimycin, a dibenzodiazocine, a terphenyl, an indole, gossypol, apogossypol, an epigallocatechingallate, or a theaflavin. The second agent can also include N-(4-(4-(4'-chloro-biphenyl-2-ylmethyl)-piperazin-1-yl)-benzoyl)-4-(3-dimethylamino-1-phenylsulfanylmethyl-propylamino)-3-nitro-benzene-sulfonamide, ABT-737, ABT-263, and ABT-199.

In some aspects the neoplastic disorder includes a Bcl-2 associated cancer. The Bcl-2 associated cancer can be selected from the group consisting of chronic lymphocytic leukemia (CLL), follicular lymphoma, diffuse large B-cell lymphoma, and multiple myeloma (MM).

BRIEF DESCRIPTION OF DRAWINGS

Further features of the present invention will become apparent to those skilled in the art to which the present invention relates from reading the following description of the invention with reference to the accompanying drawings.

DETAILED DESCRIPTION

Figure 1:
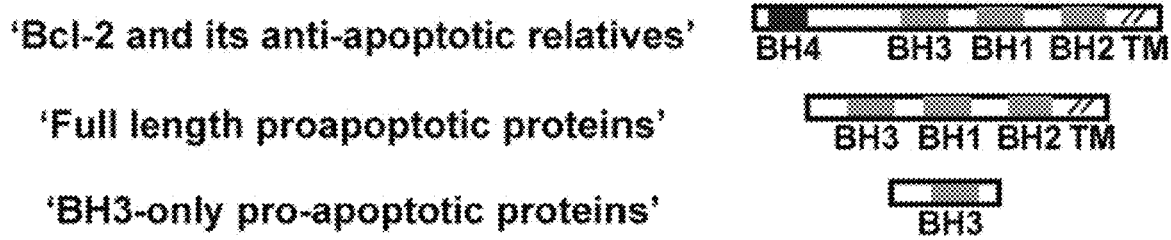
FIG. 1 illustrates a graphic showing the Bcl-2 family. Bcl-2 has four Bcl-2 homology (BH) domains, whereas pro-apoptotic family members lack a BH4 domain. In Bcl-2, BH1-3 form a hydrophobic groove that binds and inhibits full length (e.g., Bax, Bak) and BH3-only (e.g., Bim, Bad) family members. The BH4 domain of Bcl-2 binds to IP$_3$Rs.

For convenience, certain terms employed in the specification, examples, and appended claims are collected here. Unless defined otherwise, all technical and scientific terms used herein have the same meaning as commonly understood by one of ordinary skill in the art to which this application belongs.

The articles "a" and "an" are used herein to refer to one or to more than one (i.e., to at least one) of the grammatical object of the article. By way of example, "an element" means one element or more than one element.

The terms "comprise," "comprising," "include," "including," "have," and "having" are used in the inclusive, open sense, meaning that additional elements may be included. The terms "such as", "e.g.", as used herein are non-limiting and are for illustrative purposes only. "Including" and "including but not limited to" are used interchangeably.

The term "or" as used herein should be understood to mean "and/or", unless the context clearly indicates otherwise.

As used herein, the term "about" or "approximately" refers to a quantity, level, value, number, frequency, percentage, dimension, size, amount, weight or length that varies by as much as 15%, 10%, 9%, 8%, 7%, 6%, 5%, 4%, 3%, 2% or 1% to a reference quantity, level, value, number, frequency, percentage, dimension, size, amount, weight or length. In one embodiment, the term "about" or "approximately" refers a range of quantity, level, value, number, frequency, percentage, dimension, size, amount, weight or length ±15%, ±10%, ±9%, ±8%, ±7%, ±6%, ±5%, ±4%, ±3%, ±2%, or ±1% about a reference quantity, level, value, number, frequency, percentage, dimension, size, amount, weight or length.

It will be noted that the structure of some of the compounds of the application include asymmetric (chiral) carbon or sulfur atoms. It is to be understood accordingly that the isomers arising from such asymmetry are included herein, unless indicated otherwise. Such isomers can be obtained in substantially pure form by classical separation techniques and by stereochemically controlled synthesis. The compounds of this application may exist in stereoisomeric form, therefore can be produced as individual stereoisomers or as mixtures.

The term "isomerism" means compounds that have identical molecular formulae but that differ in the nature or the sequence of bonding of their atoms or in the arrangement of their atoms in space. Isomers that differ in the arrangement of their atoms in space are termed "stereoisomers". Stereoisomers that are not mirror images of one another are termed "diastereoisomers", and stereoisomers that are non-superimposable mirror images are termed "enantiomers", or sometimes optical isomers. A carbon atom bonded to four nonidentical substituents is termed a "chiral center" whereas a sulfur bound to three or four different substitutents, e.g., sulfoxides or sulfinimides, is likewise termed a "chiral center".

The term "chiral isomer" means a compound with at least one chiral center. It has two enantiomeric forms of opposite chirality and may exist either as an individual enantiomer or as a mixture of enantiomers. A mixture containing equal amounts of individual enantiomeric forms of opposite chirality is termed a "racemic mixture". A compound that has more than one chiral center has 2n−1 enantiomeric pairs, where n is the number of chiral centers. Compounds with more than one chiral center may exist as either an individual diastereomer or as a mixture of diastereomers, termed a "diastereomeric mixture". When one chiral center is present, a stereoisomer may be characterized by the absolute configuration (R or S) of that chiral center. Alternatively, when one or more chiral centers are present, a stereoisomer may be characterized as (+) or (−). Absolute configuration refers to the arrangement in space of the substituents attached to the chiral center. The substituents attached to the chiral center under consideration are ranked in accordance with the Sequence Rule of Cahn, Ingold and Prelog. (Cahn et al, Angew. Chem. Inter. Edit. 1966, 5, 385; errata 511; Cahn et al., Angew. Chem. 1966, 78, 413; Cahn and Ingold, J Chem. Soc. 1951 (London), 612; Cahn et al., Experientia 1956, 12, 81; Cahn, J., Chem. Educ. 1964, 41, 116).

The term "geometric Isomers" means the diastereomers that owe their existence to hindered rotation about double bonds. These configurations are differentiated in their names by the prefixes cis and trans, or Z and E, which indicate that the groups are on the same or opposite side of the double bond in the molecule according to the Cahn-Ingold-Prelog rules. Further, the structures and other compounds discussed in this application include all atropic isomers thereof.

The term "atropic isomers" are a type of stereoisomer in which the atoms of two isomers are arranged differently in space. Atropic isomers owe their existence to a restricted rotation caused by hindrance of rotation of large groups about a central bond. Such atropic isomers typically exist as a mixture, however as a result of recent advances in chromatography techniques, it has been possible to separate mixtures of two atropic isomers in select cases.

The terms "crystal polymorphs" or "polymorphs" or "crystal forms" means crystal structures in which a compound (or salt or solvate thereof) can crystallize in different crystal packing arrangements, all of which have the same elemental composition. Different crystal forms usually have different X-ray diffraction patterns, infrared spectral, melting points, density hardness, crystal shape, optical and electrical properties, stability and solubility. Recrystallization solvent, rate of crystallization, storage temperature, and other factors may cause one crystal form to dominate. Crystal polymorphs of the compounds can be prepared by crystallization under different conditions.

The term "derivative" refers to compounds that have a common core structure, and are substituted with various groups as described herein.

The term "bioisostere" refers to a compound resulting from the exchange of an atom or of a group of atoms with another, broadly similar, atom or group of atoms. The objective of a bioisosteric replacement is to create a new compound with similar biological properties to the parent compound. The bioisosteric replacement may be physicochemically or topologically based. Examples of carboxylic acid bioisosteres include acyl sulfonimides, tetrazoles, sulfonates, and phosphonates. See, e.g., Patani and LaVoie, Chem. Rev. 96, 3147-3176 (1996).

The phrases "parenteral administration" and "administered parenterally" are art-recognized terms, and include modes of administration other than enteral and topical administration, such as injections, and include, without limitation, intravenous, intramuscular, intrapleural, intravascular, intrapericardial, intraarterial, intrathecal, intracapsular, intraorbital, intracardiac, intradermal, intraperitoneal, transtracheal, subcutaneous, subcuticular, intra-articular, subcapsular, subarachnoid, intraspinal and intrastemal injection and infusion.

The term "treating" is art-recognized and includes inhibiting a disease, disorder or condition in a subject, e.g., impeding its progress; and relieving the disease, disorder or condition, e.g., causing regression of the disease, disorder and/or condition. Treating the disease or condition includes ameliorating at least one symptom of the particular disease or condition, even if the underlying pathophysiology is not affected.

The term "preventing" is art-recognized and includes stopping a disease, disorder or condition from occurring in a subject, which may be predisposed to the disease, disorder and/or condition but has not yet been diagnosed as having it. Preventing a condition related to a disease includes stopping the condition from occurring after the disease has been diagnosed but before the condition has been diagnosed.

The term "pharmaceutical composition" refers to a formulation containing the disclosed compounds in a form suitable for administration to a subject. In a preferred embodiment, the pharmaceutical composition is in bulk or in unit dosage form. The unit dosage form is any of a variety of forms, including, for example, a capsule, an IV bag, a tablet, a single pump on an aerosol inhaler, or a vial. The quantity of active ingredient (e.g., a formulation of the disclosed compound or salts thereof) in a unit dose of composition is an effective amount and is varied according to the particular treatment involved. One skilled in the art will appreciate that it is sometimes necessary to make routine variations to the dosage depending on the age and condition of the patient. The dosage will also depend on the route of administration. A variety of routes are contemplated, including oral, pulmonary, rectal, parenteral, transdermal, subcutaneous, intravenous, intramuscular, intraperitoneal, intranasal, inhalational, and the like. Dosage forms for the topical or transdermal administration of a compound described herein includes powders, sprays, ointments, pastes, creams, lotions, gels, solutions, patches, nebulized compounds, and inhalants. In a preferred embodiment, the active compound is mixed under sterile conditions with a pharmaceutically acceptable carrier, and with any preservatives, buffers, or propellants that are required.

The term "flash dose" refers to compound formulations that are rapidly dispersing dosage forms.

The term "immediate release" is defined as a release of compound from a dosage form in a relatively brief period of time, generally up to about 60 minutes. The term "modified release" is defined to include delayed release, extended release, and pulsed release. The term "pulsed release" is defined as a series of releases of drug from a dosage form. The term "sustained release" or "extended release" is defined as continuous release of a compound from a dosage form over a prolonged period.

The phrase "pharmaceutically acceptable" is art-recognized. In certain embodiments, the term includes compositions, polymers and other materials and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically acceptable carrier" is art-recognized, and includes, for example, pharmaceutically acceptable materials, compositions or vehicles, such as a liquid or solid filler, diluent, excipient, solvent or encapsulating material, involved in carrying or transporting any subject composition from one organ, or portion of the body, to another organ, or portion of the body. Each carrier must be "acceptable" in the sense of being compatible with the other ingredients of a subject composition and not injurious to the patient. In certain embodiments, a pharmaceutically acceptable carrier is non-pyrogenic. Some examples of materials which may serve as pharmaceutically acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, sunflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations.

The compounds of the application are capable of further forming salts. All of these forms are also contemplated herein.

"Pharmaceutically acceptable salt" of a compound means a salt that is pharmaceutically acceptable and that possesses the desired pharmacological activity of the parent compound. For example, the salt can be an acid addition salt. One embodiment of an acid addition salt is a hydrochloride salt. The pharmaceutically acceptable salts can be synthesized from a parent compound that contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, non-aqueous media like ether, ethyl acetate, ethanol, isopropanol, or acetonitrile being preferred. Lists of salts are found in Remington's Pharmaceutical Sciences, 18th ed. (Mack Publishing Company, 1990).

The compounds described herein can also be prepared as esters, for example pharmaceutically acceptable esters. For example, a carboxylic acid function group in a compound can be converted to its corresponding ester, e.g., a methyl, ethyl, or other ester. Also, an alcohol group in a compound can be converted to its corresponding ester, e.g., an acetate, propionate, or other ester.

The compounds described herein can also be prepared as prodrugs, for example pharmaceutically acceptable prodrugs. The terms "pro-drug" and "prodrug" are used interchangeably herein and refer to any compound, which releases an active parent drug in vivo. Since prodrugs are known to enhance numerous desirable qualities of pharmaceuticals (e.g., solubility, bioavailability, manufacturing, etc.) the compounds can be delivered in prodrug form. Thus, the compounds described herein are intended to cover prodrugs of the presently claimed compounds, methods of delivering the same and compositions containing the same. "Prodrugs" are intended to include any covalently bonded carriers that release an active parent drug in vivo when such prodrug is administered to a subject. Prodrugs are prepared by modifying functional groups present in the compound in such a way that the modifications are cleaved, either in routine manipulation or in vivo, to the parent compound. Prodrugs include compounds wherein a hydroxy, amino, sulfhydryl, carboxy, or carbonyl group is bonded to any group that may be cleaved in vivo to form a free hydroxyl, free amino, free sulfhydryl, free carboxy or free carbonyl group, respectively. Prodrugs can also include a precursor (forerunner) of a compound described herein that undergoes chemical conversion by metabolic processes before becoming an active or more active pharmacological agent or active compound described herein.

Examples of prodrugs include, but are not limited to, esters (e.g., acetate, dialkylaminoacetates, formates, phosphates, sulfates, and benzoate derivatives) and carbamates (e.g., N,N-dimethylaminocarbonyl) of hydroxy functional groups, ester groups (e.g., ethyl esters, morpholinoethanol esters) of carboxyl functional groups, N-acyl derivatives (e.g., N-acetyl) N-Mannich bases, Schiff bases and enaminones of amino functional groups, oximes, acetals, ketals and enol esters of ketone and aldehyde functional groups in compounds, and the like, as well as sulfides that are oxidized to form sulfoxides or sulfones.

The term "protecting group" refers to a grouping of atoms that when attached to a reactive group in a molecule masks, reduces or prevents that reactivity. Examples of protecting groups can be found in Green and Wuts, Protective Groups in Organic Chemistry, (Wiley, 2.sup.nd ed. 1991); Harrison and Harrison et al., Compendium of Synthetic Organic Methods, Vols. 1-8 (John Wiley and Sons, 1971-1996); and Kocienski, Protecting Groups, (Verlag, $3^{rd}$ ed. 2003).

The term "amine protecting group" is intended to mean a functional group that converts an amine, amide, or other nitrogen-containing moiety into a different chemical group that is substantially inert to the conditions of a particular chemical reaction. Amine protecting groups are preferably removed easily and selectively in good yield under conditions that do not affect other functional groups of the molecule. Examples of amine protecting groups include, but are not limited to, formyl, acetyl, benzyl, t-butyldimethylsilyl, t-butyldiphenylsilyl, t-butyloxycarbonyl (Boc), p-methoxybenzyl, methoxymethyl, tosyl, trifluoroacetyl, trimethylsilyl (TMS), fluorenyl-methyloxycarbonyl, 2-trimethylsilyl-ethyoxycarbonyl, 1-methyl-1-(4-biphenylyl) ethoxycarbonyl, allyloxycarbonyl, benzyloxycarbonyl (CBZ), 2-trimethylsilyl-ethanesulfonyl (SES), trityl and substituted trityl groups, 9-fluorenylmethyloxycarbonyl (FMOC), nitro-veratryloxycarbonyl (NVOC), and the like. Those of skill in the art can identify other suitable amine protecting groups.

Representative hydroxy protecting groups include those where the hydroxy group is either acylated or alkylated such as benzyl, and trityl ethers as well as alkyl ethers, tetrahydropyranyl ethers, trialkylsilyl ethers and allyl ethers.

Additionally, the salts of the compounds described herein, can exist in either hydrated or unhydrated (the anhydrous) form or as solvates with other solvent molecules. Non-limiting examples of hydrates include monohydrates, dihydrates, etc. Nonlimiting examples of solvates include ethanol solvates, acetone solvates, etc.

The term "solvates" means solvent addition forms that contain either stoichiometric or non-stoichiometric amounts of solvent. Some compounds have a tendency to trap a fixed molar ratio of solvent molecules in the crystalline solid state, thus forming a solvate. If the solvent is water the solvate formed is a hydrate, when the solvent is alcohol, the solvate formed is an alcoholate. Hydrates are formed by the combination of one or more molecules of water with one of the substances in which the water retains its molecular state as $H_2O$, such combination being able to form one or more hydrate.

The compounds, salts and prodrugs described herein can exist in several tautomeric forms, including the enol and imine form, and the keto and enamine form and geometric isomers and mixtures thereof. Tautomers exist as mixtures of a tautomeric set in solution. In solid form, usually one tautomer predominates. Even though one tautomer may be described, the present application includes all tautomers of the present compounds. A tautomer is one of two or more structural isomers that exist in equilibrium and are readily converted from one isomeric form to another. This reaction results in the formal migration of a hydrogen atom accompanied by a switch of adjacent conjugated double bonds. In solutions where tautomerization is possible, a chemical equilibrium of the tautomers will be reached. The exact ratio of the tautomers depends on several factors, including temperature, solvent, and pH. The concept of tautomers that are interconvertable by tautomerizations is called tautomerism.

Of the various types of tautomerism that are possible, two are commonly observed. In keto-enol tautomerism a simultaneous shift of electrons and a hydrogen atom occurs.

Tautomerizations can be catalyzed by: Base: 1. deprotonation; 2. formation of a delocalized anion (e.g., an enolate); 3. protonation at a different position of the anion; Acid: 1. protonation; 2. formation of a delocalized cation; 3. deprotonation at a different position adjacent to the cation.

The term "analogue" refers to a chemical compound that is structurally similar to another but differs slightly in composition (as in the replacement of one atom by an atom of a different element or in the presence of a particular functional group, or the replacement of one functional group by another functional group). Thus, an analogue is a compound that is similar or comparable in function and appearance, but not in structure or origin to the reference compound.

A "patient," "subject," or "host" to be treated by the subject method may mean either a human or non-human animal, such as a mammal, a fish, a bird, a reptile, or an amphibian. Thus, the subject of the herein disclosed methods can be a human, non-human primate, horse, pig, rabbit, dog, sheep, goat, cow, cat, guinea pig or rodent. The term does not denote a particular age or sex. Thus, adult and newborn subjects, as well as fetuses, whether male or female, are intended to be covered. In one aspect, the subject is a mammal. A patient refers to a subject afflicted with a disease or disorder.

The terms "prophylactic" or "therapeutic" treatment is art-recognized and includes administration to the host of one or more of the subject compositions. If it is administered prior to clinical manifestation of the unwanted condition (e.g., disease or other unwanted state of the host animal) then the treatment is prophylactic, i.e., it protects the host against developing the unwanted condition, whereas if it is administered after manifestation of the unwanted condition, the treatment is therapeutic (i.e., it is intended to diminish, ameliorate, or stabilize the existing unwanted condition or side effects thereof).

The terms "therapeutic agent", "drug", "medicament" and "bioactive substance" are art-recognized and include molecules and other agents that are biologically, physiologically, or pharmacologically active substances that act locally or systemically in a patient or subject to treat a disease or condition. The terms include without limitation pharmaceutically acceptable salts thereof and prodrugs. Such agents may be acidic, basic, or salts; they may be neutral molecules, polar molecules, or molecular complexes capable of hydrogen bonding; they may be prodrugs in the form of ethers, esters, amides and the like that are biologically activated when administered into a patient or subject.

The phrase "therapeutically effective amount" or "pharmaceutically effective amount" is an art-recognized term. In certain embodiments, the term refers to an amount of a therapeutic agent that produces some desired effect at a reasonable benefit/risk ratio applicable to any medical treatment. In certain embodiments, the term refers to that amount necessary or sufficient to eliminate, reduce or maintain a target of a particular therapeutic regimen. The effective amount may vary depending on such factors as the disease or condition being treated, the particular targeted constructs being administered, the size of the subject or the severity of the disease or condition. One of ordinary skill in the art may empirically determine the effective amount of a particular compound without necessitating undue experimentation. In certain embodiments, a therapeutically effective amount of a therapeutic agent for in vivo use will likely depend on a number of factors, including: the rate of release of an agent from a polymer matrix, which will depend in part on the chemical and physical characteristics of the polymer; the identity of the agent; the mode and method of administration; and any other materials incorporated in the polymer matrix in addition to the agent.

The term "ED50" is art-recognized. In certain embodiments, ED50 means the dose of a drug, which produces 50% of its maximum response or effect, or alternatively, the dose, which produces a pre-determined response in 50% of test subjects or preparations. The term "LD50" is art-recognized. In certain embodiments, LD50 means the dose of a drug, which is lethal in 50% of test subjects. The term "therapeutic index" is an art-recognized term, which refers to the therapeutic index of a drug, defined as LD50/ED50.

The terms "$IC_{50}$," or "half maximal inhibitory concentration" is intended to refer to the concentration of a substance (e.g., a compound or a drug) that is required for 50% inhibition of a biological process, or component of a process, including a protein, subunit, organelle, ribonucleoprotein, etc.

With respect to any chemical compounds, the present application is intended to include all isotopes of atoms occurring in the present compounds. Isotopes include those atoms having the same atomic number but different mass numbers. By way of general example and without limitation, isotopes of hydrogen include tritium and deuterium, and isotopes of carbon include C-13 and C-14.

When a bond to a substituent is shown to cross a bond connecting two atoms in a ring, then such substituent can be bonded to any atom in the ring. When a substituent is listed without indicating the atom via which such substituent is bonded to the rest of the compound of a given formula, then such substituent can be bonded via any atom in such substituent. Combinations of substituents and/or variables are permissible, but only if such combinations result in stable compounds.

When an atom or a chemical moiety is followed by a subscripted numeric range (e.g., $C_{1-6}$), it is meant to encompass each number within the range as well as all intermediate ranges. For example, "$C_{1-6}$ alkyl" is meant to include alkyl groups with 1, 2, 3, 4, 5, 6, 1-6, 1-5, 1-4, 1-3, 1-2, 2-6, 2-5, 2-4, 2-3, 3-6, 3-5, 3-4, 4-6, 4-5, and 5-6 carbons.

The term "alkyl" is intended to include both branched (e.g., isopropyl, tert-butyl, isobutyl), straight-chain e.g., methyl, ethyl, propyl, butyl, pentyl, hexyl, heptyl, octyl, nonyl, decyl), and cycloalkyl (e.g., alicyclic) groups (e.g., cyclopropyl, cyclopentyl, cyclohexyl, cycloheptyl, cyclooctyl), alkyl substituted cycloalkyl groups, and cycloalkyl substituted alkyl groups. Such aliphatic hydrocarbon groups have a specified number of carbon atoms. For example, $C_{1-6}$ alkyl is intended to include $C_1$, $C_2$, $C_3$, $C_4$, $C_5$, and $C_6$ alkyl groups. As used herein, "lower alkyl" refers to alkyl groups having from 1 to 6 carbon atoms in the backbone of the carbon chain. "Alkyl" further includes alkyl groups that have oxygen, nitrogen, sulfur or phosphorous atoms replacing one or more hydrocarbon backbone carbon atoms. In certain embodiments, a straight chain or branched chain alkyl has six or fewer carbon atoms in its backbone (e.g., $C_1$-$C_6$ for straight chain, $C_3$-$C_6$ for branched chain), for example four or fewer. Likewise, certain cycloalkyls have from three to eight carbon atoms in their ring structure, such as five or six carbons in the ring structure.

The term "substituted alkyls" refers to alkyl moieties having substituents replacing a hydrogen on one or more carbons of the hydrocarbon backbone. Such substituents can include, for example, alkyl, alkenyl, alkynyl, halogen, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, cyano, amino (including alkylamino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety. Cycloalkyls can be further substituted, e.g., with the substituents described above. An "alkylaryl" or an "aralkyl" moiety is an alkyl substituted with an aryl (e.g., phenylmethyl (benzyl)). If not otherwise indicated, the terms "alkyl" and "lower alkyl" include linear, branched, cyclic, unsubstituted, substituted, and/or heteroatom-containing alkyl or lower alkyl, respectively.

The term "alkenyl" refers to a linear, branched or cyclic hydrocarbon group of 2 to about 24 carbon atoms containing at least one double bond, such as ethenyl, n-propenyl, isopropenyl, n-butenyl, isobutenyl, octenyl, decenyl, tetradecenyl, hexadecenyl, eicosenyl, tetracosenyl, cyclopentenyl, cyclohexenyl, cyclooctenyl, and the like. Generally, although again not necessarily, alkenyl groups can contain 2 to about 18 carbon atoms, and more particularly 2 to 12 carbon atoms. The term "lower alkenyl" refers to an alkenyl group of 2 to 6 carbon atoms, and the specific term "cycloalkenyl" intends a cyclic alkenyl group, preferably having 5 to 8 carbon atoms. The term "substituted alkenyl" refers to alkenyl substituted with one or more substituent groups, and the terms "heteroatom-containing alkenyl" and "heteroalkenyl" refer to alkenyl or heterocycloalkenyl (e.g., heterocyclcohexenyl) in which at least one carbon atom is replaced with a heteroatom. If not otherwise indicated, the terms "alkenyl" and "lower alkenyl" include linear, branched, cyclic, unsubstituted, substituted, and/or heteroatom-containing alkenyl and lower alkenyl, respectively.

The term "alkynyl" refers to a linear or branched hydrocarbon group of 2 to 24 carbon atoms containing at least one triple bond, such as ethynyl, n-propynyl, and the like. Generally, although again not necessarily, alkynyl groups can contain 2 to about 18 carbon atoms, and more particularly can contain 2 to 12 carbon atoms. The term "lower alkynyl" intends an alkynyl group of 2 to 6 carbon atoms. The term "substituted alkynyl" refers to alkynyl substituted with one or more substituent groups, and the terms "heteroatom-containing alkynyl" and "heteroalkynyl" refer to alkynyl in which at least one carbon atom is replaced with a heteroatom. If not otherwise indicated, the terms "alkynyl" and "lower alkynyl" include linear, branched, unsubstituted, substituted, and/or heteroatom-containing alkynyl and lower alkynyl, respectively.

The terms "alkyl", "alkenyl", and "alkynyl" are intended to include moieties which are diradicals, i.e., having two points of attachment. A nonlimiting example of such an alkyl moiety that is a diradical is —$CH_2CH_2$—, i.e., a $C_2$ alkyl group that is covalently bonded via each terminal carbon atom to the remainder of the molecule.

The term "alkoxy" refers to an alkyl group bound through a single, terminal ether linkage; that is, an "alkoxy" group may be represented as —O-alkyl where alkyl is as defined above. A "lower alkoxy" group intends an alkoxy group containing 1 to 6 carbon atoms, and includes, for example, methoxy, ethoxy, n-propoxy, isopropoxy, t-butyloxy, etc. Preferred substituents identified as "$C_1$-$C_6$ alkoxy" or "lower alkoxy" herein contain 1 to 3 carbon atoms, and particularly preferred such substituents contain 1 or 2 carbon atoms (i.e., methoxy and ethoxy).

The term "aryl" refers to an aromatic substituent containing a single aromatic ring or multiple aromatic rings that are fused together, directly linked, or indirectly linked (such that the different aromatic rings are bound to a common group such as a methylene or ethylene moiety). Aryl groups can contain 5 to 20 carbon atoms, and particularly preferred aryl groups can contain 5 to 14 carbon atoms. Examples of aryl groups include benzene, phenyl, pyrrole, furan, thiophene, thiazole, isothiazole, imidazole, triazole, tetrazole, pyrazole, oxazole, isooxazole, pyridine, pyrazine, pyridazine, and pyrimidine, and the like. Furthermore, the term "aryl" includes multicyclic aryl groups, e.g., tricyclic, bicyclic, e.g., naphthalene, benzoxazole, benzodioxazole, benzothiazole, benzoimidazole, benzothiophene, methylenedioxyphenyl, quinoline, isoquinoline, napthridine, indole, benzofuran, purine, benzofuran, deazapurine, or indolizine. Those aryl groups having heteroatoms in the ring structure may also be referred to as "aryl heterocycles", "heterocycles," "heteroaryls" or "heteroaromatics". The aromatic ring can be substituted at one or more ring positions with such substituents as described above, as for example, halogen, hydroxyl, alkoxy, alkylcarbonyloxy, arylcarbonyloxy, alkoxycarbonyloxy, aryloxycarbonyloxy, carboxylate, alkylcarbonyl, alkylaminocarbonyl, aralkylaminocarbonyl, alkenylaminocarbonyl, alkylcarbonyl, arylcarbonyl, aralkylcarbonyl, alkenylcarbonyl, alkoxycarbonyl, aminocarbonyl, alkylthiocarbonyl, phosphate, phosphonato, phosphinato, cyano, amino (including alkylamino, dialkylamino, arylamino, diaryl amino, and al kylaryl amino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety. Aryl groups can also be fused or bridged with alicyclic or heterocyclic rings, which are not aromatic so as to form a multicyclic system (e.g., tetralin, methylenedioxyphenyl). If not otherwise indicated, the term "aryl" includes unsubstituted, substituted, and/or heteroatom-containing aromatic substituents.

The term "alkaryl" refers to an aryl group with an alkyl substituent, and the term "aralkyl" refers to an alkyl group with an aryl substituent, wherein "aryl" and "alkyl" are as defined above. Exemplary aralkyl groups contain 6 to 24 carbon atoms, and particularly preferred aralkyl groups contain 6 to 16 carbon atoms. Examples of aralkyl groups include, without limitation, benzyl, 2-phenyl-ethyl, 3-phenyl-propyl, 4-phenyl-butyl, 5-phenyl-pentyl, 4-phenylcyclohexyl, 4-benzylcyclohexyl, 4-phenylcyclohexylmethyl, 4-benzylcyclohexylmethyl, and the like. Alkaryl groups include, for example, p-methylphenyl, 2,4-dimethylphenyl, p-cyclohexylphenyl, 2,7-dimethylnaphthyl, 7-cyclooctylnaphthyl, 3-ethyl-cyclopenta-1,4-diene, and the like.

The terms "heterocyclyl" or "heterocyclic group" include closed ring structures, e.g., 3- to 10-, or 4- to 7-membered rings, which include one or more heteroatoms. "Heteroatom" includes atoms of any element other than carbon or hydrogen. Examples of heteroatoms include nitrogen, oxygen, sulfur and phosphorus.

Heterocyclyl groups can be saturated or unsaturated and include pyrrolidine, oxolane, thiolane, piperidine, piperazine, morpholine, lactones, lactams, such as azetidinones and pyrrolidinones, sultams, and sultones. Heterocyclic groups such as pyrrole and furan can have aromatic character. They include fused ring structures, such as quinoline and isoquinoline. Other examples of heterocyclic groups include pyridine and purine. The heterocyclic ring can be substituted at one or more positions with such substituents as described above, as for example, halogen, hydroxyl, alkylcarbonyloxy, arylcarbonyloxy, alkoxycarbonyloxy, aryloxycarbonyloxy, carboxylate, alkylcarbonyl, alkoxycarbonyl, aminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, sulfonato, sulfamoyl, sulfonamido, nitro, trifluoromethyl, cyano, azido, heterocyclyl, or an aromatic or heteroaromatic moiety. Heterocyclic groups can also be substituted at one or more constituent atoms with, for example, a lower alkyl, a lower alkenyl, a lower alkoxy, a lower alkylthio, a lower alkylamino, a lower alkylcarboxyl, a nitro, a hydroxyl, —$CF_3$, or —CN, or the like.

The term "halo" or "halogen" refers to fluoro, chloro, bromo, and iodo. "Counterion" is used to represent a small, negatively charged species such as fluoride, chloride, bromide, iodide, hydroxide, acetate, and sulfate. The term sulfoxide refers to a sulfur attached to 2 different carbon atoms and one oxygen and the S—O bond can be graphically represented with a double bond (S=O), a single bond without charges (S—O) or a single bond with charges [S(+)—O(-)].

The terms "substituted" as in "substituted alkyl," "substituted aryl," and the like, as alluded to in some of the aforementioned definitions, is meant that in the alkyl, aryl, or other moiety, at least one hydrogen atom bound to a carbon (or other) atom is replaced with one or more non-hydrogen substituents. Examples of such substituents include, without limitation: functional groups such as halo, hydroxyl, silyl, sulfhydryl, $C_1$-$C_{24}$ alkoxy, $C_2$-$C_{24}$ alkenyloxy, $C_2$-$C_{24}$ alkynyloxy, $C_5$-$C_{20}$ aryloxy, acyl (including $C_2$-$C_{24}$ alkylcarbonyl (—CO-alkyl) and $C_6$-$C_{20}$ arylcarbonyl (—CO-aryl)), acyloxy (—O-acyl), $C_2$-$C_{24}$ alkoxycarbonyl (—(CO)—O-alkyl), $C_6$-$C_{20}$ aryloxycarbonyl (—(CO)—O-aryl), $C_2$-$C_{24}$ alkylcarbonato (—O—(CO)—O-alkyl), $C_6$-$C_{20}$ arylcarbonato (—O—(CO)—O-aryl), carboxy (—COOH), carboxylato (—COO—), carbamoyl (—(CO)—$NH_2$), mono-($C_1$-$C_{24}$ alkyl)-substituted carbamoyl (—(CO)—NH($C_1$-$C_{24}$ alkyl)), di-($C_1$-$C_4$ alkyl)-substituted carbamoyl (—(CO)—N($C_1$-$C_{24}$ alkyl)$_2$), mono-substituted arylcarbamoyl (—(CO)—NH-aryl), thiocarbamoyl (—(CS)—$NH_2$), carbamido (—NH—(CO)—$NH_2$), cyano (—CN), isocyano (—$N^+C$—), cyanato (—O—CN), isocyanato (—$ON^+C$—), isothiocyanato (—S—CN), azido (—N=$N^+$=N—), formyl (—(CO)—H), thioformyl (—(CS)—H), amino (—$NH_2$), mono- and di-($C_1$-$C_{24}$ alkyl)-substituted amino, mono- and di-($C_5$-$C_{20}$ aryl)-substituted amino, $C_2$-$C_{24}$ alkylamido (—NH—(CO)-alkyl), $C_6$-$C_{20}$ arylamido (—NH—(CO)-aryl), imino (—CR=NH where R=hydrogen, $C_1$-$C_{24}$ alkyl, $C_5$-$C_{20}$ aryl, $C_6$-$C_{24}$ alkaryl, $C_6$-$C_{24}$ aralkyl, etc.), alkylimino (—CR=N(alkyl), where R=hydrogen, alkyl, aryl, alkaryl, etc.), arylimino (—CR=N (aryl), where R=hydrogen, alkyl, aryl, alkaryl, etc.), nitro (—$NO_2$), nitroso (—NO), sulfo (—$SO_2$—OH), sulfonato (—$SO_2$—O—), $C_1$-$C_{24}$ alkylsulfanyl (—S-alkyl; also termed "alkylthio"), arylsulfanyl (—S-aryl; also termed "arylthio"), $C_1$-$C_{24}$ alkylsulfinyl (—(SO)-alkyl), $C_5$-$C_{20}$ arylsulfinyl (—(SO)-aryl), $C_1$-$C_{24}$ alkylsulfonyl (—$SO_2$-alkyl), $C_5$-$C_{20}$ arylsulfonyl (—$SO_2$-aryl), phosphono (—P(O)(OH)$_2$), phosphonato (—P(O)(O—)$_2$), phosphinato (—P(O)(O—)), phospho (—$PO_2$), and phosphino (—$PH_2$); and the hydrocarbyl moieties $C_1$-$C_{24}$ alkyl, $C_2$-$C_{24}$ alkenyl, $C_2$-$C_{24}$ alkynyl, $C_5$-$C_{20}$ aryl, $C_6$-$C_{24}$ alkaryl, and $C_6$-$C_{24}$ aralkyl.

In addition, the aforementioned functional groups may, if a particular group permits, be further substituted with one or more additional functional groups or with one or more hydrocarbyl moieties such as those specifically enumerated above. Analogously, the above-mentioned hydrocarbyl moieties may be further substituted with one or more functional groups or additional hydrocarbyl moieties such as those specifically enumerated.

When the term "substituted" appears prior to a list of possible substituted groups, it is intended that the term apply to every member of that group. For example, the phrase "substituted alkyl, alkenyl, and aryl" is to be interpreted as "substituted alkyl, substituted alkenyl, and substituted aryl." Analogously, when the term "heteroatom-containing" appears prior to a list of possible heteroatom-containing groups, it is intended that the term apply to every member of that group. For example, the phrase "heteroatom-containing alkyl, alkenyl, and aryl" is to be interpreted as "heteroatom-containing alkyl, substituted alkenyl, and substituted aryl.

"Optional" or "optionally" means that the subsequently described circumstance may or may not occur, so that the description includes instances where the circumstance occurs and instances where it does not. For example, the phrase "optionally substituted" means that a non-hydrogen substituent may or may not be present on a given atom, and, thus, the description includes structures wherein a non-hydrogen substituent is present and structures wherein a non-hydrogen substituent is not present.

The terms "stable compound" and "stable structure" are meant to indicate a compound that is sufficiently robust to survive isolation, and as appropriate, purification from a reaction mixture, and formulation into an efficacious therapeutic agent.

The terms "free compound" is used herein to describe a compound in the unbound state.

Throughout the description, where compositions are described as having, including, or comprising, specific components, it is contemplated that compositions also consist essentially of, or consist of, the recited components. Similarly, where methods or processes are described as having, including, or comprising specific process steps, the processes also consist essentially of, or consist of, the recited processing steps. Further, it should be understood that the order of steps or order for performing certain actions is immaterial so long as the compositions and methods described herein remains operable. Moreover, two or more steps or actions can be conducted simultaneously.

The term "small molecule" is an art-recognized term. In certain embodiments, this term refers to a molecule, which has a molecular weight of less than about 2000 amu, or less than about 1000 amu, and even less than about 500 amu.

All percentages and ratios used herein, unless otherwise indicated, are by weight.

The term "neoplasm" refers to any abnormal mass of cells or tissue as a result of neoplasia. The neoplasm may be benign, potentially malignant (precancerous), or malignant (cancerous). An adenoma is an example of a neoplasm.

As used herein, the phrase "therapeutically- or pharmaceutically-effective amount" as applied to the disclosed compositions refers to the amount of composition sufficient to induce a desired biological result. That result can be alleviation of the signs, symptoms, or causes of a disease, or any other desired alteration of a biological system. For example, the result can involve a decrease and/or reversal of cancerous cell growth.

As used herein, the terms "inhibit", "inhibiting", or "inhibition" includes any measurable reproducible substantial reduction in the interaction between Bcl-2 and $IP_3R$, cancer, or any other activities Bcl-2 may mediate. A substantial reduction is a "reproducible", i.e., consistently observed, reduction in binding.

Embodiments described herein relate to therapeutic compounds, pharmaceutical compositions comprising the compounds, the use of the compounds in methods of inhibiting Bcl-2 binding to inositol 1,4,5-triphosphate receptors ($IP_3R$), and to the use of the compounds derived from the Bcl-2 binding domain of $IP_3R$ in methods of inducing apoptosis in cells expressing Bcl-2 and $IP_3R$, particularly to inducing apoptosis in neoplastic cells (e.g., cancer cells, such as chronic lymphocytic leukemia or multiple myeloma) expressing Bcl-2 and $IP_3R$.

Bcl-2 interacts directly with the activation coupling domain of $IP_3R$. The coupling domain is necessary to keep the $IP_3R$ channel closed and regulates the activity of $IP_3R$ by binding to regulatory proteins. By binding to this region, Bcl-2 exerts its regulatory effect on $IP_3$-mediated $Ca^{2+}$ signals. Compounds derived from the specific Bcl-2-interacting domain of $IP_3R$, such as a BH4 domain binding peptide, can mimic $IP_3R$'s binding effect and when administered to a neoplastic cell expressing Bcl-2 and $IP_3R$ induce apoptosis and/or necrosis in the neoplastic cell. For example, the Bcl-2-$IP_3R$ interaction inhibitor BIRD-2 (Bcl-2-$IP_3R$ interaction Disrupter-2) is a synthetic BH4 domain binding peptide derived from the Bcl-2 binding site on the $IP_3R$ (See FIG. 2).

Compounds or therapeutic agents described herein, which are capable of binding to the BH4 domain of Bcl-2 and mimicking the Bcl-2-$IP_3R$ interaction inhibitory action of BIRD-2 (i.e., a BIRD-2 mimetic agent) to induce apoptosis in neoplastic cell expressing Bcl-2 and $IP_3R$, such as multiple myeloma cells and primary human Chronic lymphocytic leukemia (CLL) cells, can be identified using high throughput screening and in vitro assays, described in the Example below.

The compounds or therapeutic agents described herein can be any small chemical molecule or compound that can inhibit binding of Bcl-2 and $IP_3R$. Typically, test compounds will be small chemical molecules, natural products, or peptides. The assays are designed to screen large chemical libraries by automating the assay steps and providing compounds from any convenient source to assays, which are typically run in parallel (e.g., in microtiter formats on microtiter plates in robotic assays).

In some embodiments, the compound can be derived from the Bcl-2 binding domain of $IP_3R$. The Bcl-2 binding domain of $IP_3R$ can include, for example, the BH4 binding domain of $IP_3R$. In some aspects, the compound can include a BIRD-2 mimetic agent. In other aspects, the compound can include a non-peptidic low molecular weight BIRD-2 mimetic agent.

In some embodiments, the compound or inhibitor of Bcl-2 binding to $IP_3R$ can be a compound with the following general formula (I):

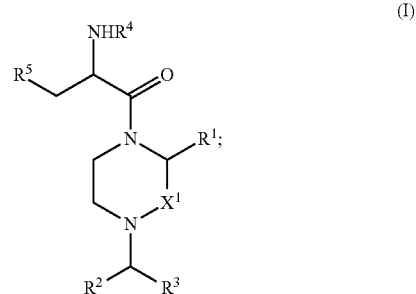

wherein $X^1$ is $CH_2$, or $C=O$;

$R^1$, $R^2$, $R^3$, $R^4$, and $R^5$ are the same or different and are independently selected from the group consisting of hydrogen, substituted or unsubstituted $C_1$-$C_{24}$ alkyl, $C_2$-$C_{24}$ alkenyl, $C_2$-$C_{24}$ alkynyl, $C_3$-$C_{20}$ aryl, heterocycloalkenyl containing from 5-7 ring atoms, (wherein from 1-3 of the ring atoms is independently selected from N, NH, N($C_1$-$C_6$ alkyl), NC(O) ($C_1$-$C_6$ alkyl), O, and S), heteroaryl or heterocyclyl containing from 5-14 ring atoms, (wherein from 1-6 of the ring atoms is independently selected from N, NH, N($C_1$-$C_3$ alkyl), O, and S), $C_6$-$C_{24}$ alkaryl, $C_6$-$C_{24}$ aralkyl, halo, silyl, hydroxyl, sulfhydryl, $C_1$-$C_{24}$ alkoxy, $C_2$-$C_{24}$ alkenyloxy, $C_2$-$C_{24}$ alkynyloxy, $C_5$-$C_{20}$ aryloxy, acyl (including $C_2$-$C_{24}$ alkylcarbonyl (—CO-alkyl) and $C_6$-$C_{20}$ arylcarbonyl (—CO-aryl)), acyloxy (—O-acyl), $C_2$-$C_{24}$ alkoxycarbonyl (—(CO)—O-alkyl), $C_6$-$C_{20}$ aryloxycarbonyl (—(CO)—O-aryl), $C_2$-$C_{24}$ alkylcarbonato (—O—(CO)—O-alkyl), $C_6$-$C_{20}$ arylcarbonato (—O—(CO)—O-aryl), carboxy (—COOH), carboxylato (—COO—), carbamoyl (—(CO)—$NH_2$), $C_1$-$C_{24}$ alkyl-carbamoyl (—(CO)—NH($C_1$-$C_{24}$ alkyl)), arylcarbamoyl (—(CO)—NH-aryl), thiocarbamoyl (—(CS)—$NH_2$), carbamido (—NH—(CO)—$NH_2$), cyano(—CN), isocyano (—$N^+C$—), cyanato (—O—CN), isocyanato (—O—$N^+$=C—), isothiocyanato (—S—CN), azido (—N=$N^+$=N—), formyl (—(CO)—H), thioformyl (—(CS)—H), amino (—$NH_2$), $C_1$-$C_{24}$ alkyl amino, $C_5$-$C_{20}$ aryl amino, $C_2$-$C_{24}$ alkylamido (—NH—(CO)-alkyl), $C_6$-$C_{20}$ arylamido (—NH—(CO)-aryl), sulfanamido (—$SO_2$N(R)$_2$ where R is independently H, alkyl, aryl or heteroaryl), imino (—CR=NH where R is hydrogen, $C_1$-$C_{24}$ alkyl, $C_5$-$C_{20}$ aryl, $C_6$-$C_{24}$ alkaryl, $C_6$-$C_{24}$ aralkyl, etc.), alkylimino (—CR=N(alkyl), where R=hydrogen, alkyl, aryl, alkaryl, aralkyl, etc.), arylimino (—CR=N(aryl), where R=hydrogen, alkyl, aryl, alkaryl, etc.), nitro (—$NO_2$), nitroso (—NO), sulfo (—$SO_2$—OH), sulfonato (—$SO_2$—O—), $C_1$-$C_{24}$ alkylsulfanyl (—S-alkyl; also termed "alkylthio"), arylsulfanyl (—S-aryl; also termed "arylthio"), $C_1$-$C_{24}$ alkylsulfinyl (—(SO)-alkyl), $C_5$-$C_{20}$ arylsulfinyl (—(SO)-aryl), $C_1$-$C_{24}$ alkylsulfonyl (—$SO_2$-alkyl), $C_5$-$C_{20}$ arylsulfonyl (—$SO_2$-aryl), sulfonamide (—$SO_2$—$NH_2$, —$SO_2NY_2$ (wherein Y is independently H, arlyl or alkyl), phosphono (—P(O)(OH)$_2$), phosphonato (—P(O)(O$^-$)$_2$), phosphinato (—P(O)(O—)), phospho (—$PO_2$), phosphino (—$PH_2$), polyalkyl ethers (—[(CH$_2$)$_n$O]$_m$), phosphates, phosphate esters [—OP(O)(OR)$_2$ where R=H, methyl or other alkyl], groups incorporating amino acids or other moieties expected to bear positive or negative charge at physiological pH, and combinations thereof; and pharmaceutically acceptable salts thereof.

In other embodiments, the inhibitor of Bcl-2 binding to IP$_3$R can be a compound with the following general formula (II):

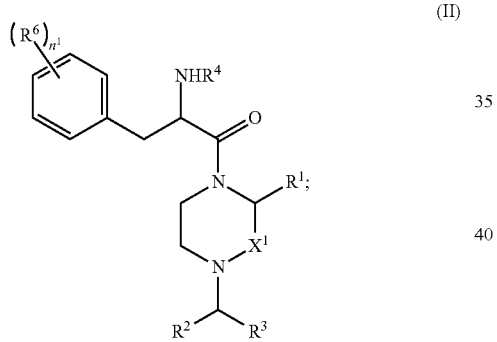

(II)

wherein $X^1$ is $CH_2$, or C=O;

$R^1$, $R^2$, $R^3$, and $R^4$ are the same or different and are independently selected from the group consisting of hydrogen, substituted or unsubstituted $C_1$-$C_{24}$ alkyl, $C_2$-$C_{24}$ alkenyl, $C_2$-$C_{24}$ alkynyl, $C_3$-$C_{20}$ aryl, heterocycloalkenyl containing from 5-7 ring atoms, (wherein from 1-3 of the ring atoms is independently selected from N, NH, N($C_1$-$C_6$ alkyl), NC(O) ($C_1$-$C_6$ alkyl), O, and S), heteroaryl or heterocyclyl containing from 5-14 ring atoms, (wherein from 1-6 of the ring atoms is independently selected from N, NH, N($C_1$-$C_3$ alkyl), O, and S), $C_6$-$C_{24}$ alkaryl, $C_6$-$C_{24}$ aralkyl, halo, silyl, hydroxyl, sulfhydryl, $C_1$-$C_{24}$ alkoxy, $C_2$-$C_{24}$ alkenyloxy, $C_2$-$C_{24}$ alkynyloxy, $C_5$-$C_{20}$ aryloxy, acyl (including $C_2$-$C_{24}$ alkylcarbonyl (—CO-alkyl) and $C_6$-$C_{20}$ arylcarbonyl (—CO-aryl)), acyloxy (—O-acyl), $C_2$-$C_{24}$ alkoxycarbonyl (—(CO)—O-alkyl), $C_6$-$C_{20}$ aryloxycarbonyl (—(CO)—O-aryl), $C_2$-$C_{24}$ alkylcarbonato (—O—(CO)—O-alkyl), $C_6$-$C_{20}$ arylcarbonato (—O—(CO)—O-aryl), carboxy (—COOH), carboxylato (—COO—), carbamoyl (—(CO)—$NH_2$), $C_1$-$C_{24}$ alkyl-carbamoyl (—(CO)—NH($C_1$-$C_{24}$ alkyl)), arylcarbamoyl (—(CO)—NH-aryl), thiocarbamoyl (—(CS)—$NH_2$), carbamido (—NH—(CO)—$NH_2$), cyano(—CN), isocyano (—N$^+$C—), cyanato (—O—CN), isocyanato (—O—N$^+$=C—), isothiocyanato (—S—CN), azido (—N=N$^+$=N—), formyl (—(CO)—H), thioformyl (—(CS)—H), amino (—$NH_2$), $C_1$-$C_{24}$ alkyl amino, $C_5$-$C_{20}$ aryl amino, $C_2$-$C_{24}$ alkylamido (—NH—(CO)-alkyl), $C_6$-$C_{20}$ arylamido (—NH—(CO)-aryl), sulfanamido (—$SO_2$N(R)$_2$ where R is independently H, alkyl, aryl or heteroaryl), imino (—CR=NH where R is hydrogen, $C_1$-$C_{24}$ alkyl, $C_5$-$C_{20}$ aryl, $C_6$-$C_{24}$ alkaryl, $C_6$-$C_{24}$ aralkyl, etc.), alkylimino (—CR=N(alkyl), where R=hydrogen, alkyl, aryl, alkaryl, aralkyl, etc.), arylimino (—CR=N(aryl), where R=hydrogen, alkyl, aryl, alkaryl, etc.), nitro (—$NO_2$), nitroso (—NO), sulfo (—$SO_2$—OH), sulfonato (—$SO_2$—O—), $C_1$-$C_{24}$ alkylsulfanyl (—S-alkyl; also termed "alkylthio"), arylsulfanyl (—S-aryl; also termed "arylthio"), $C_1$-$C_{24}$ alkylsulfinyl (—(SO)-alkyl), $C_5$-$C_{20}$ arylsulfinyl (—(SO)-aryl), $C_1$-$C_{24}$ alkylsulfonyl (—$SO_2$-alkyl), $C_5$-$C_{20}$ arylsulfonyl (—$SO_2$-aryl), sulfonamide (—$SO_2$—$NH_2$, —$SO_2NY_2$ (wherein Y is independently H, arlyl or alkyl), phosphono (—P(O)(OH)$_2$), phosphonato (—P(O)(O—)$_2$), phosphinato (—P(O)(O—)), phospho (—$PO_2$), phosphino (—$PH_2$), polyalkyl ethers (—[(CH$_2$)$_n$O]$_m$), phosphates, phosphate esters [—OP(O)(OR)$_2$ where R=H, methyl or other alkyl], groups incorporating amino acids or other moieties expected to bear positive or negative charge at physiological pH, and combinations thereof;

$R^6$ is a halo (e.g., Br, Cl, or F), $n^1$ is 0-3, and pharmaceutically acceptable salts thereof.

In other embodiments, the inhibitor of Bcl-2 binding to IP$_3$R can be a compound with the following general formula (III):

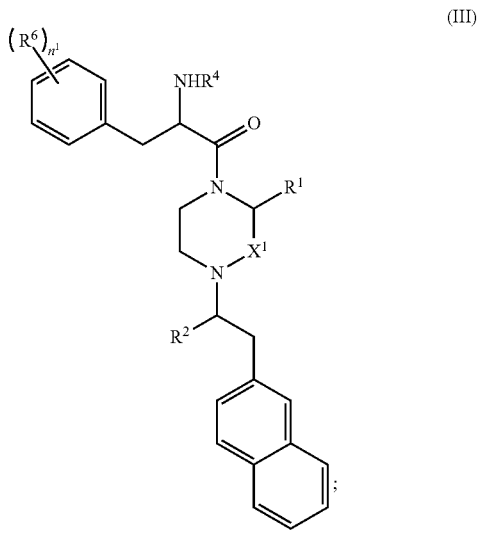

(III)

wherein $X^1$ is $CH_2$, or C=O;

$R^1$, $R^2$, and $R^4$ are the same or different and are independently selected from the group consisting of hydrogen, substituted or unsubstituted $C_1$-$C_{24}$ alkyl, $C_2$-$C_{24}$ alkenyl, $C_2$-$C_{24}$ alkynyl, $C_3$-$C_{20}$ aryl, heterocycloalkenyl containing from 5-7 ring atoms, (wherein from 1-3 of the ring atoms is independently selected from N, NH, N(C$_1$-C$_6$ alkyl), NC(O) (C$_1$-C$_6$ alkyl), O, and S), heteroaryl or heterocyclyl containing from 5-14 ring atoms, (wherein from 1-6 of the ring atoms is independently selected from N, NH, N(C$_1$-C$_3$ alkyl), O, and S), C$_6$-C$_{24}$ alkaryl, C$_6$-C$_{24}$ aralkyl, halo, silyl, hydroxyl, sulfhydryl, C$_1$-C$_{24}$ alkoxy, C$_2$-C$_{24}$ alkenyloxy, C$_2$-C$_{24}$ alkynyloxy, C$_5$-C$_{20}$ aryloxy, acyl (including C$_2$-C$_{24}$ alkylcarbonyl (—CO-alkyl) and C$_6$-C$_{20}$ arylcarbonyl (—CO-aryl)), acyloxy (—O-acyl), C$_2$-C$_{24}$ alkoxycarbonyl (—(CO)—O-alkyl), C$_6$-C$_{20}$ aryloxycarbonyl (—(CO)—O-aryl), C$_2$-C$_{24}$ alkylcarbonato (—O—(CO)—O-alkyl), C$_6$-C$_{20}$ arylcarbonato (—O—(CO)—O-aryl), carboxy (—COOH), carboxylato (—COO—), carbamoyl (—(CO)—NH$_2$), C$_1$-C$_{24}$ alkyl-carbamoyl (—(CO)—NH(C$_1$-C$_{24}$ alkyl)), arylcarbamoyl (—(CO)—NH-aryl), thiocarbamoyl (—(CS)—NH$_2$), carbamido (—NH—(CO)—NH$_2$), cyano(—CN), isocyano (—N$^+$C—), cyanato (—O—CN), isocyanato (—O—N$^+$=C—), isothiocyanato (—S—CN), azido (—N=N$^+$=N—), formyl (—(CO)—H), thioformyl (—(CS)—H), amino (—NH$_2$), C$_1$-C$_{24}$ alkyl amino, C$_5$-C$_{20}$ aryl amino, C$_2$-C$_{24}$ alkylamido (—NH—(CO)-alkyl), C$_6$-C$_{20}$ arylamido (—NH—(CO)-aryl), sulfanamido (—SO$_2$N(R)$_2$ where R is independently H, alkyl, aryl or heteroaryl), imino (—CR=NH where R is hydrogen, C$_1$-C$_{24}$ alkyl, C$_5$-C$_{20}$ aryl, C$_6$-C$_{24}$ alkaryl, C$_6$-C$_{24}$ aralkyl, etc.), alkylimino (—CR=N(alkyl), where R=hydrogen, alkyl, aryl, alkaryl, aralkyl, etc.), arylimino (—CR=N(aryl), where R=hydrogen, alkyl, aryl, alkaryl, etc.), nitro (—NO$_2$), nitroso (—NO), sulfo (—SO$_2$—OH), sulfonato (—SO$_2$—O—), C$_1$-C$_{24}$ alkylsulfanyl (—S-alkyl; also termed "alkylthio"), arylsulfanyl (—S-aryl; also termed "arylthio"), C$_1$-C$_{24}$ alkylsulfinyl (—(SO)-alkyl), C$_5$-C$_{20}$ arylsulfinyl (—(SO)-aryl), C$_1$-C$_{24}$ alkylsulfonyl (—SO$_2$-alkyl), C$_5$-C$_{20}$ arylsulfonyl (—SO$_2$-aryl), sulfonamide (—SO$_2$—NH$_2$, —SO$_2$NY$_2$ (wherein Y is independently H, arlyl or alkyl), phosphono (—P(O)(OH)$_2$), phosphonato (—P(O)(O—)$_2$), phosphinato (—P(O)(O—)), phospho (—PO$_2$), phosphino (—PH$_2$), polyalkyl ethers (—[(CH$_2$)$_n$O]$_m$), phosphates, phosphate esters [—OP(O)(OR)$_2$ where R=H, methyl or other alkyl], groups incorporating amino acids or other moieties expected to bear positive or negative charge at physiological pH, and combinations thereof;

R$^6$ is a halo (e.g., Br, Cl, or F), n$^1$ is 0-3, and pharmaceutically acceptable salts thereof.

In other embodiments, the inhibitor of Bcl-2 binding to IP$_3$R can be a compound with the following general formula (IV):

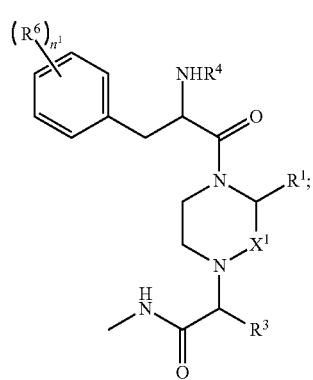

(IV)

wherein X$^1$ is CH$_2$, or C=O;

R$^1$, R$^3$, and R$^4$ are the same or different and are independently selected from the group consisting of hydrogen, substituted or unsubstituted C$_1$-C$_{24}$ alkyl, C$_2$-C$_{24}$ alkenyl, C$_2$-C$_{24}$ alkynyl, C$_3$-C$_{20}$ aryl, heterocycloalkenyl containing from 5-7 ring atoms, (wherein from 1-3 of the ring atoms is independently selected from N, NH, N(C$_1$-C$_6$ alkyl), NC(O) (C$_1$-C$_6$ alkyl), O, and S), heteroaryl or heterocyclyl containing from 5-14 ring atoms, (wherein from 1-6 of the ring atoms is independently selected from N, NH, N(C$_1$-C$_3$ alkyl), O, and S), C$_6$-C$_{24}$ alkaryl, C$_6$-C$_{24}$ aralkyl, halo, silyl, hydroxyl, sulfhydryl, C$_1$-C$_{24}$ alkoxy, C$_2$-C$_{24}$ alkenyloxy, C$_2$-C$_{24}$ alkynyloxy, C$_5$-C$_{20}$ aryloxy, acyl (including C$_2$-C$_{24}$ alkylcarbonyl (—CO-alkyl) and C$_6$-C$_{20}$ arylcarbonyl (—CO-aryl)), acyloxy (—O-acyl), C$_2$-C$_{24}$ alkoxycarbonyl (—(CO)—O-alkyl), C$_6$-C$_{20}$ aryloxycarbonyl (—(CO)—O-aryl), C$_2$-C$_{24}$ alkylcarbonato (—O—(CO)—O-alkyl), C$_6$-C$_{20}$ arylcarbonato (—O—(CO)—O-aryl), carboxy (—COOH), carboxylato (—COO—), carbamoyl (—(CO)—NH$_2$), C$_1$-C$_{24}$ alkyl-carbamoyl (—(CO)—NH(C$_1$-C$_{24}$ alkyl)), arylcarbamoyl (—(CO)—NH-aryl), thiocarbamoyl (—(CS)—NH$_2$), carbamido (—NH—(CO)—NH$_2$), cyano(—CN), isocyano (—N$^+$C—), cyanato (—O—CN), isocyanato (—O—N$^+$=C—), isothiocyanato (—S—CN), azido (—N=N$^+$=N—), formyl (—(CO)—H), thioformyl (—(CS)—H), amino (—NH$_2$), C$_1$-C$_{24}$ alkyl amino, C$_5$-C$_{20}$ aryl amino, C$_2$-C$_{24}$ alkylamido (—NH—(CO)-alkyl), C$_6$-C$_{20}$ arylamido (—NH—(CO)-aryl), sulfanamido (—SO$_2$N(R)$_2$ where R is independently H, alkyl, aryl or heteroaryl), imino (—CR=NH where R is hydrogen, C$_1$-C$_{24}$ alkyl, C$_5$-C$_{20}$ aryl, C$_6$-C$_{24}$ alkaryl, C$_6$-C$_{24}$ aralkyl, etc.), alkylimino (—CR=N(alkyl), where R=hydrogen, alkyl, aryl, alkaryl, aralkyl, etc.), arylimino (—CR=N(aryl), where R=hydrogen, alkyl, aryl, alkaryl, etc.), nitro (—NO$_2$), nitroso (—NO), sulfo (—SO$_2$—OH), sulfonato (—SO$_2$—O—), C$_1$-C$_{24}$ alkylsulfanyl (—S-alkyl; also termed "alkylthio"), arylsulfanyl (—S-aryl; also termed "arylthio"), C$_1$-C$_{24}$ alkylsulfinyl (—(SO)-alkyl), C$_5$-C$_{20}$ arylsulfinyl (—(SO)-aryl), C$_1$-C$_{24}$ alkylsulfonyl (—SO$_2$-alkyl), C$_5$-C$_{20}$ arylsulfonyl (—SO$_2$-aryl), sulfonamide (—SO$_2$—NH$_2$, —SO$_2$NY$_2$ (wherein Y is independently H, arlyl or alkyl), phosphono (—P(O)(OH)$_2$), phosphonato (—P(O)(O—)$_2$), phosphinato (—P(O)(O—)), phospho (—PO$_2$), phosphino (—PH$_2$), polyalkyl ethers (—[(CH$_2$)$_n$O]$_m$), phosphates, phosphate esters [—OP(O)(OR)$_2$ where R=H, methyl or other alkyl], groups incorporating amino acids or other moieties expected to bear positive or negative charge at physiological pH, and combinations thereof;

R$^6$ is a halo (e.g., Br, Cl, or F), n$^1$ is 0-3, and pharmaceutically acceptable salts thereof.

In some embodiments, the inhibitor of Bcl-2 binding to IP$_3$R can include a compound having the formula selected from the group consisting of:

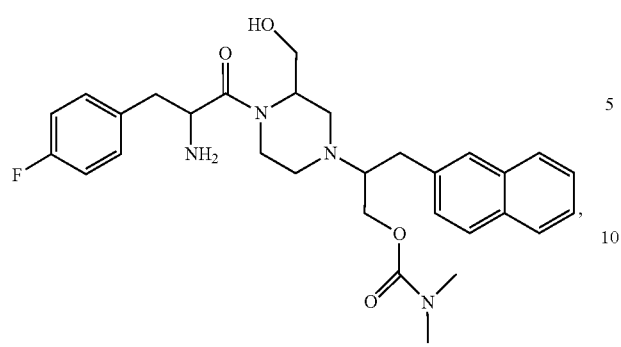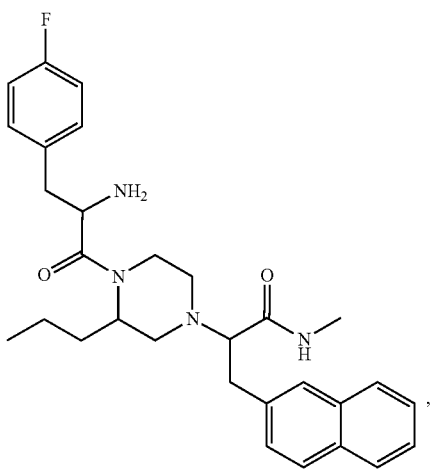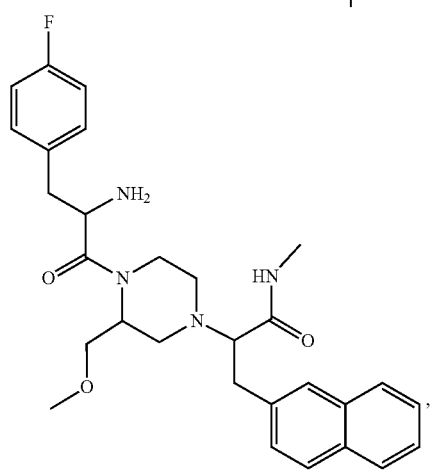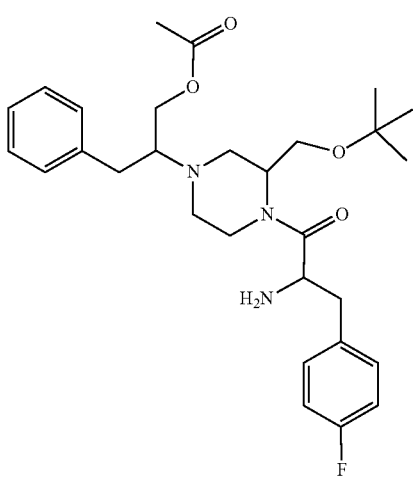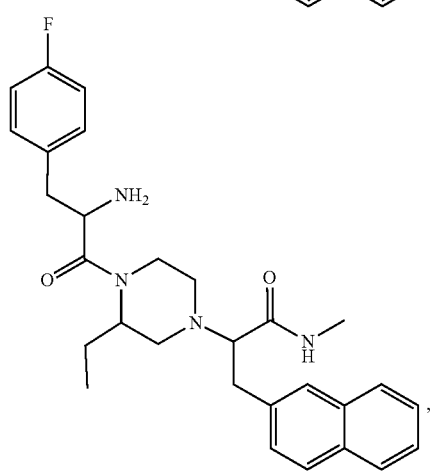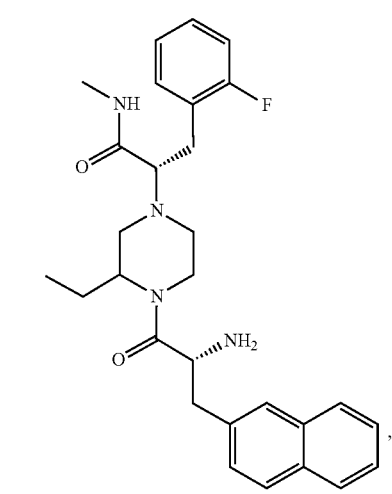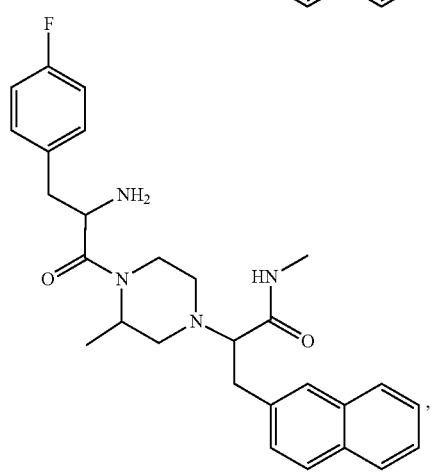

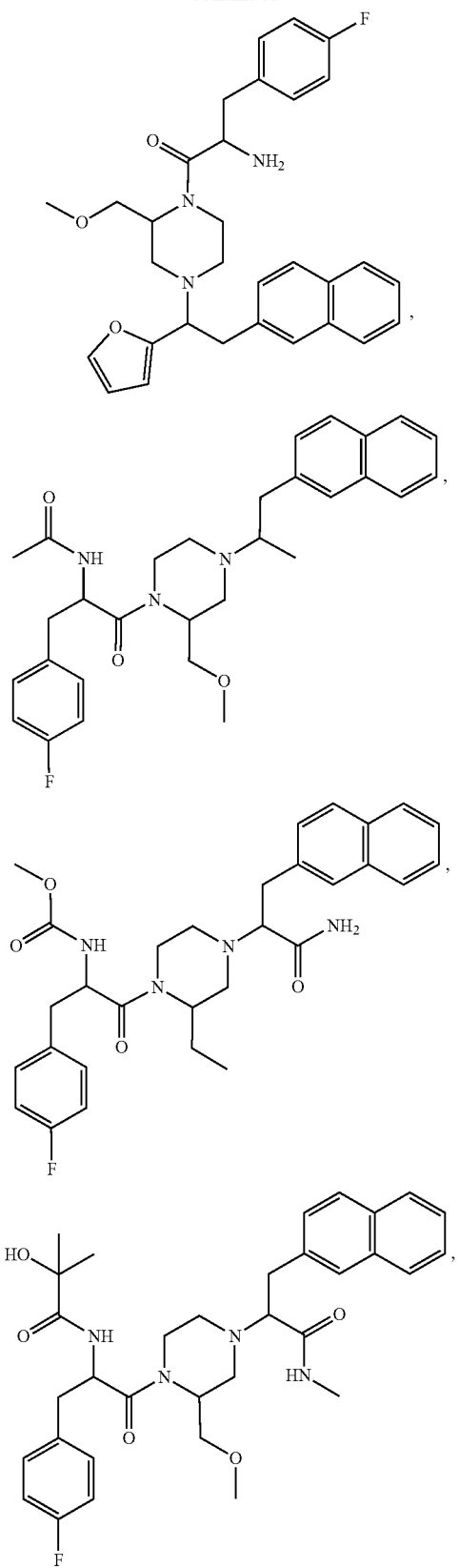
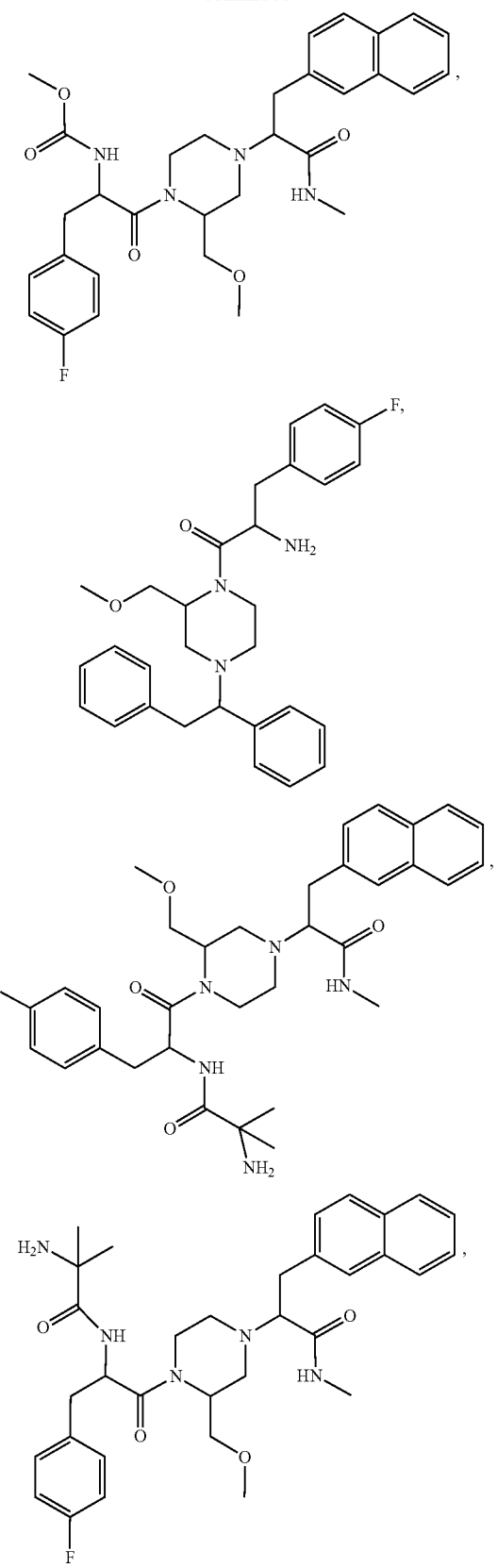

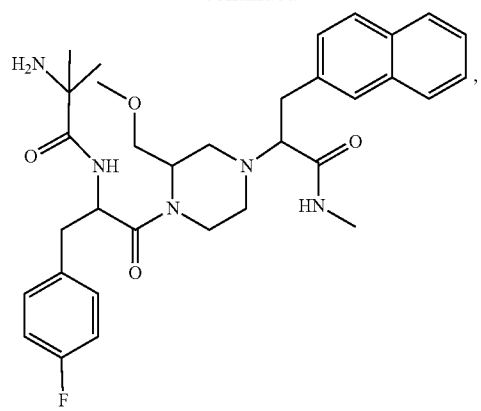
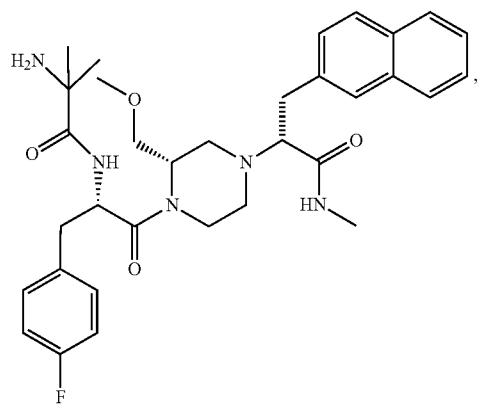
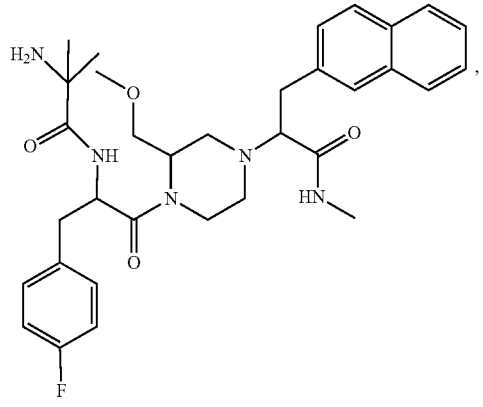
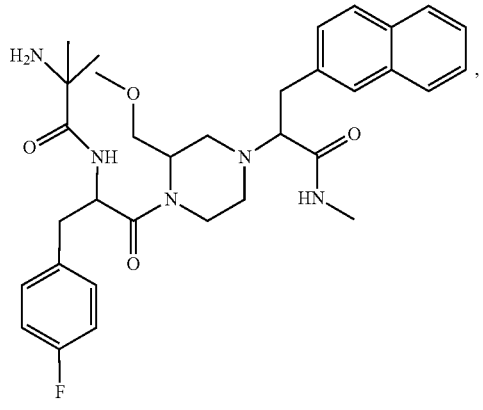
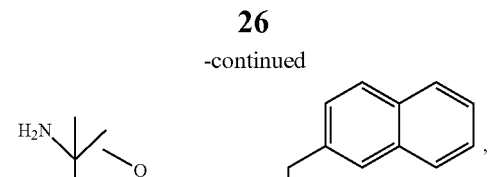
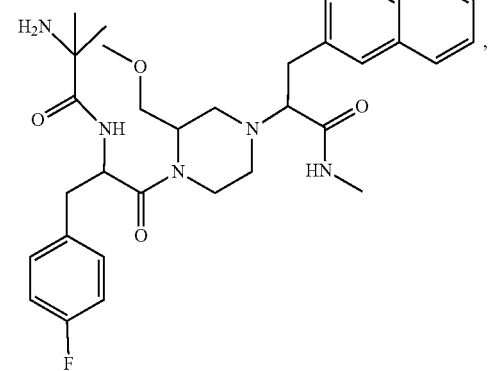
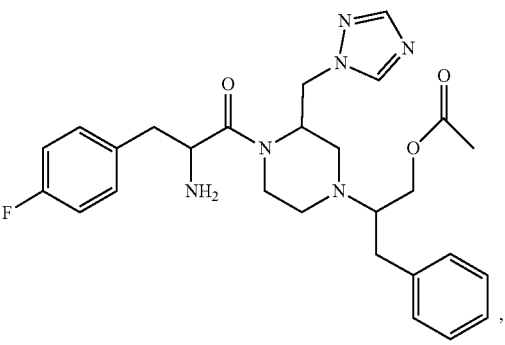
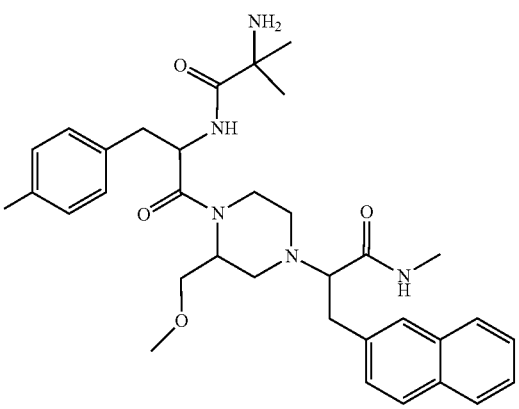
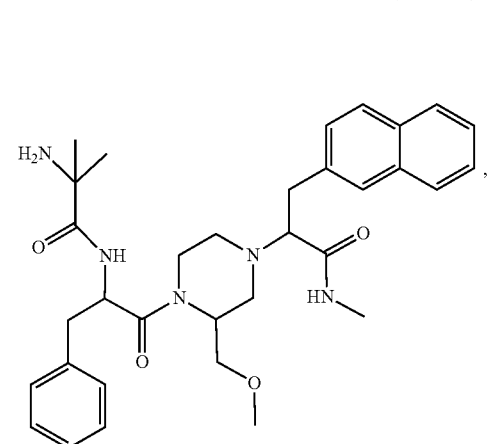

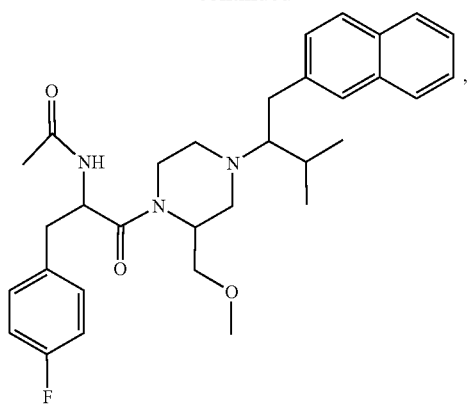
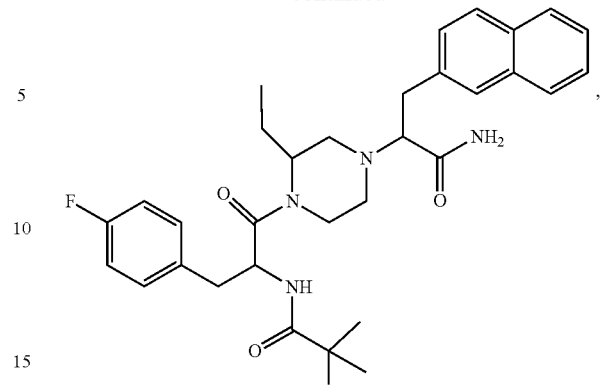
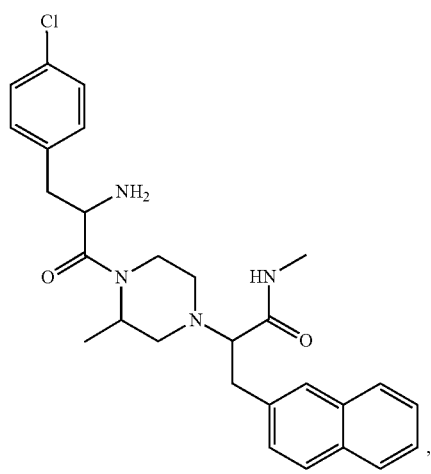
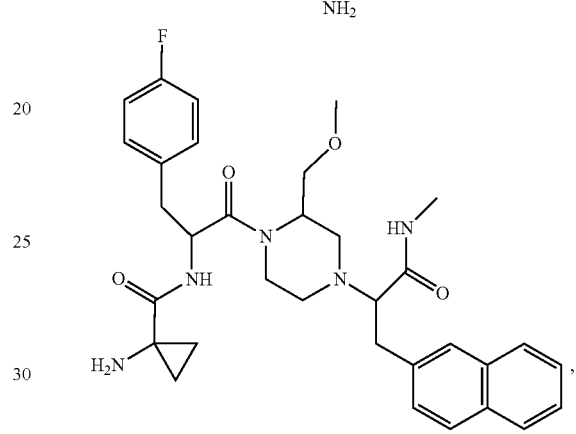
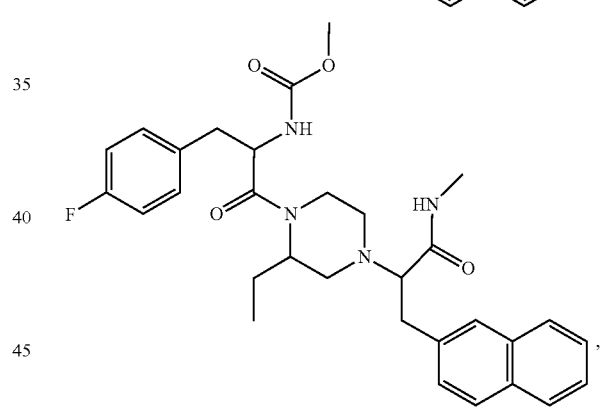
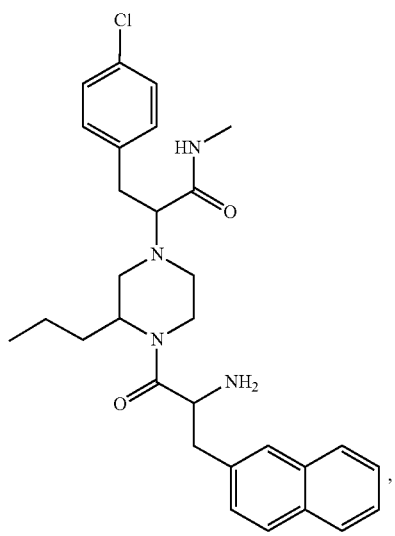
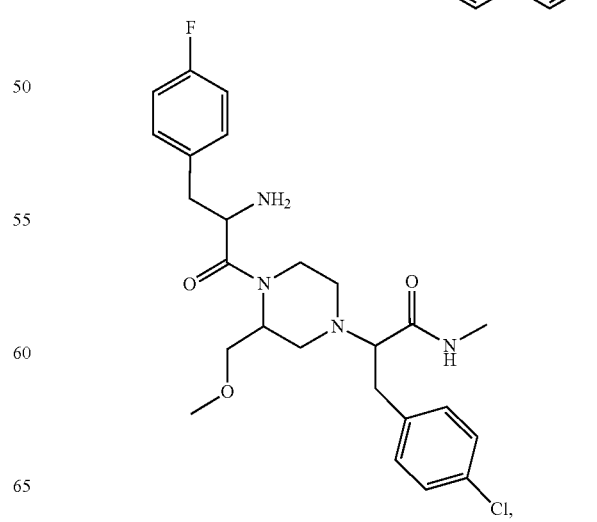

29
-continued
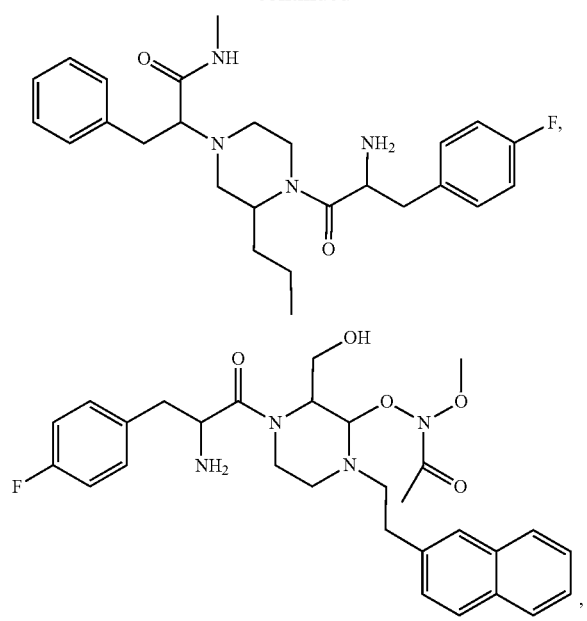
30
-continued
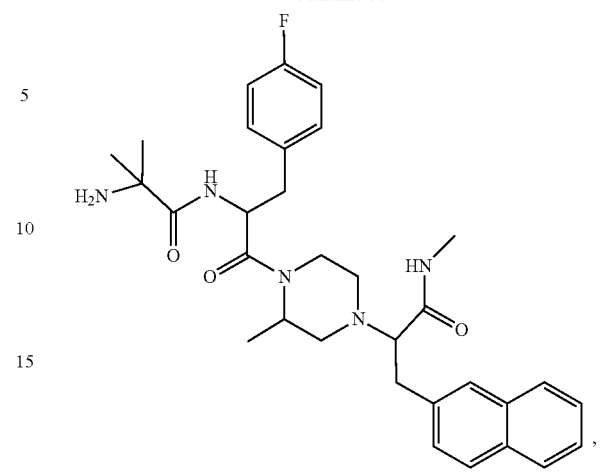
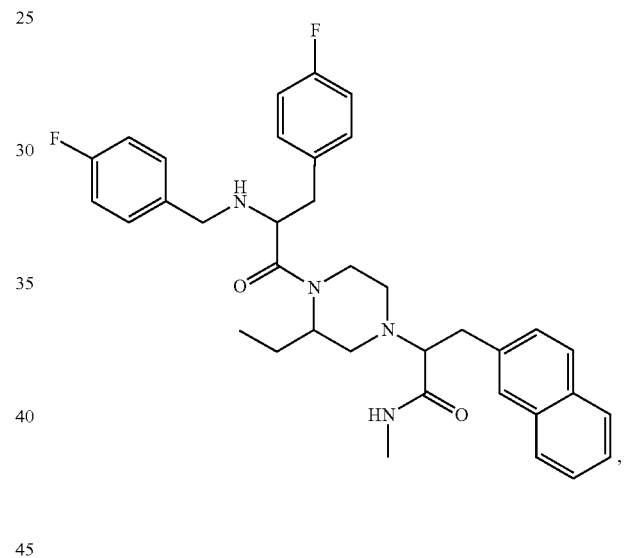
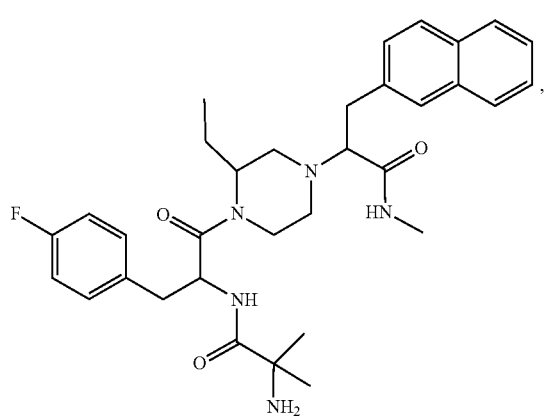
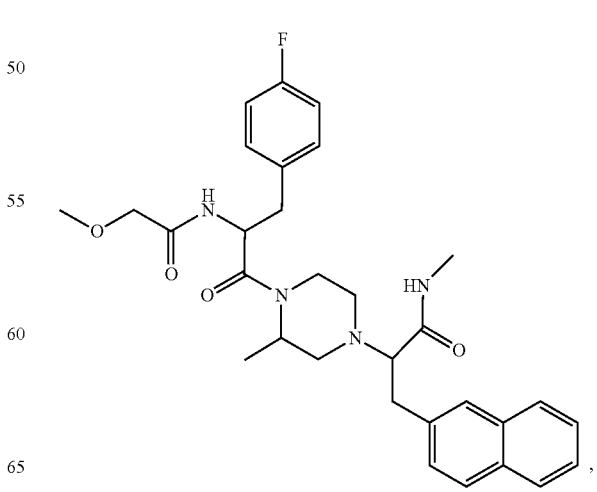

31
-continued
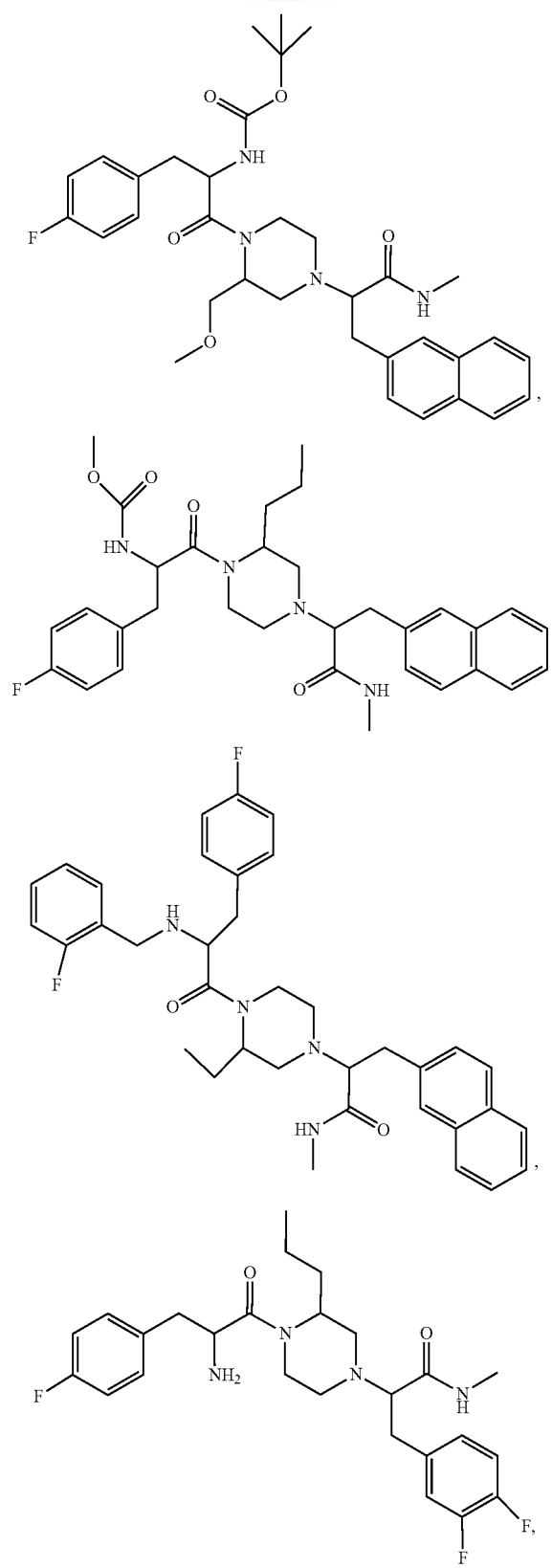
32
-continued
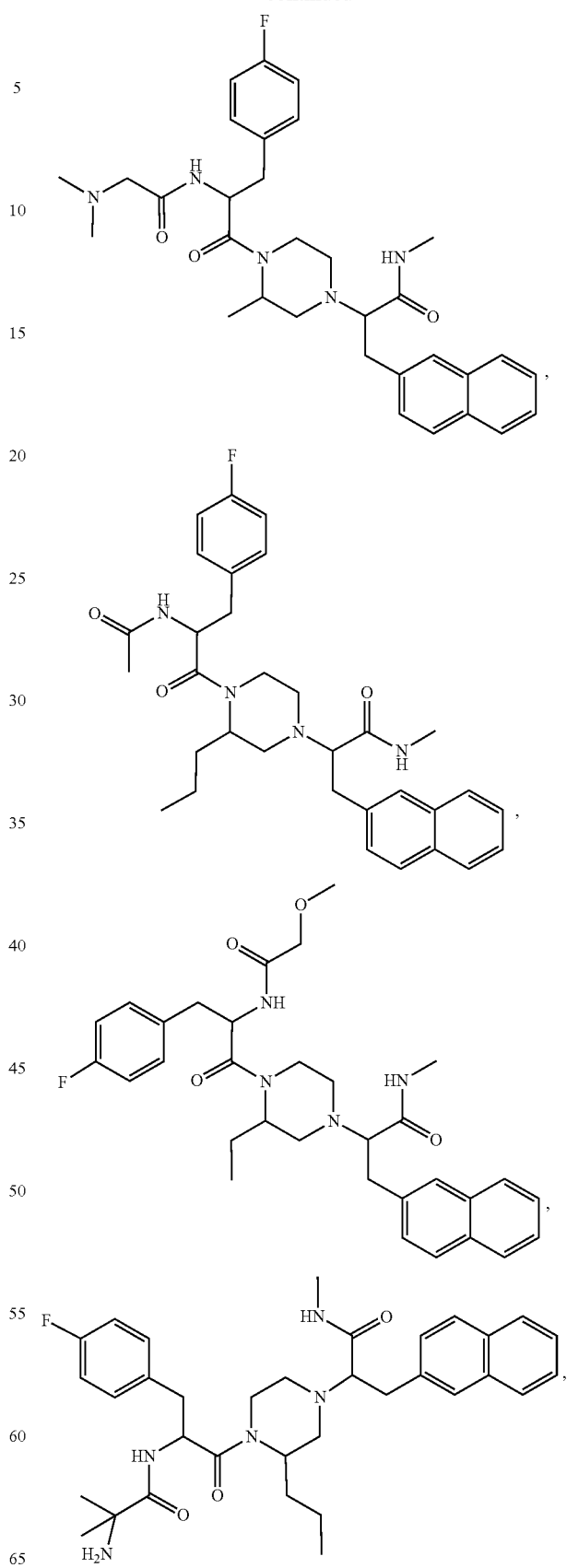

33
-continued
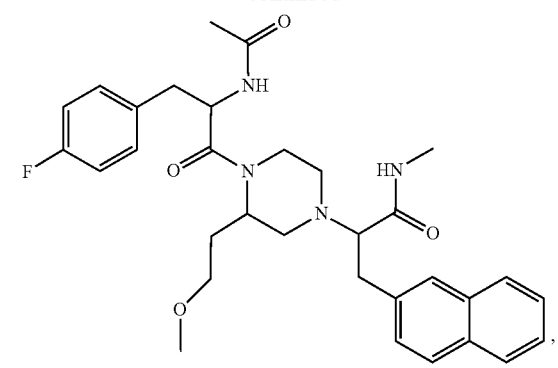
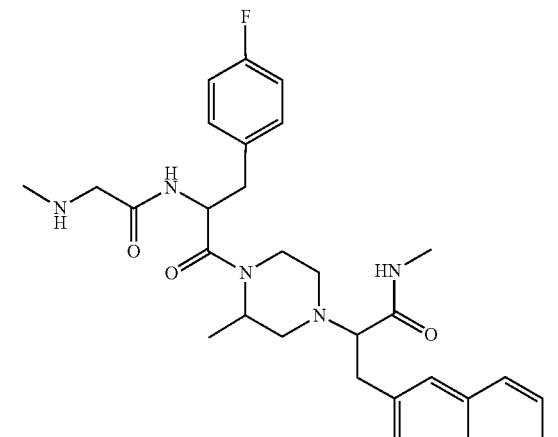
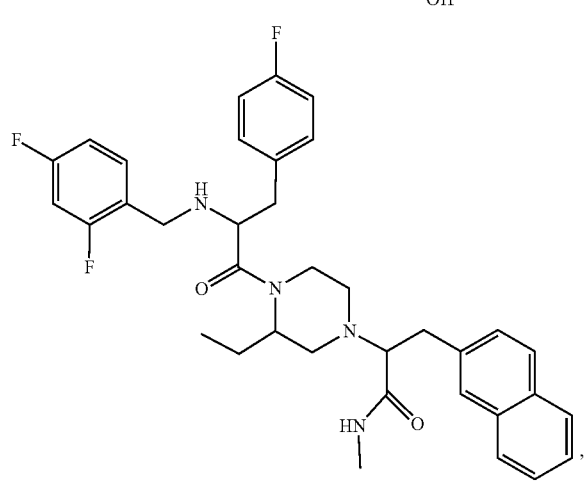
34
-continued
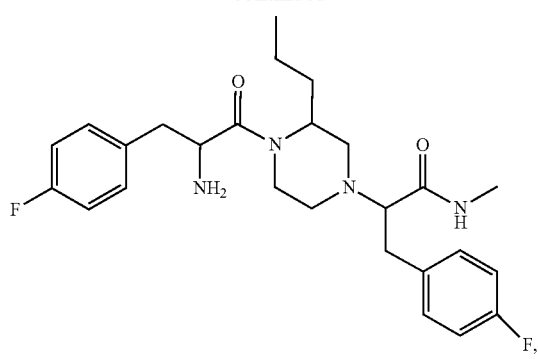
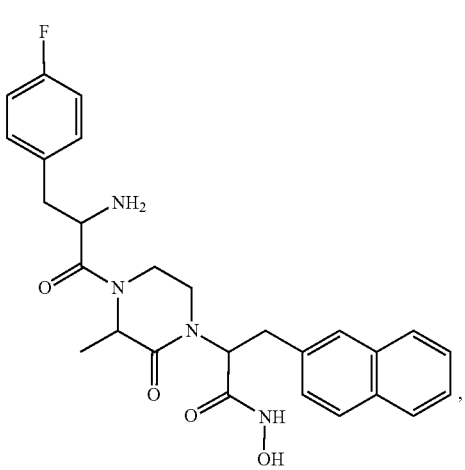
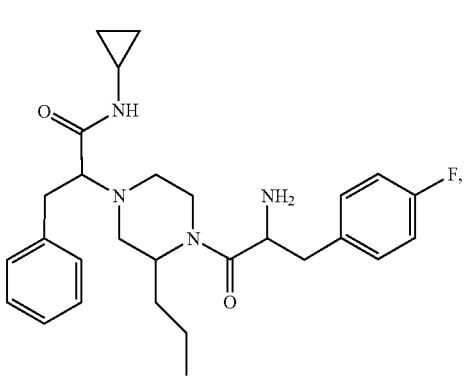

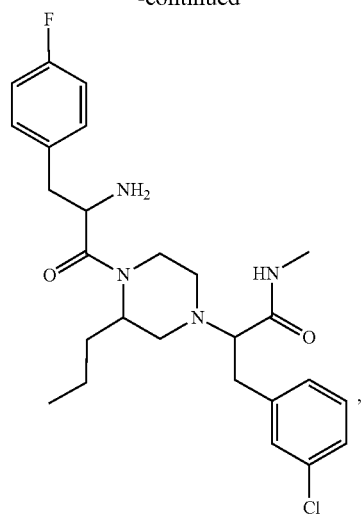
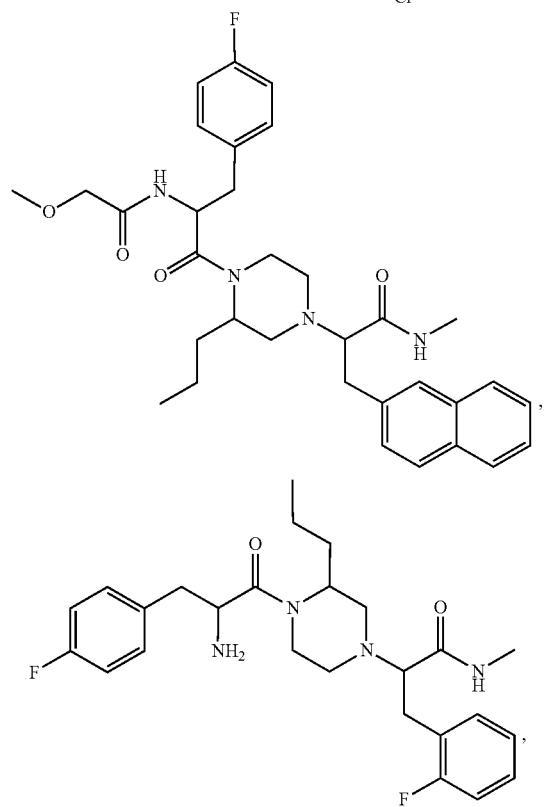
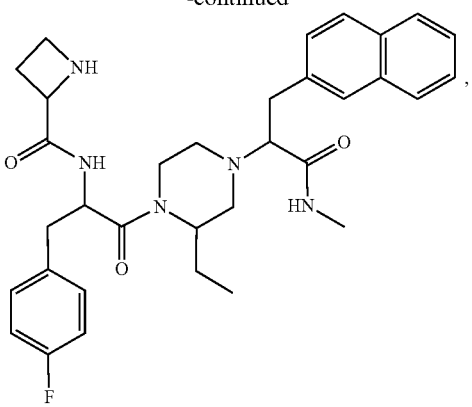
and pharmaceutically acceptable salts thereof.
In another aspect, the therapeutic agent can include compounds having the following formulas:
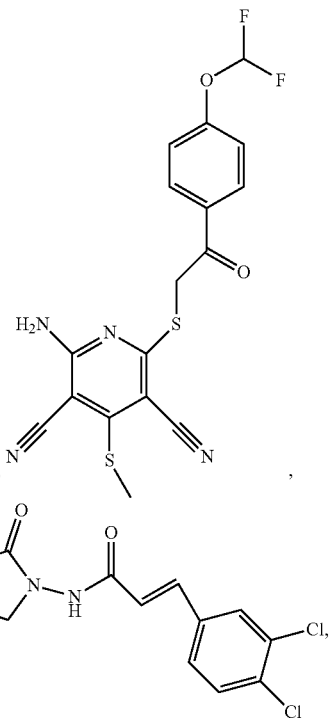
and pharmaceutically acceptable salts thereof.

In other embodiments, the inhibitor of Bcl-2 binding to IP$_3$R can include a compound having the formula:

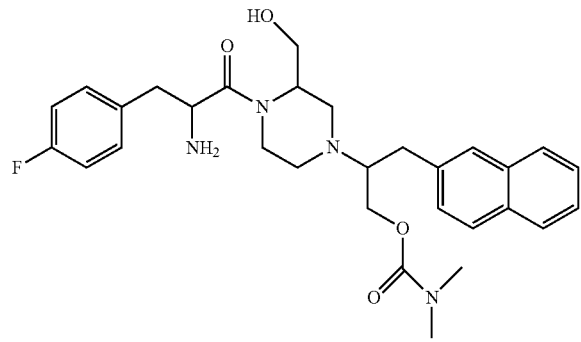 [SMILES: CN(C)C(=O)OCC(Cc1ccc2ccccc2c1)N1CCN(C(=O)C(N)Cc2ccc(F)cc2)C(CO)C1]

and pharmaceutically acceptable salts thereof.

In still other embodiments, the inhibitor of Bcl-2 binding to IP$_3$R can include a compound having the formula:

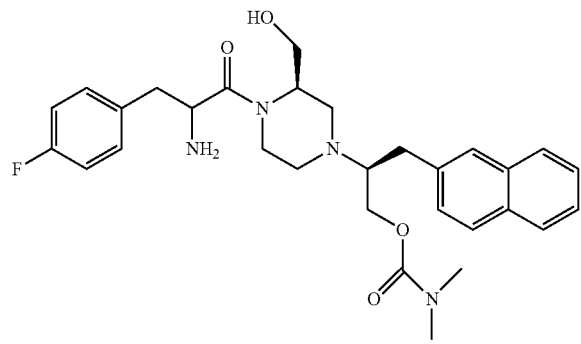 [SMILES: CN(C)C(=O)OC[C@H](Cc1ccc2ccccc2c1)N1CCN(C(=O)C(N)Cc2ccc(F)cc2)[C@@H](CO)C1]

and pharmaceutically acceptable salts thereof.

The therapeutic agents described above can be used for treatment of a disease or condition in a human where inhibition of Bcl-2-IP$_3$R interaction and thereby the induction of apoptosis, such as in human neoplastic cells that express IP$_3$R and Bcl-2 is beneficial. In some embodiments, the therapeutic agents can be used in a method of treating a neoplastic disorder in a subject. The method includes administering to neoplastic cells of the subject expressing IP$_3$R and Bcl-2 a therapeutically effective amount of a Bcl-2-IP$_3$R interaction inhibitory compound that inhibits binding of Bcl-2 to IP$_3$ receptors (IP$_3$R) of cells that express IP$_3$R and Bcl-2. The compound or therapeutic agent can be administered in association with one or more non-toxic, pharmaceutically acceptable carriers and/or diluents and/or adjuvants and if desired other active ingredients.

The compounds or therapeutic agents described herein can be used to treat conditions and diseases including but not limited to Bcl-2 associated cancers. Bcl-2 associated cancer can include cancer associated with malignant transformation of B-lymphocytes, small cell lung cancer, and pancreatic cancer. In some embodiments, Bcl-2 associated cancers associated with malignant transformation of B-lymphocytes include but are not limited to chronic lymphocytic leukemia (CLL), follicular lymphoma, diffuse large B-cell lymphoma, and multiple myeloma (MM).

In some embodiments, the therapeutic agents described herein can be used for the treatment of a Bcl-2 associated cancer that is resistant to an anti-cancer agent, such as multiple myeloma. In certain embodiments, the therapeutic agents described above can be used for the treatment of a Bcl-2 associated cancer that is resistant to the ABT class of BH-3-mimetic agents.

The therapeutic agents described herein can be provided in the form of pharmaceutical compositions. The pharmaceutical compositions can be administered to any animal that can experience the beneficial effects of the compounds of the invention. Foremost among such animals are humans, although the invention is not intended to be so limited.

The pharmaceutical compositions will generally comprise an effective amount of the Bcl-2-IP$_3$R interaction inhibitory compound, dissolved or dispersed in a pharmaceutically acceptable carrier or aqueous medium. Combined therapeutics are also contemplated, and the same type of underlying pharmaceutical compositions may be employed for both single and combined medicaments.

In addition to the pharmacologically active compounds, the pharmaceutical preparations of the compounds can contain suitable pharmaceutically acceptable carriers comprising excipients and auxiliaries that facilitate processing of the active compounds into preparations that can be used pharmaceutically. The pharmaceutical preparations can be manufactured in a manner that is, itself, known, for example, by means of conventional mixing, granulating, dragee-making, dissolving, or lyophilizing processes. Thus, pharmaceutical preparations for oral use can be obtained by combining the active compounds with solid excipients, optionally grinding the resulting mixture and processing the mixture of granules, after adding suitable auxiliaries, if desired or necessary, to obtain tablets or dragee cores.

The Bcl-2-IP$_3$R interaction inhibitory compounds will most often be formulated for parenteral administration, e.g., formulated for injection via the intravenous, intramuscular, sub-cutaneous, transdermal, or other such routes, including peristaltic administration and direct instillation into a tumor or disease site (intracavity administration). The preparation of an aqueous composition that contains such a compound as an active ingredient will be known to those of skill in the art in light of the present disclosure. Typically, such compositions can be prepared as injectables, either as liquid solutions or suspensions; solid forms suitable for using to prepare solutions or suspensions upon the addition of a liquid prior to injection can also be prepared; and the preparations can also be emulsified.

The pharmaceutical forms suitable for injectable use include sterile aqueous solutions or dispersions; formulations including sesame oil, peanut oil or aqueous propylene glycol; and sterile powders for the extemporaneous preparation of sterile injectable solutions or dispersions. In all cases, the form should be sterile and fluid to the extent that syringability exists. It should be stable under the conditions of manufacture and storage and should be preserved against the contaminating action of microorganisms, such as bacteria and fungi.

Compositions of the Bcl-2-IP$_3$R interaction inhibitory compounds can be formulated into a sterile aqueous composition in a neutral or salt form. Solutions as free base or pharmacologically acceptable salts can be prepared in water suitably mixed with a surfactant, such as hydroxypropylcellulose. Pharmaceutically acceptable salts, include the acid addition salts (formed with the free amino groups of the protein), and those that are formed with inorganic acids such as, for example, hydrochloric or phosphoric acids, or such organic acids as acetic, trifluoroacetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like.

Carriers can include solvents and dispersion media containing, for example, water, ethanol, polyol (for example, glycerol, propylene glycol, and liquid polyethylene glycol, and the like), suitable mixtures thereof, and vegetable oils. In many cases, it will be preferable to include isotonic agents, for example, sugars or sodium chloride. The proper fluidity can be maintained, for example, by the use of a coating, such as lecithin, by the maintenance of the required particle size in the case of dispersion and/or by the use of surfactants.

Under ordinary conditions of storage and use, all such preparations should contain a preservative to prevent the growth of microorganisms. The prevention of the action of microorganisms can be brought about by various antibacterial and antifungal agents, for example, parabens, chlorobutanol, phenol, sorbic acid, thimerosal, and the like. Prolonged absorption of the injectable compositions can be brought about by the use in the compositions of agents delaying absorption, for example, aluminum monostearate and gelatin.

Prior to or upon formulation, the Bcl-2-IP$_3$R interaction inhibitory compounds can be extensively dialyzed to remove undesired small molecular weight molecules, and/or lyophilized for more ready formulation into a desired vehicle, where appropriate. Sterile injectable solutions are prepared by incorporating the active agents in the required amount in the appropriate solvent with various of the other ingredients enumerated above, as desired, followed by filtered sterilization. Generally, dispersions are prepared by incorporating the various sterilized active ingredients into a sterile vehicle that contains the basic dispersion medium and the required other ingredients from those enumerated above.

Pharmaceutical compositions can generally include an amount of a Bcl-2-IP$_3$R interaction inhibitory compound admixed with an acceptable pharmaceutical diluent or excipient, such as a sterile aqueous solution, to give a range of final concentrations, depending on the intended use. The techniques of preparation are generally well known in the art as exemplified by Remington's Pharmaceutical Sciences, 16th Ed. Mack Publishing Company, 1980, incorporated herein by reference. Moreover, for human administration, preparations should meet sterility, pyrogenicity, general safety and purity standards as required by FDA Office of Biological Standards. Upon formulation, the polypeptide or conjugate solutions will be administered in a manner compatible with the dosage formulation and in such amount as is therapeutically effective.

Formulations of Bcl-2-IP$_3$R interaction inhibitory compounds are easily administered in a variety of dosage forms, such as the type of injectable solutions described above, but other pharmaceutically acceptable forms are also contemplated, e.g., tablets, pills, capsules or other solids for oral administration, suppositories, pessaries, nasal solutions or sprays, aerosols, inhalants, topical formulations, liposomal forms and the like. The type of form for administration will be matched to the disease or disorder to be treated.

Pharmaceutical "slow release" capsules or "sustained release" compositions or preparations may be used and are generally applicable. Slow release formulations are generally designed to give a constant drug level over an extended period and may be used to deliver the Bcl-2-IP$_3$R interaction inhibitory compounds in accordance with the present invention. The slow release formulations are typically implanted in the vicinity of the disease site, for example, at the site of a tumor.

Examples of sustained-release preparations include semipermeable matrices of solid hydrophobic polymers containing the polypeptide or immunoconjugate, which matrices are in the form of shaped articles, e.g., films or microcapsule. Examples of sustained-release matrices include polyesters; hydrogels, for example, poly(2-hydroxyethyl-methacrylate) or poly(vinylalcohol); polylactides, e.g., U.S. Pat. No. 3,773,919; copolymers of L-glutamic acid and 7 ethyl-L-glutamate; non-degradable ethylene-vinyl acetate; degradable lactic acid-glycolic acid copolymers, such as the LUPRON DEPOT (injectable microspheres composed of lactic acid-glycolic acid copolymer and leuprolide acetate); and poly-D-(−)-3-hydroxybutyric acid.

While polymers such as ethylene-vinyl acetate and lactic acid-glycolic acid enable release of molecules for over 100 days, certain hydrogels release proteins for shorter time periods. When encapsulated polypeptides remain in the body for a long time, they may denature or aggregate as a result of exposure to moisture at 37° C., thus reducing biological activity and/or changing immunogenicity. Rational strategies are available for stabilization depending on the mechanism involved. For example, if the aggregation mechanism involves intermolecular S—S bond formation through thio-disulfide interchange, stabilization is achieved by modifying sulfhydryl residues, lyophilizing from acidic solutions, controlling moisture content, using appropriate additives, developing specific polymer matrix compositions, and the like.

In certain embodiments, liposomes and/or nanoparticles may also be employed with the Bcl-2-IP$_3$R interaction inhibitory compounds. The formation and use of liposomes is generally known to those of skill in the art, as summarized below.

Liposomes are formed from phospholipids that are dispersed in an aqueous medium and spontaneously form multilamellar concentric bilayer vesicles (also termed multilamellar vesicles (MLVs). MLVs generally have diameters of from 25 nm to 4 m. Sonication of MLVs results in the formation of small unilamellar vesicles (SUVs) with diameters in the range of 200 to 500 Å, containing an aqueous solution in the core.

Phospholipids can form a variety of structures other than liposomes when dispersed in water, depending on the molar ratio of lipid to water. At low ratios, the liposome is the preferred structure. The physical characteristics of liposomes depend on pH, ionic strength and the presence of divalent cations. Liposomes can show low permeability to ionic and polar substances, but at elevated temperatures undergo a phase transition which markedly alters their permeability. The phase transition involves a change from a closely packed, ordered structure, known as the gel state, to a loosely packed, less-ordered structure, known as the fluid state. This occurs at a characteristic phase-transition temperature and results in an increase in permeability to ions, sugars and drugs.

Nanocapsules can generally entrap compounds in a stable and reproducible way. To avoid side effects due to intracellular polymeric overloading, such ultrafine particles (sized around 0.1 m) should be designed using polymers able to be degraded in vivo. Biodegradable polyalkyl-cyanoacrylate nanoparticles that meet these requirements are contemplated for use in the present invention, and such particles may be are easily made.

A population of cells or tissues that express IP$_3$R and Bcl-2 can thus be contacted with a biologically or therapeutically effective amount of Bcl-2-IP$_3$R interaction inhibitory compound in a pharmaceutical carrier under conditions effective to substantially inhibit Bcl-2 binding to IP₃R.

In some embodiments, the Bcl-2-IP₃R interaction inhibitory compounds described herein may be used to treat animals, patients, or subjects with a number of neoplastic diseases, including but not limited to lymphoma (e.g., follicular B-cell lymphoma), leukemia (chronic lymphocytic leukemia), multiple myeloma, melanoma, breast, prostate, and lung carcinomas. The Bcl-2-IP₃R interaction inhibitory compounds can also be used for reducing resistance to conventional cancer treatment.

In designing appropriate doses of the Bcl-2-IP₃R interaction inhibitory compounds for the treatment of vascularized tumors, one may readily extrapolate from the knowledge in the literature in order to arrive at appropriate doses for clinical administration. To achieve a conversion from animal to human doses, one would account for the mass of the agents administered per unit mass of the experimental animal and, preferably, account for the differences in the body surface area (m²) between the experimental animal and the human patient. All such calculations are well known and routine to those of ordinary skill in the art.

The intention of the therapeutic regimens described herein is generally to produce significant anti-neoplastic effects while still keeping the dose below the levels associated with unacceptable toxicity. In addition to varying the dose itself, the administration regimen can also be adapted to optimize the treatment strategy. In administering the particular doses, one can provide a pharmaceutically acceptable composition (according to FDA standards of sterility, pyrogenicity, purity and general safety) to the patient systemically. Intravenous injection is generally preferred. Continuous infusion over a time period of about 1 or 2 hours or so is also contemplated. In certain embodiments, the agent can be delivered to cancer cells by site-specific means.

The Bcl-2-IP₃R interaction inhibitory compounds may also be delivered in combination with a second agent that induces apoptosis in neoplastic cells. Although many anti-cancer agents may have, as part of their mechanism of action, an apoptosis-inducing effect, certain agents have been discovered, designed or selected with this as a primary mechanism, as described below.

Figure 3:
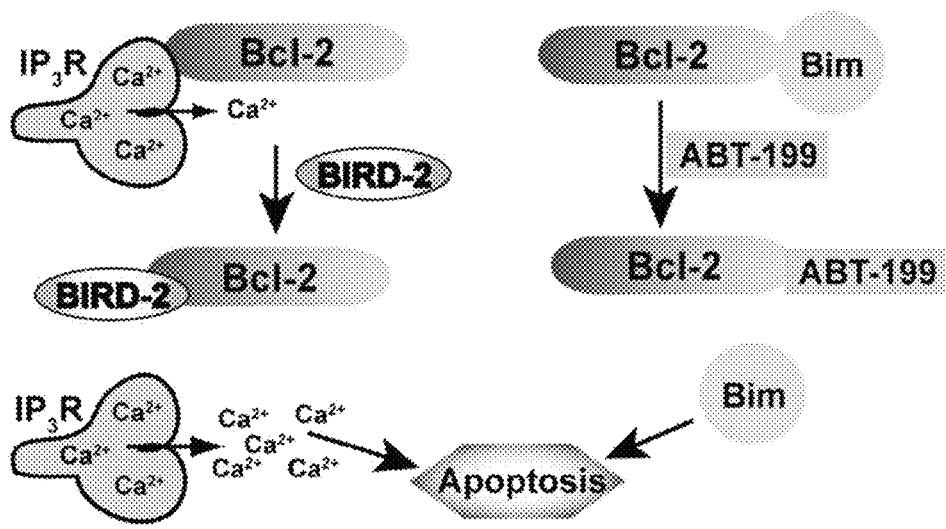
FIG. 3 illustrates a graphic showing that Bcl-2 inhibits apoptosis in two distinct ways. (Left) The BH4 domain of Bcl-2 binds to the IP$_3$R, preventing Ca$^{2+}$ elevations that induce apoptosis. BIRD-2 inhibits this interaction, inducing apoptosis by releasing high levels of Ca$^{2+}$ from the ER. (Right) BH1-3 domains of Bcl-2 bind BH3-only proteins like BIM, preventing Bim from activating Bax/Bak and inducing apoptosis. BH3-mimetics like ABT-263 and ABT-199 block this interaction, inducing apoptosis.

Without being bound by theory, it is believed that the combination of a Bcl-2-IP₃R interaction inhibitory compound and a Bcl-2/BH3 inhibitor overcomes Bcl-2s anti-apoptotic action by reversing two separate mechanisms by which Bcl-2 inhibits apoptosis (see FIG. 3). Therefore, in some embodiments, the second agent can be a small-molecule inhibitor that directly binds Bcl-2/IP₃R or related anti-apoptotic proteins and inhibits the Bcl-2-BH3 domain binding to BH3 domain proteins or BH3 only molecules, such as BID, NOXA, PUMA, BIK, BIM, and BAD (i.e., a Bcl-2/BH3 inhibitor). By targeting two different regions of Bcl-2 involved in apoptosis inhibition with the Bcl-2-IP₃R interaction inhibitory compounds described herein, which bind to the BH4 domain of Bcl-2, and an inhibitor of Bcl-2 to BH3 domain proteins, the proapoptotic activity of the Bcl-2/BH3 inhibitors and the Bcl-2-IP₃R interaction inhibitory compounds are enhanced. In certain embodiments, a combination of a Bcl-2-IP₃R interaction inhibitory compound and a Bcl-2/BH3 inhibitor induces synergistic cytotoxicity when administered to neoplastic cells, such as human myeloma cells (see FIG. 10).

One example of a small molecule inhibitor is gossypol or 1,6,7,1',6',7'-Hexahydroxy-5,5'-diisopropyl-3,3'-dimethyl-[2,2']binaphthalenyl-8,8'-dicarbaldehyde. Gossypol has the following formula:

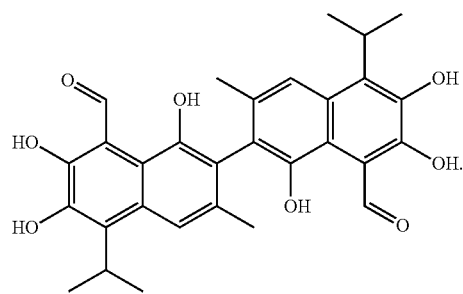 [SMILES: Cc1cc2c(C(C)C)c(O)c(O)c(C=O)c2c(O)c1-c1c(C)cc2c(C(C)C)c(O)c(O)c(C=O)c2c1O]

Gossypol is found in cottonseeds originally used as an herbal medicine in China. Gossypol binds via a conserved 16 amino acid motif called a Bcl-2 homology-3 (BH3) domain found on the surface of antiapoptotic Bcl-2 family proteins. This binding pocket represents a regulatory site, where endogenous antagonists dock onto Bcl-2 and related antiapoptotic proteins, negating their cytoprotective activity. Proof of concept experiments using BH3 peptides have suggested that compounds docking at this regulatory site on Bcl-2 and Bcl-XL effectively promote apoptosis of lymphoma and leukemia cells in vivo in mice.

Gossypol interacts with the BH3-binding pockets of 4 anti-apoptotic Bcl-2 family proteins tested to date, Bcl-2, Bcl-X$_L$, Bcl-B, and Bfl-1, displacing BH3 peptides with an inhibitory concentration of 50% (IC$_{50}$) of about 0.5 µM.

Another example of small molecule inhibitor of Bcl-2 is a semisynthetic analog of gossypol known as apogossypol or 5,5'-Diisopropyl-3,3'-dimethyl-[2,2']binaphthalenyl-1,6,7,1',6',7'-hexaol, which has the following general formula:

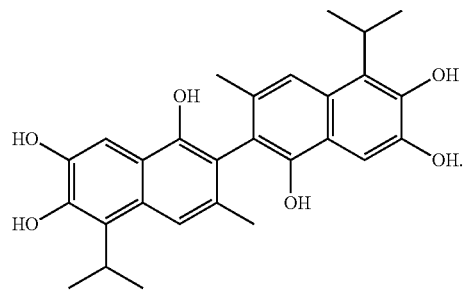

Other examples of chemical inhibitors of Bcl-2, Bcl-X$_L$, and Mcl-1 have been reported, most of which are currently in preclinical evaluation, including: chromenes or chromene derivatives, such as HA14-1 or 2-amino-6-bromo-4-cyano-ethoxycarbonyl-methyl)-4H-chromene-3-carboxylic acid ethyl ester or other compounds disclosed in U.S. Pat. No. 6,492,389; thiazolidins or thiazolidin derivatives, such as BH3I-1 or (2-[5-(4-Bromo-benzylidene)-4-oxo-2-thioxo-thiazolidin-3-yl]-3-methyl-butyric acid); benzene sulfonyl derivatives, such as BH3I-2 or (5-chloro-N-[2-chloro-4-(4-chloro-benzenesulfonyl)-phenyl]-2-hydroxy-3-iodo-benzamide); antimycin analogs, such as 3-(3-Formylamino-2-hydroxy-benzoylamino)-2,6-dimethyl-4,9-dioxo-8-pentyl-[1,5]dioxonane-7-carboxylic acid isopropyl ester or Antimycin A3, and antimycin analogues disclosed in U.S. Pat. No. 7,241,804 (e.g., structures I-V); theaflavins, such as 3,4,6-trihydroxy-1-(3,5,7-trihydroxy-chroman-2-yl)-benzo-cyclohepten-5-one; epigallechatechins (EGCGs), such as 3,4,5-Trihydroxy-benzoic acid 5,7-dihydroxy-2-(3,4,5-tri-hydroxy-phenyl)-chroman-3-yl ester; benzenesulfonamides, such as ABT-737 or N-[4-[4-(4'-Chloro-biphenyl-2-ylmethyl)-piperazin-1-yl]-benzoyl)-4-(3-dimethylamino-1-phenylsulfanylmethyl-propylamino)-3-nitro-benzenesulfonamide (a synthetic small-molecule inhibitor produced by NMR-guided, structure-based drug design (Abbott Laboratories, North Chicago, IL); indoles, such as GX15-070 (Gemin X, Montreal, Canada) or 2-[5-(3,5-Dimethyl-1H-pyrrol-2-ylmethylene)-4-methoxy-5H-pyroll-2-yl]-1H-indole; dibenzodiazocines, such as 2,9-Dimethoxy-11, 12-dihydro-dibenzo[c,g][1,2]diazocine 5,6-dioxide; and terphenyl derivatives, such as a compound having the following formula:

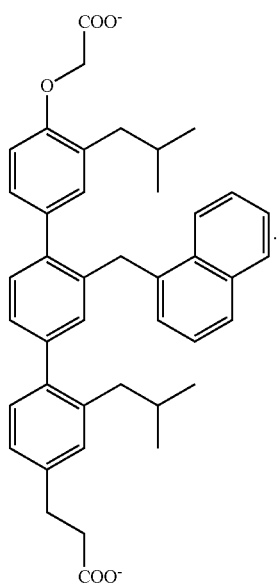

Side-by-side comparisons of these chemical inhibitors of antiapoptotic Bcl-2 proteins have not been reported, but their approximate rank-order potency with respect to affinity for the BH3 pocket of Bcl-2 or Bcl-$X_L$ appears to be ABT-737>EGCG>theafavins>gossypol>apogossypol>HA14-1 and antimycin. Accordingly, in one example the second agent administered to the cells is ABT-737 or N-[4-[4-(4'-Chloro-biphenyl-2-ylmethyl)-piperazin-1-yl]-benzoyl)-4-(3-dimethylamino-1-phenylsulfanylmethyl-propylamino)-3-nitro-benzenesulfonamide.

In some embodiments, the chemical inhibitors of antiapoptotic Bcl-2 proteins are BH3 mimetics capable of competitively inhibiting BH3-only protein binding to the hydrophobic grooves formed by Bcl-2 domains 1-3, inducing apoptosis in cells requiring to Bcl-2 for survival. Exemplary BH3 mimetics include, but are not limited to, ABT-737, ABT-263, and ABT-199.

The Bcl-2-IP$_3$R interaction inhibitory compound based treatment methods described herein may also be combined with any other methods generally employed in the treatment of the particular tumor, disease or disorder that the subject exhibits. So long as a particular therapeutic approach is not known to be detrimental to the patient's condition in itself, and does not significantly counteract the Bcl-2-IP$_3$R interaction inhibitory compound based treatment, its combination with the present invention is contemplated.

In another aspect, a Bcl-2-IP$_3$R interaction inhibitory compound can be co-administered with one or more anticellular agents. Examples anti-cellular agents include chemotherapeutic agents, as well as cytotoxins. Chemotherapeutic agents that can be used include: hormones, such as steroids; anti-metabolites, such as cytosine arabinoside, fluorouracil, methotrexate or aminopterin; anthracyclines; mitomycin C; vinca alkaloids; demecolcine; etoposide; mithramycin; anti-tumor alkylating agents, such as chlorambucil or melphalan. Other embodiments can include agents such as cytokines. Basically, any anti-cellular agent may be used.

Many forms of cancer have reports of mutations in tumor suppressor genes, such as p53. Inactivation of p53 results in a failure to promote apoptosis. With this failure, cancer cells progress in tumorigenesis, rather than become destined for cell death. Thus, delivery of tumor suppressors is also contemplated for use in the present invention to stimulate cell death. Examples of tumor suppressor agents are disclosed in U.S. Pat. Nos. 5,747,469; 5,677,178; and 5,756,455; 5,750,400; 5,654,155; 5,710,001; 5,756,294; 5,709,999; 5,693,473; 5,753,441; 5,622,829; and 5,747,282 (each incorporated herein by reference), Other compositions that may be administered with the Bcl-2-IP$_3$R interaction inhibitory compounds, include genes encoding the tumor necrosis factor related apoptosis inducing ligand termed TRAIL, and the TRAIL polypeptide (U.S. Pat. No. 5,763,223; incorporated herein by reference); the 24 kD apoptosis-associated protease of U.S. Pat. No. 5,605,826 (incorporated herein by reference); Fas-associated factor 1, FAF1 (U.S. Pat. No. 5,750,653; incorporated herein by reference). Also contemplated for use in these aspects of the present invention is the provision of interleukin-1p-converting enzyme and family members, which are also reported to stimulate apoptosis It will be appreciated that the therapeutic agents administered with the Bcl-2-IP$_3$R interaction inhibitory compounds are not limited to the therapeutic agents described above, and that other therapeutic agents and other agents, which do not have therapeutic properties, can be used.

The following example is included to demonstrate different embodiments of the invention. It should be appreciated by those of skill in the art that the techniques disclosed in the example, which follow represent techniques discovered by the inventors to function well in the practice of the claimed embodiments, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the claims.

EXAMPLE

Figure 2:
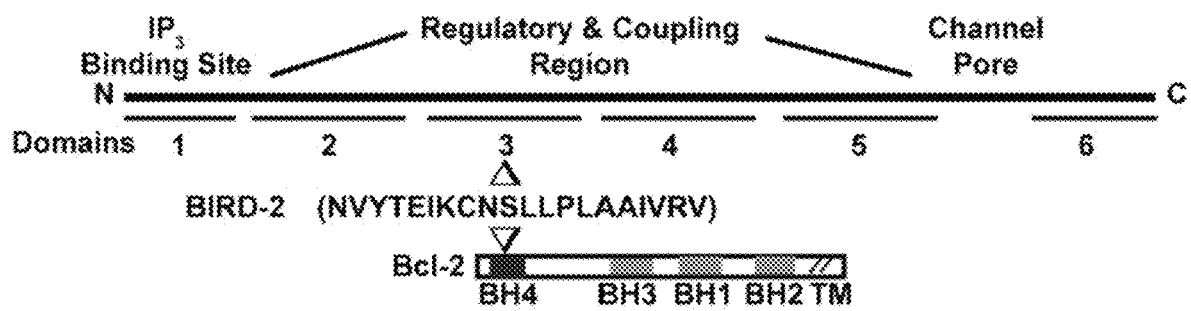
FIG. 2 illustrates a graphic showing that BIRD-2 targets Bcl-2-IP$_3$R interaction. BIRD-2 is a synthetic peptide derived from IP$_3$R domain 3 where Bcl-2 binds. It functions as a decoy peptide, inhibiting Bcl-2-IP3R interaction and inducing apoptosis in Bcl-2-positive cancer cells.

Novel Cancer Therapeutic Drugs Targeting the BH4 Domain of Bcl-2
Proof-of-Principle for Targeting Bcl-2-IP$_3$R Interaction for Cancer Treatment To selectively target Bcl-2-IP$_3$R interaction, we developed BIRD-2 (Bcl-2-IP$_3$R interaction Disrupter-2), a synthetic peptide derived from the Bcl-2 binding site on the IP$_3$R and previously referred to as TAT-IDP$_{DD/AA}$ or TAT-IDP$^s$ (FIG. 2). By binding to the BH4 domain of Bcl-2, BIRD-2 disrupts Bcl-2-IP$_3$R interaction, reversing Bcl-2's repressive effect on IP$_3$R-mediated Ca$^{2+}$ release. Through this mechanism BIRD-2 induces high amplitude Ca$^{2+}$ elevation, triggering apoptosis in primary human CLL cells, and diffuse large B-cell lymphoma lines. BH3-mimetics, on the other hand, induce apoptosis by binding to the hydrophobic groove formed by Bcl-2 domains 1-3, thereby inducing apoptosis by disrupting the interaction of Bcl-2 with BH3-only proteins. BIRD-2 selectively disrupts Bcl-2-IP$_3$R interaction and does not disrupt the binding of pro-apoptotic proteins (e.g., Bim) by Bcl-2. Thus, BIRD-2 and BH3-mimetic agents target completely different regions of the Bcl-2 protein and overcome Bcl-2's anti-apoptotic action by reversing two separate mechanisms by which Bcl-2 inhibits apoptosis (FIG. 3). Finding that Bcl-2 inhibits apoptosis by two distinct mechanisms involving separate regions of the Bcl-2 protein suggests that targeting only one of the mechanisms may be of limited therapeutic value and argues that efforts to target the other mechanism should be undertaken. In support of this concept, we recently discovered that BIRD-2 induces apoptosis in ABT-263/ABT-199 resistant Bcl-2 positive human myeloma cell lines (HMCLs). Moreover, we find synergistic killing of HMCLs by combining BIRD-2 with chemotherapeutic agents used to treat patients with multiple myeloma. Collectively, these findings advocate for developing new therapeutic agents that function like BTRD-2 to target the Bcl-2-IP$_3$R interaction, both to circumvent resistance to BH3-mimetics and potentially increase the therapeutic efficacy of BH3-mimetics.

Reciprocal Sensitivity of Multiple Myeloma Cells to BIRD-2 and BH3-Mimetic Agents Multiple myeloma is a Bcl-2-positive malignancy of plasma cells derived from relatively mature forms of B-lymphocytes present mainly in the bone marrow. Multiple myeloma is nearly universally fatal and thus a major clinical challenge in need of novel targeted therapeutic approaches. Though multiple myeloma cells lack translocation responsible for elevating Bcl-2 in follicular lymphoma, the majority of human myeloma cell lines (HMCLs) have elevated Bcl-2 expression levels comparable to those in follicular lymphoma cells. Moreover, Bcl-2 levels are reported to increase in multiple myeloma cells following chemotherapy treatment. Therefore, treatment of multiple myeloma with BH3-mimetics is an appealing strategy. In some but not all HMCLs and primary patient samples, the BH3-mimetic ABT-737 has demonstrated both substantial single-agent anti-myeloma activity and synergistic activity with various chemotherapeutic agents. Recent studies also indicate responsiveness of HMCLs and primary patient samples to the Bcl-2-selective BH3-mimetic ABT-199.

However, multiple myeloma is a heterogeneous malignancy, both in terms of clinical course and responsiveness to treatment. The heterogeneity of multiple myeloma has a molecular basis and molecular abnormalities are of considerable prognostic value for patient survival. The heterogeneity of HMCLs closely reflects that of primary multiple myeloma in patients and particular subtypes correlate with responsiveness to ABT-737 and ABT-199. In general, ABT-737 sensitive lines harbor the translocation associated with a relatively high ratio of Bcl-2 to another anti-apoptotic Bcl-2 family member, Mcl-1.

We found for the first time that inhibiting Bcl-2-IP$_3$R interaction with BIRD-2 induces apoptosis in HMCLs. Significantly, BIRD-2 induces apoptosis in two HMCLs that are resistant to BH3-mimetic agents including ABT-737, ABT-263 and ABT-199. Furthermore, one of the BIRD-2-sensitive lines, NCI-H929, corresponds to a multiple molecular subgroup that is resistant to BH3-mimetic agents and belongs to a poor prognosis category associated with chromosomal translocation. Thus, although BH3-mimetic agents represent a major advance in cancer treatment, resistance to these agents occurs and limits their efficacy, not only in multiple myeloma but other lymphoid malignancies as well. The resistance problem is not unique to HMCLs, but is illustrated by studies of ABT-737 and ABT-199 in primary MM cells where resistance was detected in more than half of primary patient samples tested. Therefore, these findings indicate the potential therapeutic importance of targeting both of Bcl-2's anti-apoptotic mechanisms. Adding to the potential value of targeting Bcl-2-IP$_3$R interaction for treatment of multiple myeloma is the evidence reported here of synergistic activity when combined with chemotherapeutic agents typically employed in multiple myeloma treatment, and with ABT-263 and ABT-199.

Interestingly, a reciprocal relationship between sensitivity to cell death induction by BIRD-2 and the BH3-mimetic agents is revealed in our present work. We observe much higher Bim levels in cells sensitive to ABT compounds and lower Bim levels in cells resistant to ABT compounds. This is consistent with the known mechanism of ABT action, which is to displace Bim from its binding site on Bcl-2, thereby activating mitochondria-mediated cell death. Further investigation is required to identify mechanism(s) responsible for the increased sensitivity of ABT-resistant HMCLs to BIRD-2.

In summary, we know that BIRD-2 induces apoptosis in primary human CLL cells and in diffuse large B-cell lymphoma cell lines. Here we show that BIRD-2 can similarly induce apoptosis in HMCLs, including in lines resistant to the ABT class of BH3-mimetic agents. Included among the BIRD-2-sensitive but ABT-resistant lines is NCI-H929, which is recognized as bearing a poor prognosis molecular signature. These findings emphasize the potential therapeutic value of targeting the Bcl-2-IP$_3$R interaction to induce death of ABT-resistant cells and the need to develop therapeutic agents that target the Bcl-2-IP$_3$R interaction.

Figure 4:
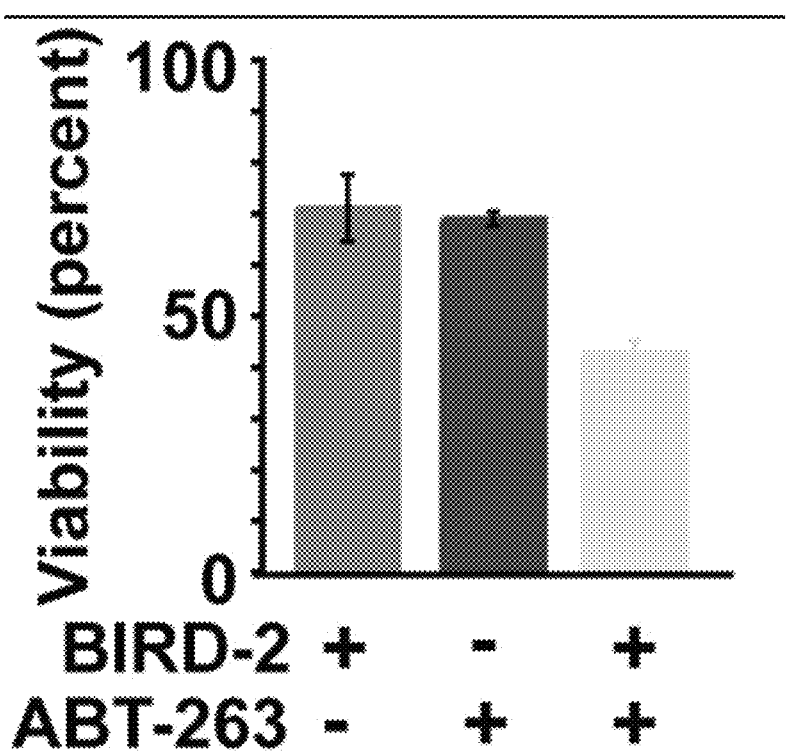
FIG. 4 is a graph illustrating BIRD-2/ABT-263 synergism. H2171 Small cell lung cancer (SCLC) cells treated from 24 hr with 5 μM BIB1 and 39 nM ABT-263 alone or together.

Sensitivity of Small Cell Lung Cancer Cells to Disruption of Bcl-2-IP$_3$R Interaction Although most of our work has been in Bcl-2-positive lymphoid malignancies, we have recently extended our work to show that BIRD-2 induces cell death in small cell lung cancer (SCLC), a Bcl-2 positive form of cancer that has a very high mortality rate and in which novel treatment strategies are desperately needed. BH3-mimetics are less effective in SCLC than in lymphoid malignancies such as CLL. We have treated 15 SCLC lines with BIRD-21, with greater than two-fold selective cytotoxicity in 11 of the lines, with IC$_{50}$ ranging from 3-40 µM. Moreover, we find that combining the BH3-mimetic agent ABT-263 with BIRD-2 induces synergistic cytotoxicity (FIG. 4), indicating the value of targeting both mechanisms by which Bcl-2 inhibits apoptosis.

Discovery of Four Lead Compounds that Target the Bh4 Domain of Bcl-2

The preceding findings, based on our development of a synthetic peptide that targets Bcl-2-IP$_3$R interaction, provides strong proof-of-principle evidence in favor of developing a therapeutic agent that blocks Bcl-2-IP$_3$R interaction and thus kills Bcl-2-positive cancer cells. A high throughput screen was performed with the goal of identifying drug-like compounds that bind to the BH4 domain of Bcl-2 and mimic the action of BIRD-2. The high throughput screening identified compounds that promote induction of apoptosis in two Bcl-2-positive multiple myeloma cell lines, NCI-H929 and KMS-12-BM. These two lines span a spectrum between high and low sensitivity to BIRD-2 (i.e., BIRD-2 induces apoptosis in NCI-H929 with an EC$_{50}$ of 5 µM and KMS-12-BM with an EC$_{50}$ of 25 µM). Cell death measurements employed a caspase-3/7 assay (AnaSpec) in three screening tiers (single point primary screen, triplicate hit confirmation, and triplicate dose response) with signal-to-background consistently >10 and Z'>0.5. Activity was measured relative to apoptosis induction by 10 μM BIRD-2.

Figure 5:
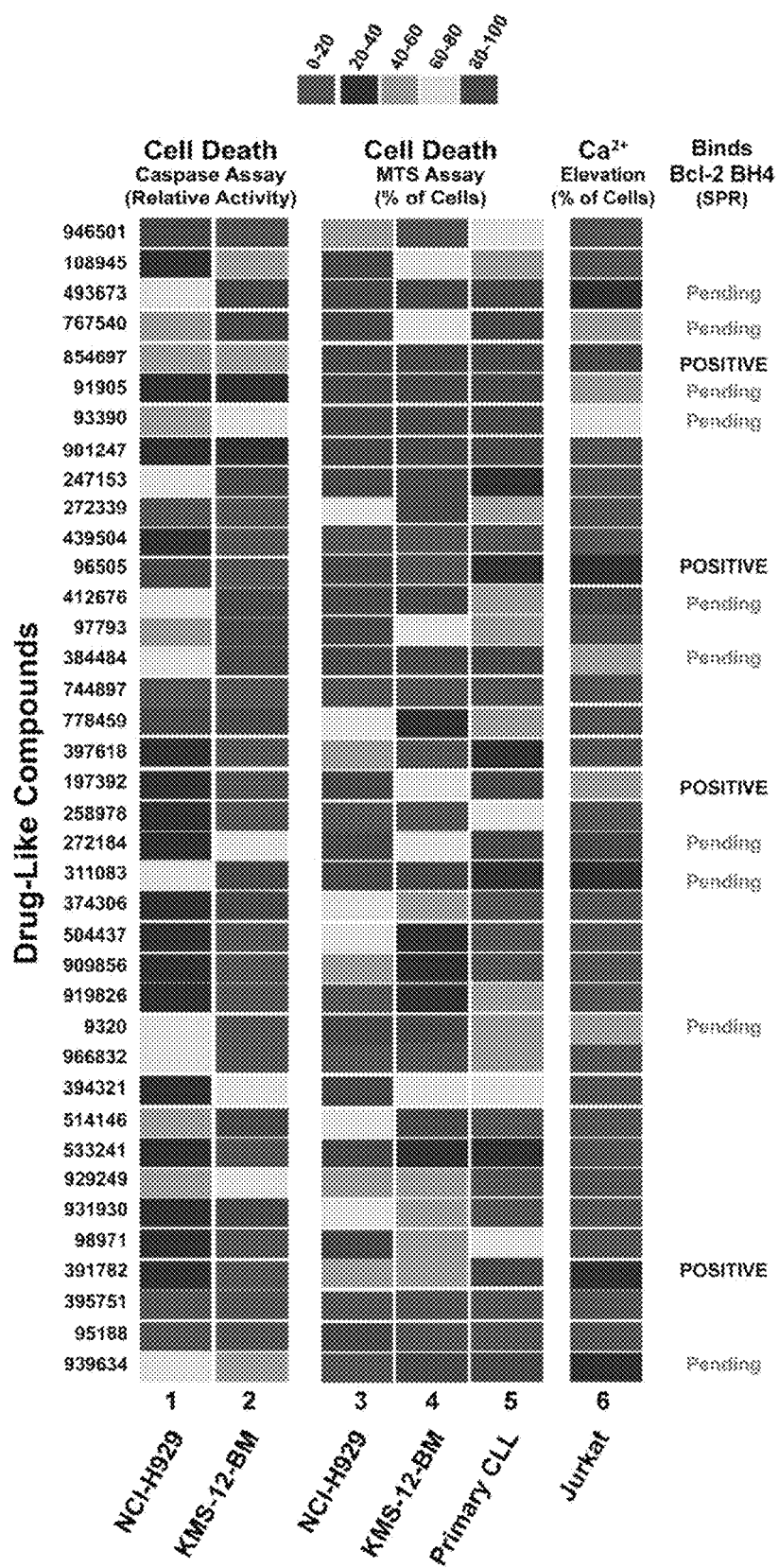
FIG. 5 illustrates a graphic showing a heat map summarizing HTS results identifying 4 lead compounds that kill Bcl-2-positive cancer cell lines, primary CLL cells and elevate Ca$^{2+}$ in Bcl-2 positive Jurkat cells.

Of the compounds tested, 148 were identified as hits at 6.5 μM in the primary single-point screen with activity >30% relative to apoptosis induced by 10 μM BIRD-2 in NCI-H929 cells. These compounds, along with 320 additional compounds chosen by virtual screening, were screened for hit confirmation. Also, a secondary assay for compound effect on apoptosis was performed in KMS-12-BM cells. Comparing results with the two different cell lines, 19 compounds induced apoptosis in NCI-H929 cells at 6.5 μM, while having little to no effect on apoptosis of KMS-12-BM cells. An additional 20 compounds demonstrated activity in both NCI-H929 and KMS-12-BM cells, with relatively greater effect on NCI-H929 than on KMS-12-BM. Thus, a total of 39 compounds were chosen for triplicate confirmation screening. The findings are schematically summarized by means of the heat map in FIG. 5. An ID number, assigned by the chemist(s) who synthesized the compounds, is located to the left. This ID is for identification purposes only and does provide other information about the compound. Columns 1 and 2 represent caspase activity, measured after 24 hr of treatment at UCDDC, normalized to the highest caspase activity observed. Activity levels range from low, represented by the color purple, to high, represented by the color red. Considerable variation among different compounds and between the myeloma lines is observed evident. Columns 3 and 4 in the heat map (FIG. 5) summarize results of cell death assays testing cell death induction in the same myeloma lines in the Distelhorst laboratory using the MTS assay. In addition, the same assay was used to test the sensitivity of primary human CLL cells to each compound, as summarized in lane 5. The effect of each compound on intracellular $Ca^{2+}$ concentration was measured by digital imaging and results are shown as percentage of cells responding with a significant (more than twofold above baseline) elevation of cytoplasmic $Ca^{2+}$ concentration. The choice of the Jurkat line for these $Ca^{2+}$ measurements was based on our extensive evidence that BIRD-2 binds to the BH4 domain of Bcl-2 endogenously present in this line and that disruption of Bcl-2-IP3R interaction by BIRD-2 elevates cytoplasmic $Ca^{2+}$ in this line. An example of $Ca^{2+}$ elevation in response to one of the compounds is illustrated in FIG. 6.

Figure 6:
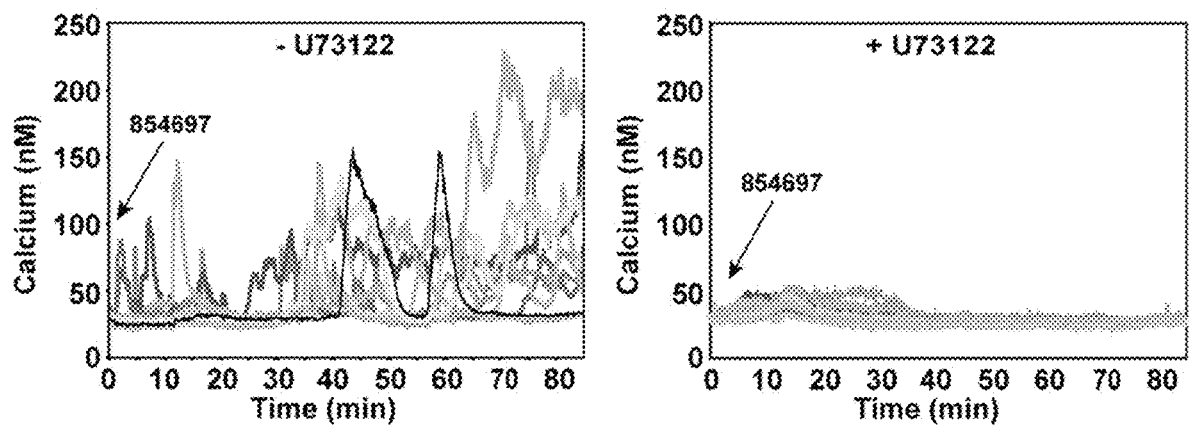
FIG. 6 illustrates charts showing that compound 854697 works on-target, inducing IP$_3$R-mediated Ca$^{2+}$ elevation. Pretreatment of Jurkat cells for 30 min with the phospholipase c inhibitor U73122 to block IP$_3$ synthesis blocks 854697-induced Ca$^{2+}$ elevation, consistent with hypothesis that 854697 disrupts Bcl-2-IP$^3$R interaction, releasing Ca$^{2+}$ from the ER lumen into the cytoplasm where it is detected by digital imaging.
Figure 7:
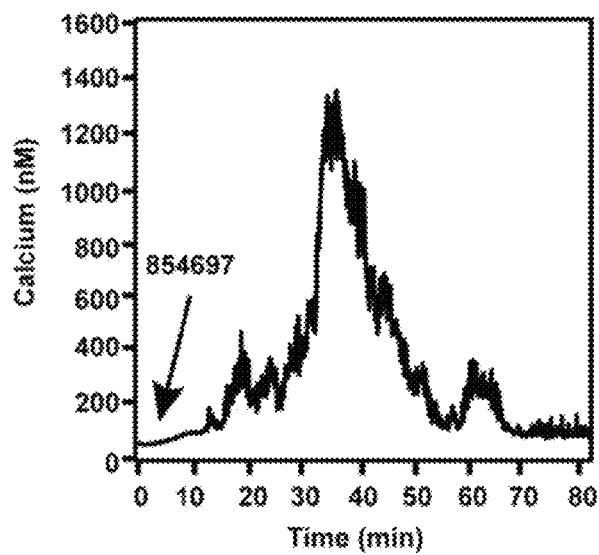
FIG. 7 is a graph illustrating that 854697 induces Ca$^{2+}$ elevation in primary human CLL cells. Shown is a trace averaging Ca$^{2+}$ elevations induced in 80 CLL cells, consistent with inhibition of Bcl-2-IP$_3$R interaction by 854697.

To further substantiate the significance of the observed elevations of cytoplasmic $Ca^{2+}$, we tested the effect of U73122 on the $Ca^{2+}$ responses to 854697 in Jurkat cells (FIG. 6). U73122 is a chemical inhibitor of phospholipase c, the enzyme that generates $IP_3$. U73122 completely blocked 854697-induced $Ca^{2+}$ elevation, demonstrating that the $Ca^{2+}$ elevations induced by 854697 were mediated through $IP_3R$ channel opening, and thus 854697 works 'on-target'. Moreover, 854697 also induces $Ca^{2+}$ elevation in primary CLL cells, illustrated in FIG. 7. This resembles the $Ca^{2+}$ elevation induced by BIRD-2 in our earlier studies in primary human CLL cells.

Figure 8:
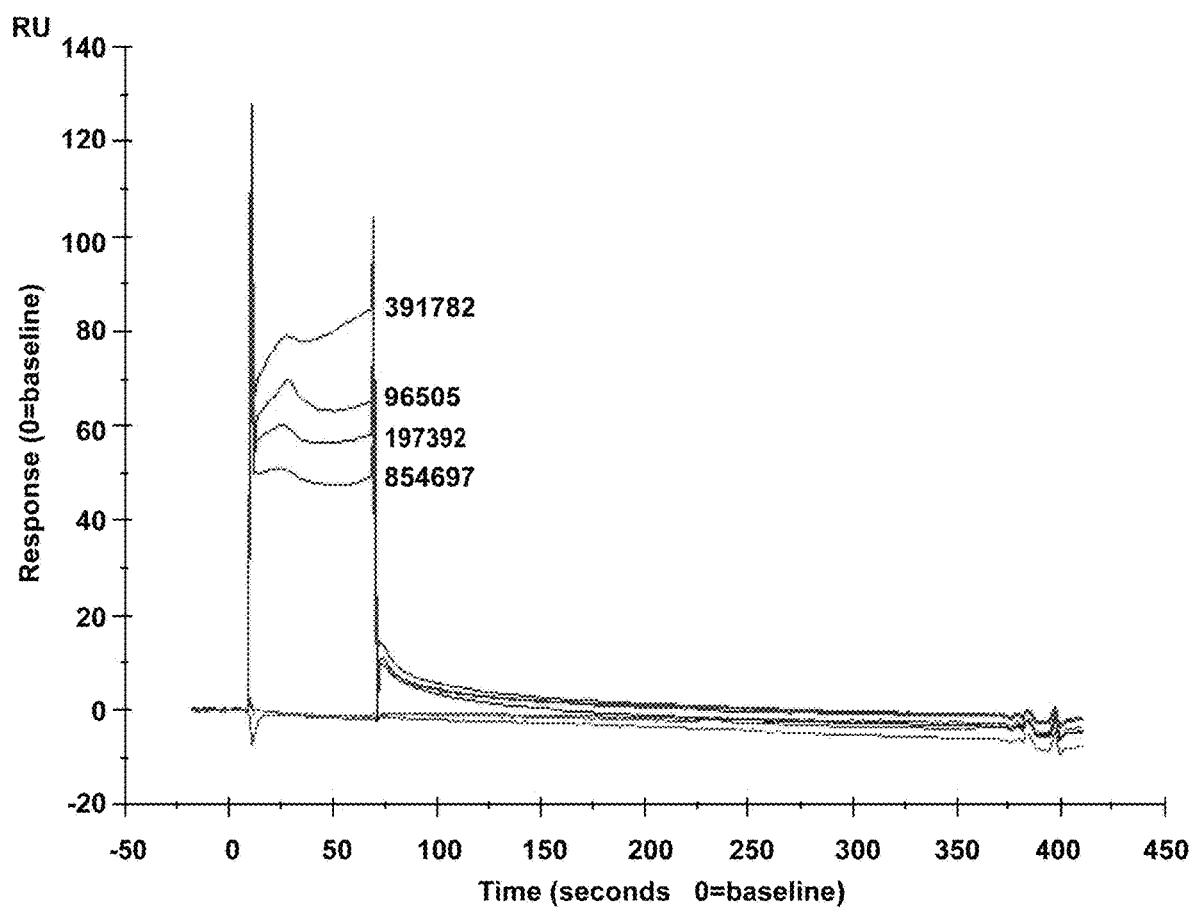
FIG. 8 is a graph illustrating surface plasmon resonance (SPR) results indicating four compounds that bind to the BH4 domain of Bcl-2. Dose response testing indicates a Kd of 5.7 μM for 854697 and 24 μM for 96505.
Figure 9:
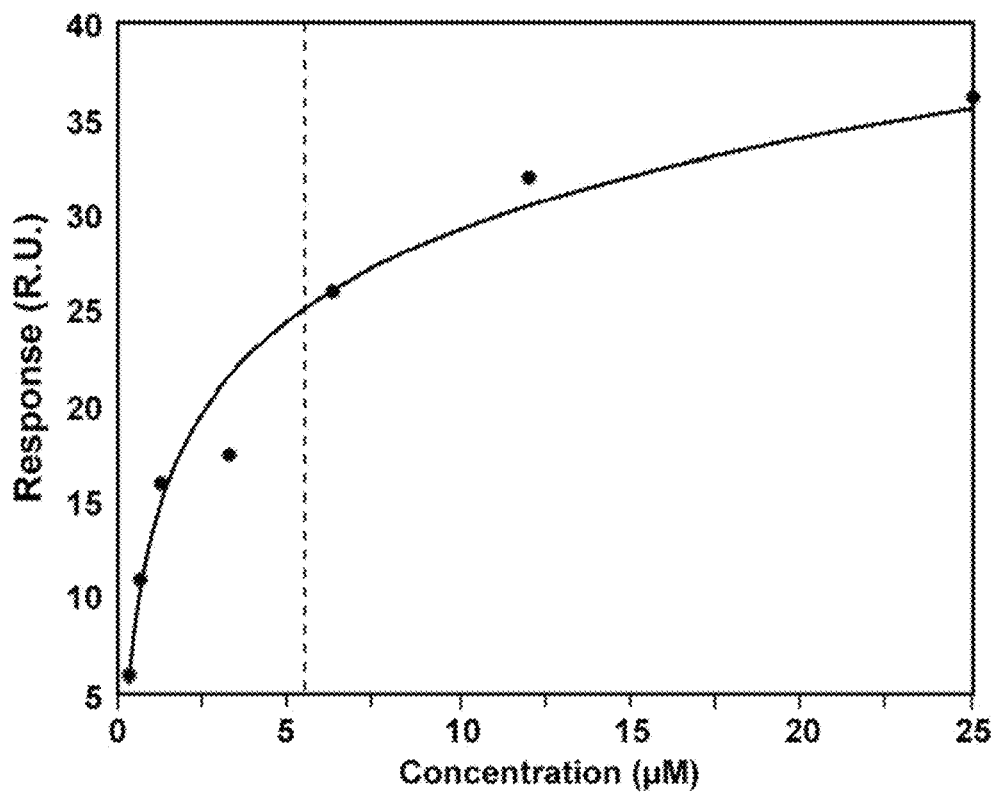
FIG. 9 is a graph illustrating surface plasmon resonance (SPR) results indicating that 854697 binds to the BH4 domain of Bcl-2 with $K_d$ 5.71 μM.

Of the 39 compounds tested, 14 fulfill the criteria of both inducing cell death and $Ca^{2+}$ elevation. The next step in compound validation was to perform surface plasmon resonance (Biacore) to test for binding to the BH4 domain of Bcl-2. This strategy is based on our earlier work indicating that the BH4 domain binds to $IP_3Rs$ and, moreover, BIRD-2 binds to this domain, thereby disrupting Bcl-2-$IP_3R$ interaction. To date, we have positive evidence of compound binding to the BH4 domain in 4 compounds tested by SPR (FIG. 8). Testing of the remaining compounds from the 14 lead compounds is in progress. An example of a full binding curve calculating Kd of 5.6 μM for compound 854697 is shown in FIG. 9.

In summary, through an iterative process we screened a library of 25,480 drug-like compounds, discovering that drug-like compounds 854697, 197392, 96505, 391782 bind to the BH4 domain of Bcl-2, targeting Bcl-2-$IP_3R$ interaction and inducing cell death in multiple myeloma lines and primary human CLL cells.

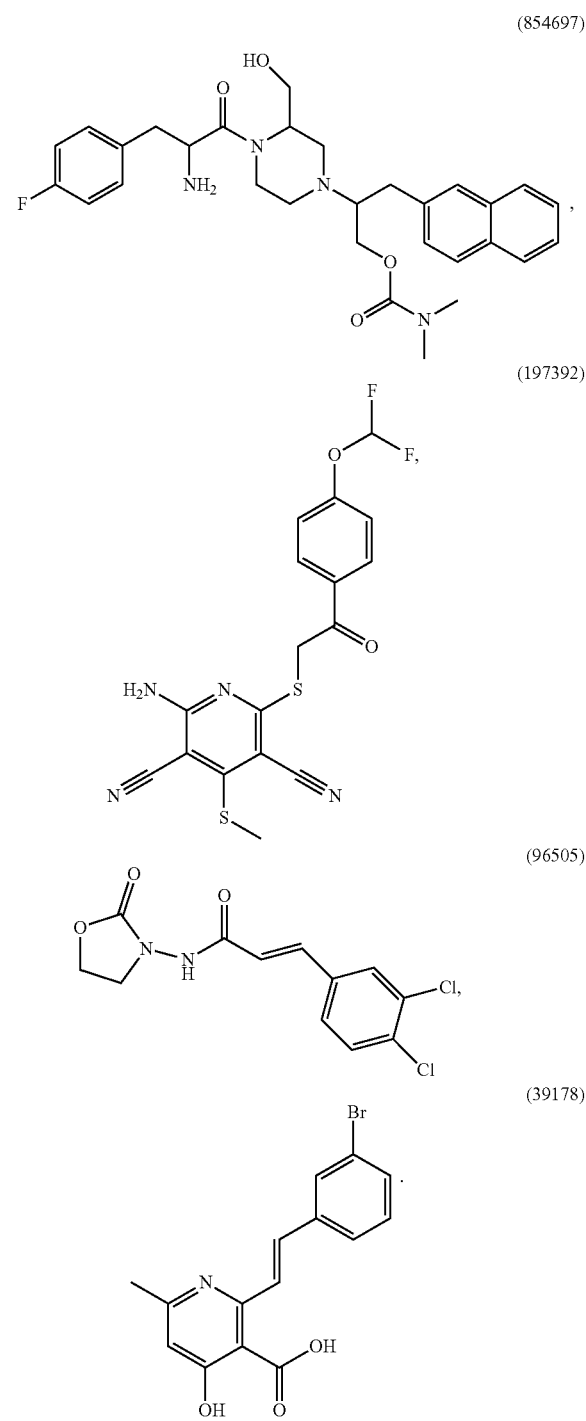

Synergy Between 854697 and the BH3-Mimetic ABT-263

Figure 10:
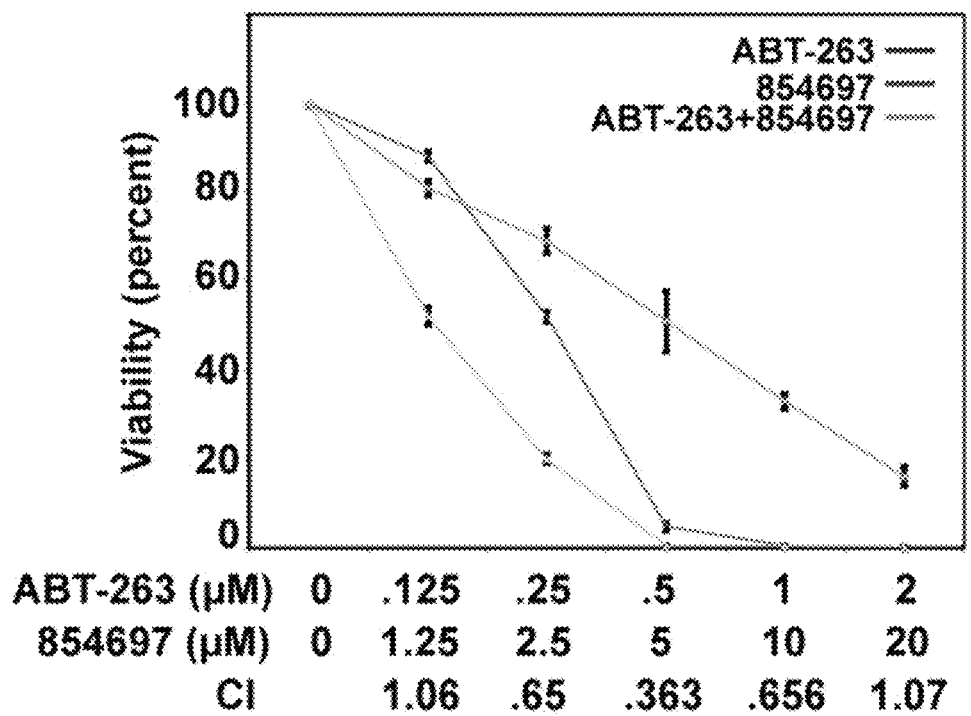
FIG. 10 is a graph illustrating the synergistic effect between 854697 and the BH3-mimetic ABT-263. KMS-12-BM cells, which express Bcl-2, were treated as shown with combinations of these agents at fixed concentration ratios, demonstrating synergy (CI<1) in inducing cell death.

Since Bcl-2 works by two distinct mechanisms to inhibit apoptosis, we investigated the possibility that 854697 and ABT-263, which selectively target each of these mechanisms, might synergistically kill cancer cells. As shown in FIG. 10, we incubated KMS-12-BM human myeloma cells with each compound at a fixed concentration ratio and assessed cell viability by CellTiter-Glo assay. Results indicate an increase in cell death responses when both compounds are combined. Combination indices (CI) were computed at each concentration to determine whether the increased cytotoxicity is due to an additive (CT=1) or synergistic (CI<1) effect. At several compound concentrations, the CI was <1, indicating synergistic cell death induction when these agents that act by different mechanisms are combined. These findings indicate additional value in developing 854697 as a novel therapeutic agent for Bcl-2-positive malignancies.

Finally, we have data indicating that 854697 kills small cell lung cancer cells. Importantly, 854697 does not have toxic activity toward normal cells, as represented by normal human peripheral blood lymphocytes.

While this invention has been shown and described with references to various embodiments thereof, it will be understood by those skilled in the art that changes in form and details may be made therein without departing from the scope of the invention encompassed by the appended claims. All patents, publications and references cited in the foregoing specification are herein incorporated by reference in their entirety.

I claim:

1. A method of treating a Bcl-2 associated cancer in a subject in need thereof, comprising:
administering to the subject having cancer cells that express $IP_3$ receptors ($IP_3R$) and Bcl-2 a compound that inhibits binding of Bcl-2 to $IP_3R$ of the cancer cells that express $IP_3R$ and Bcl-2, the compound binding to the BH4 domain of Bcl-2 and having formula (I):

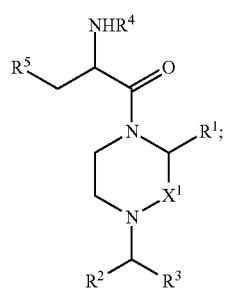

wherein $X^1$ is $CH_2$, or $C=O$;
$R^1$, $R^2$, $R^3$, $R^4$, and $R^5$ are the same or different and are independently selected from the group consisting of hydrogen, substituted or unsubstituted $C_1$-$C_{24}$ alkyl, $C_2$-$C_{24}$ alkenyl, $C_2$-$C_{24}$ alkynyl, $C_3$-$C_{20}$ aryl, heterocycloalkenyl containing from 5-7 ring atoms, heteroaryl or heterocyclyl containing from 5-14 ring atoms, $C_6$-$C_{24}$ alkaryl, $C_6$-$C_{24}$ aralkyl, halo, silyl, hydroxyl, sulfhydryl, $C_1$-$C_{24}$ alkoxy, $C_2$-$C_{24}$ alkenyloxy, $C_2$-$C_{24}$ alkynyloxy, $C_5$-$C_{20}$ aryloxy, acyl, $C_2$-$C_{24}$ alkylcarbonyl, $C_6$-$C_{20}$ arylcarbonyl, acyloxy, $C_2$-$C_{24}$ alkoxycarbonyl, $C_6$-$C_{20}$ aryloxycarbonyl, $C_2$-$C_{24}$ alkylcarbonato, $C_6$-$C_{20}$ arylcarbonato, carboxy, carboxylato, carbamoyl, $C_1$-$C_{24}$ alkyl-carbamoyl, arylcarbamoyl, thiocarbamoyl, carbamido, cyano, isocyano, cyanato, isocyanato, isothiocyanato, azido, formyl, thioformyl, amino, $C_1$-$C_{24}$ alkyl amino, $C_5$-$C_{20}$ aryl amino, $C_2$-$C_{24}$ alkylamido, $C_6$-$C_{20}$ arylamido, sulfanamido, imino, alkylimino, arylimino, nitro, nitroso, sulfo, sulfonato, $C_1$-$C_{24}$ alkylsulfanyl, arylsulfanyl, $C_1$-$C_{24}$ alkylsulfinyl, $C_5$-$C_{20}$ arylsulfinyl, $C_1$-$C_{24}$ alkylsulfonyl, $C_5$-$C_{20}$ arylsulfonyl, sulfonamide, phosphono, phosphonato, phosphinato, phospho, phosphino, polyalkyl ethers, phosphates, phosphate esters, groups incorporating amino acids or other moieties expected to bear positive or negative charge at physiological pH, and combinations thereof; and pharmaceutically acceptable salts thereof.

2. The method of claim 1, the compound reversing the interaction of Bcl-2 with $IP_3R$ of cancer cells that express $IP_3R$ and Bcl-2.

3. The method of claim 1, further comprising administering to the subject a second agent that inhibits binding of Bcl-2 to BH3 pro-apoptotic proteins.

4. The method of claim 3, wherein the combination of the compound of formula (I) and the second agent induces synergistic cytotoxicity of cancer cells that express $IP_3R$ and Bcl-2.

5. The method of claim 4, the second agent comprising at least one of a peptide or small molecule.

6. The method of claim 1, the compound selected from the group consisting of:

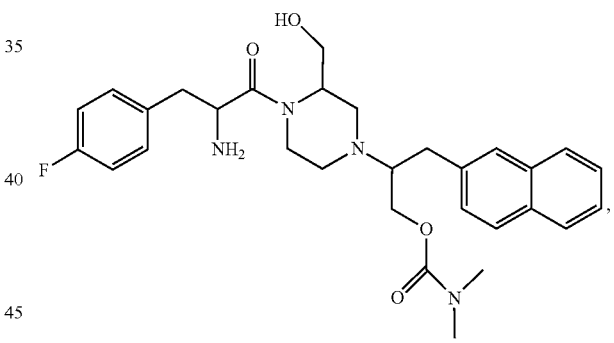

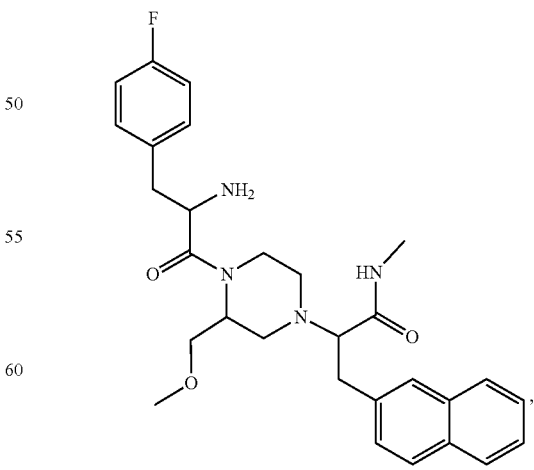

51
-continued
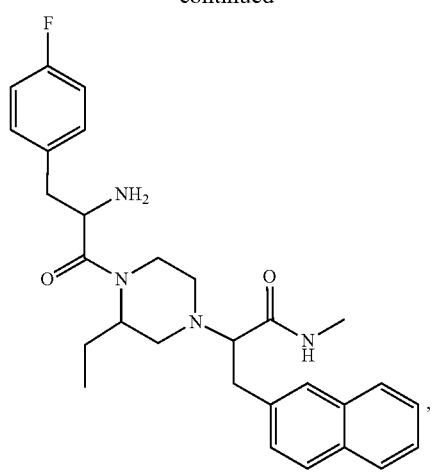
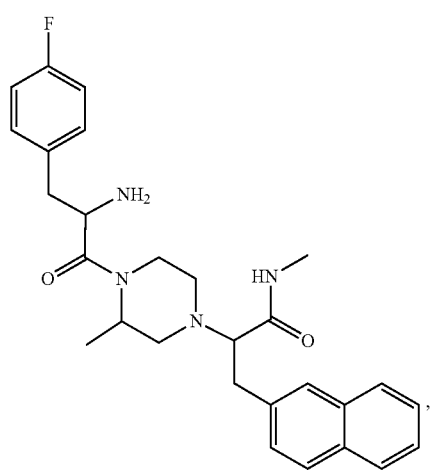
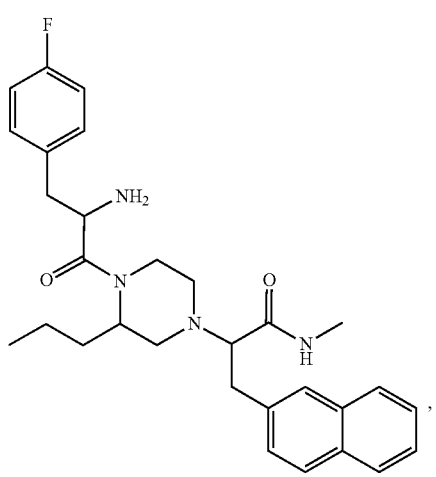
52
-continued
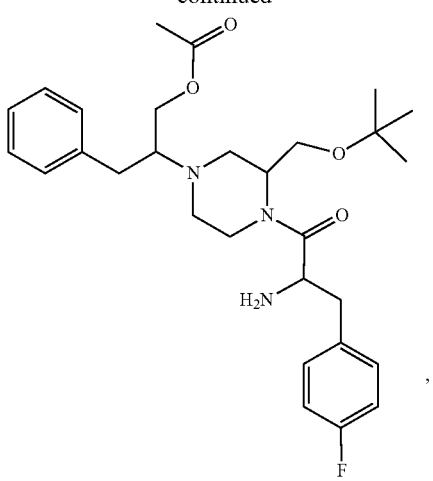
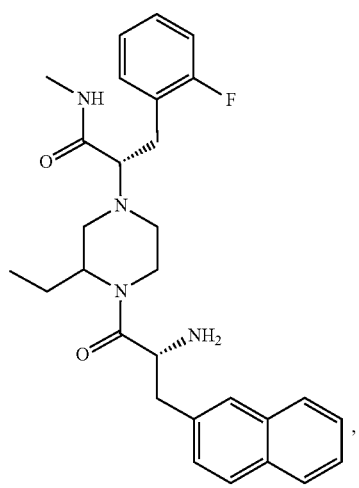
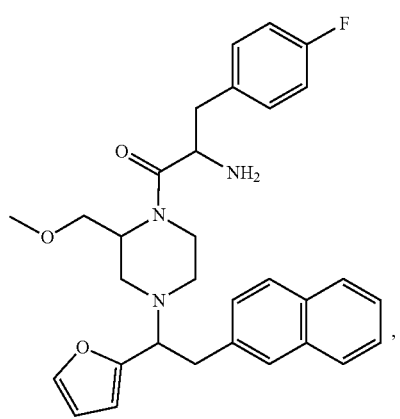

53
-continued
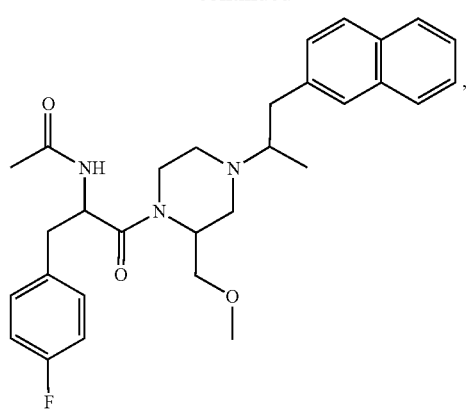
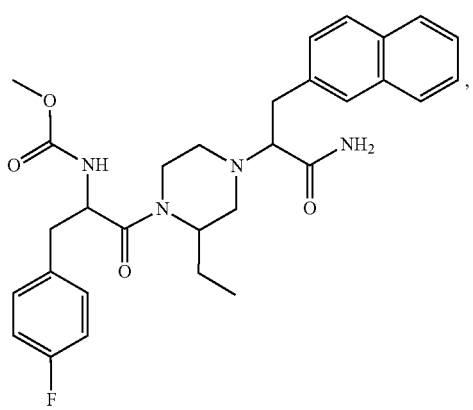
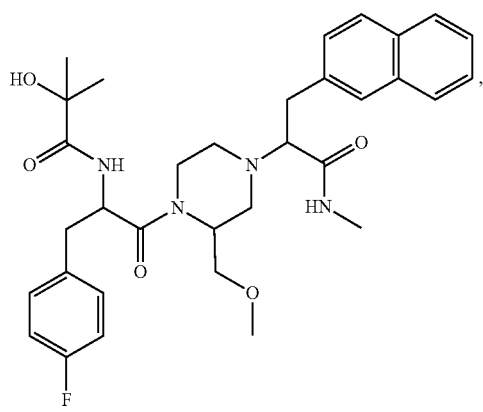
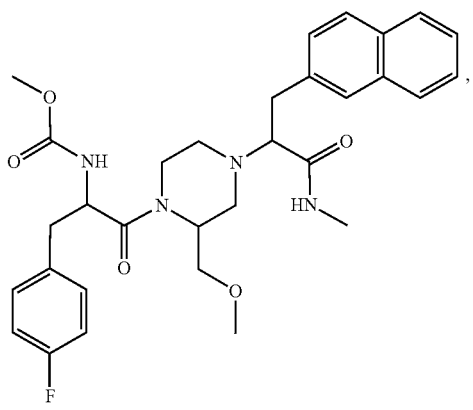
54
-continued
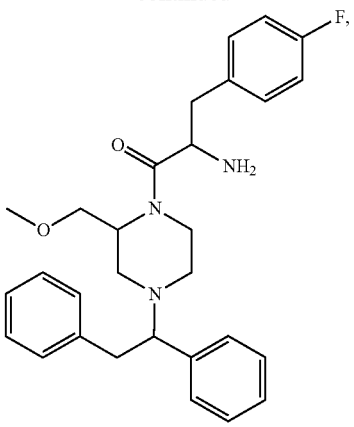
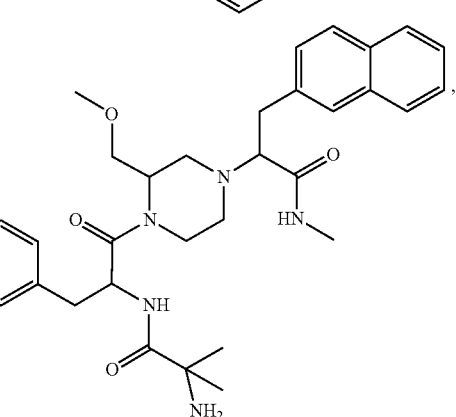
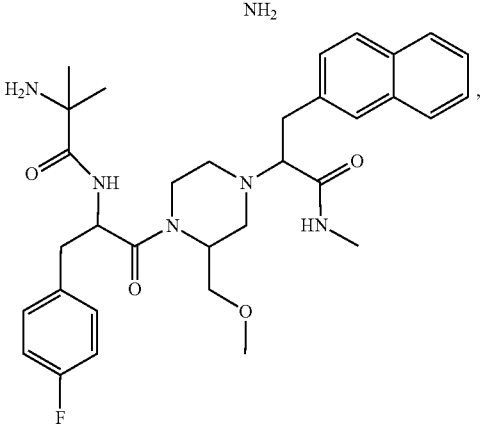
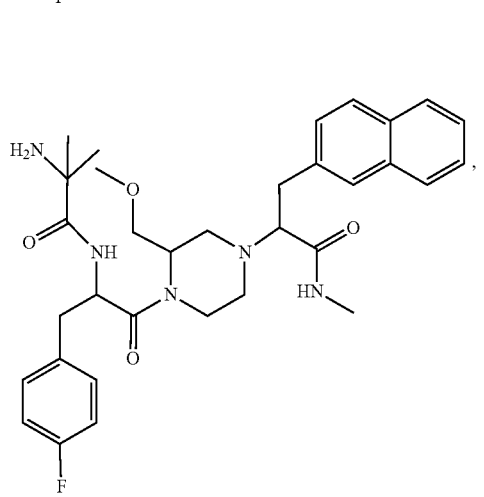

55
-continued
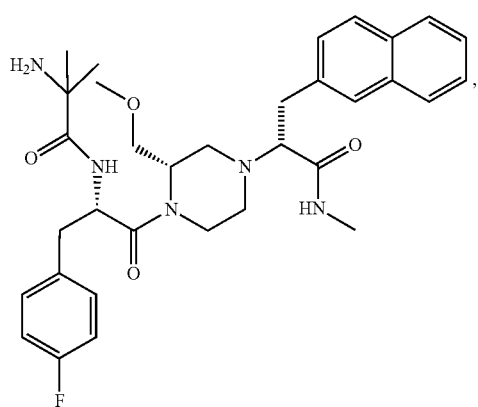
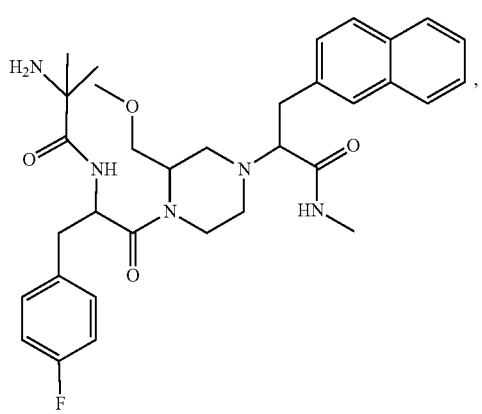
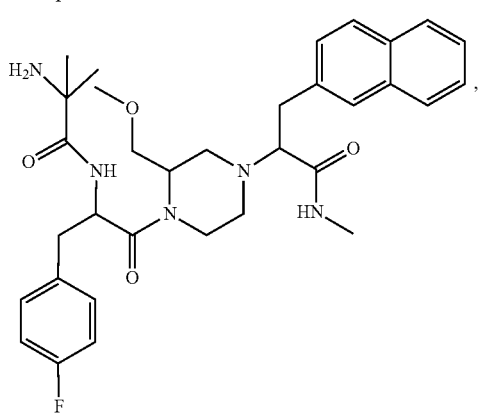
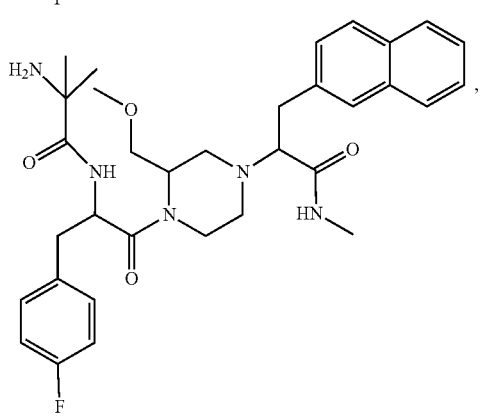
56
-continued
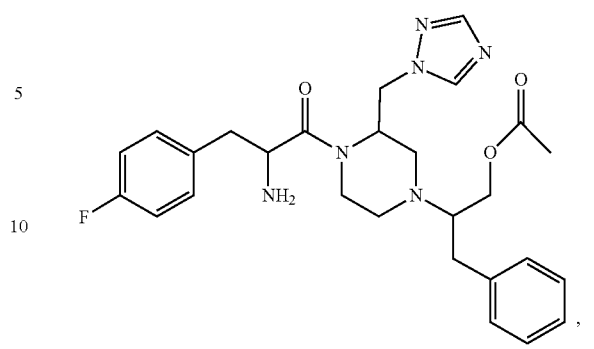
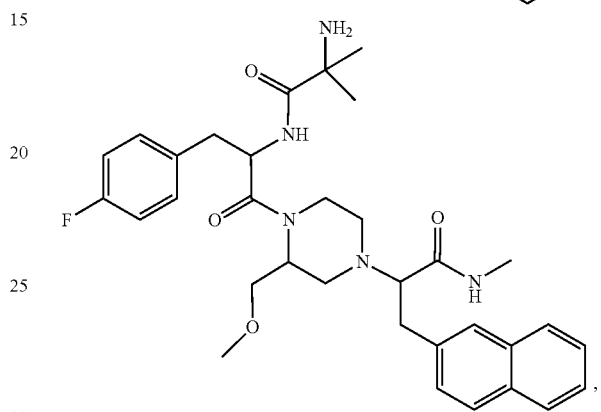
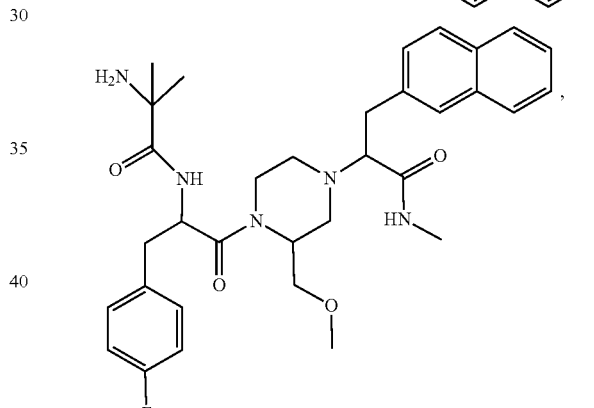
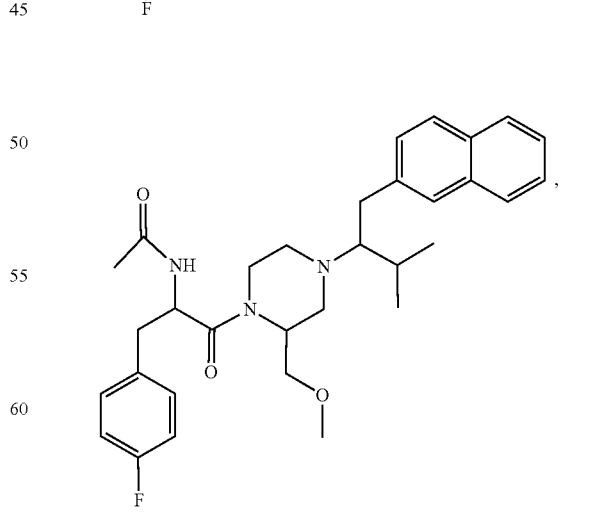

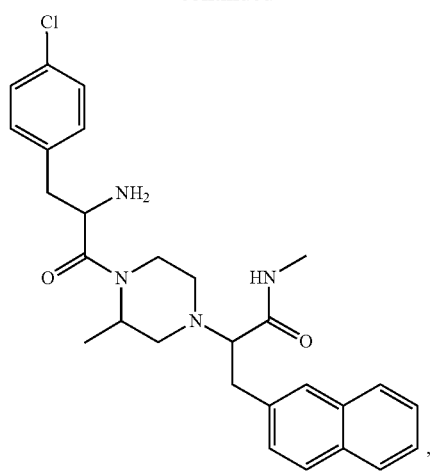
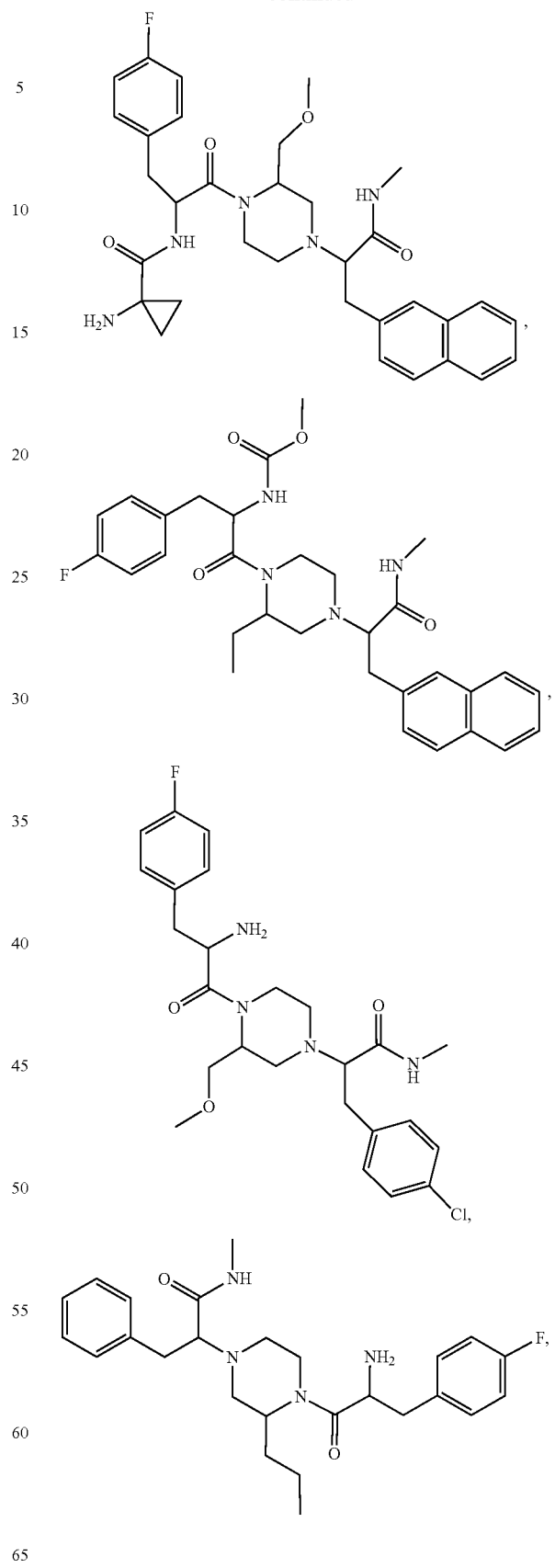

59
-continued
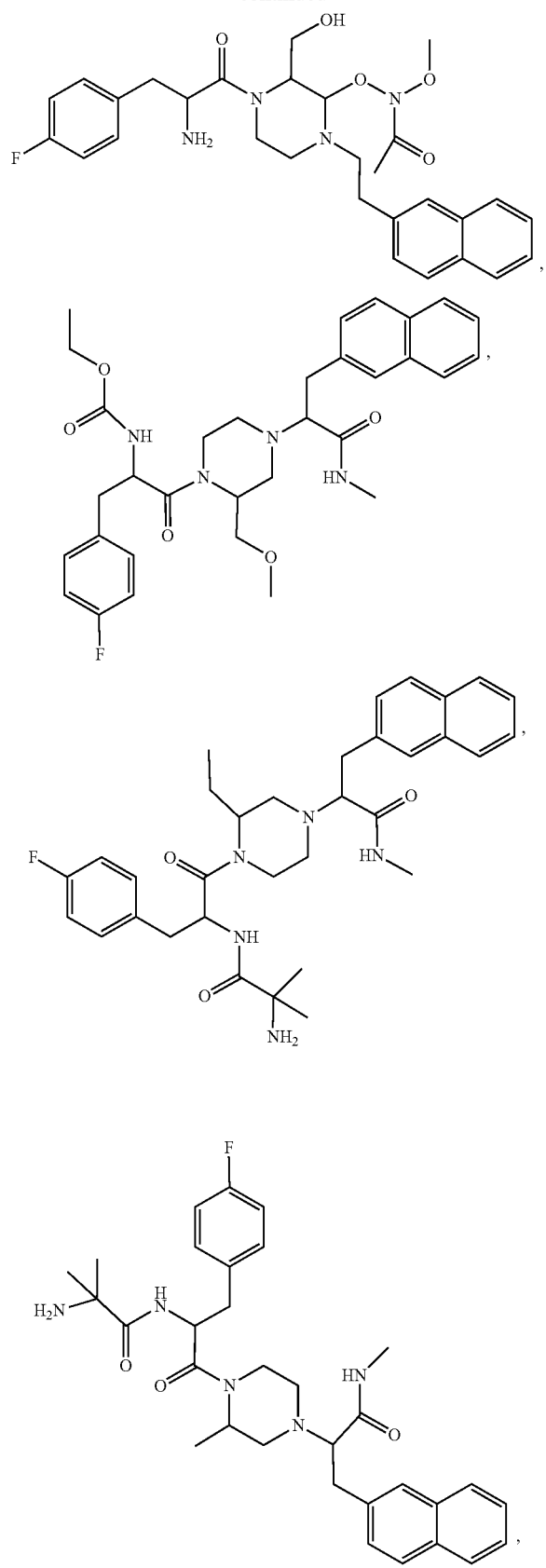
60
-continued
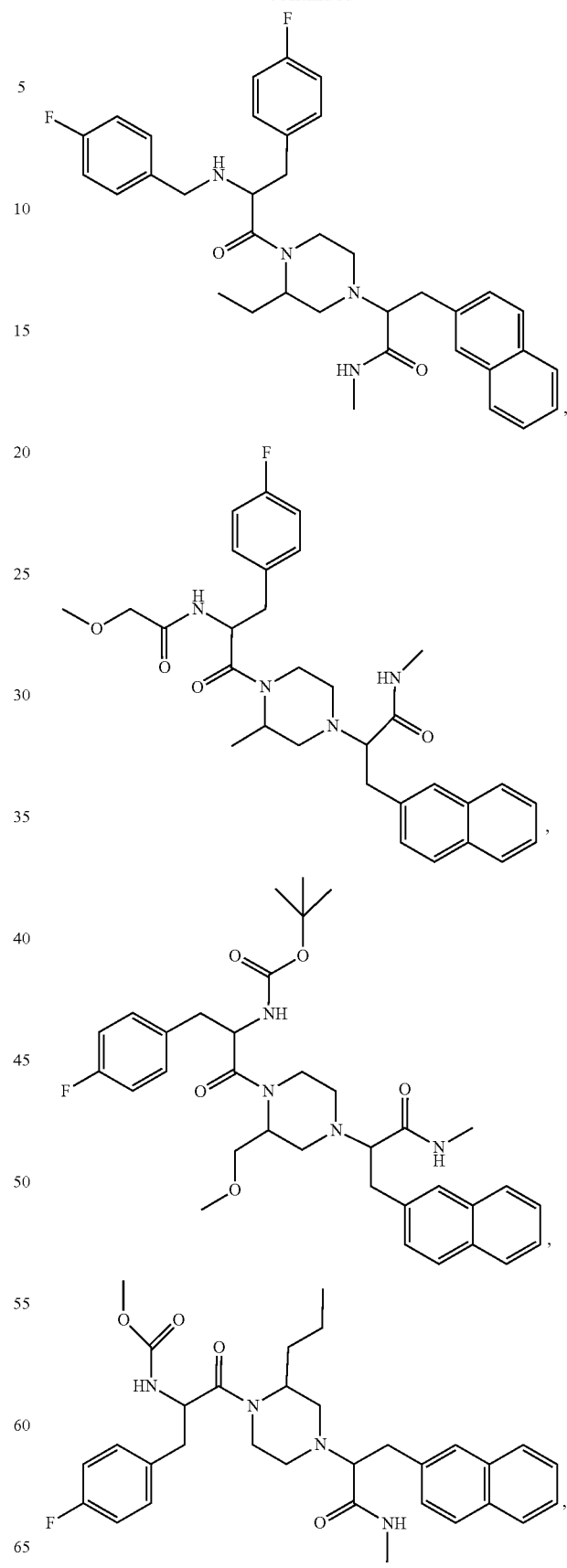

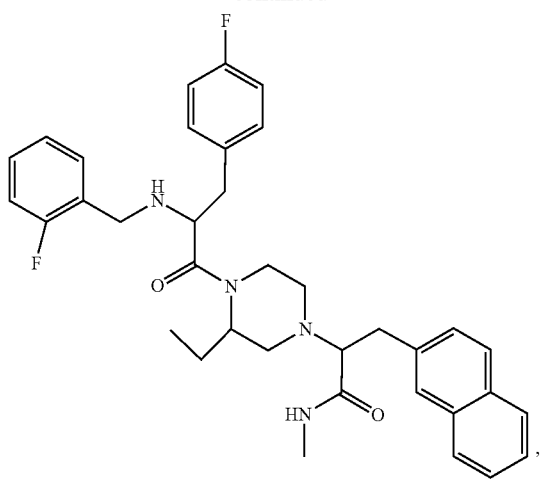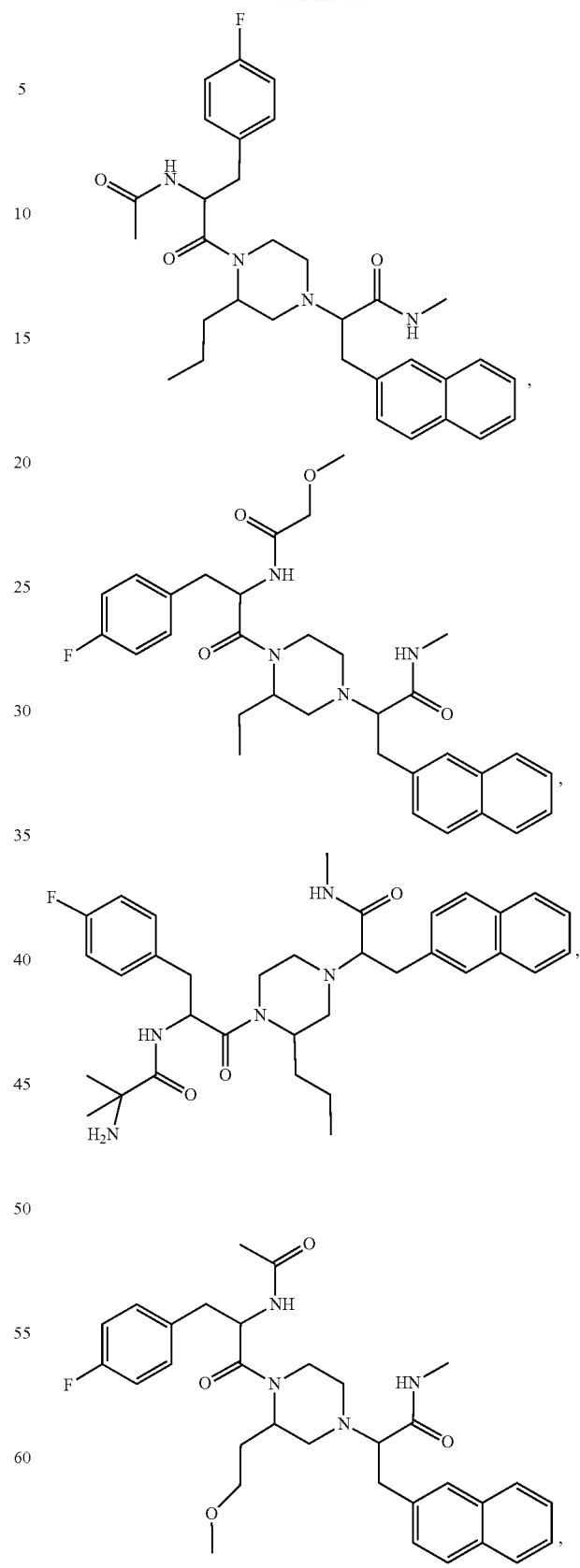

63
-continued
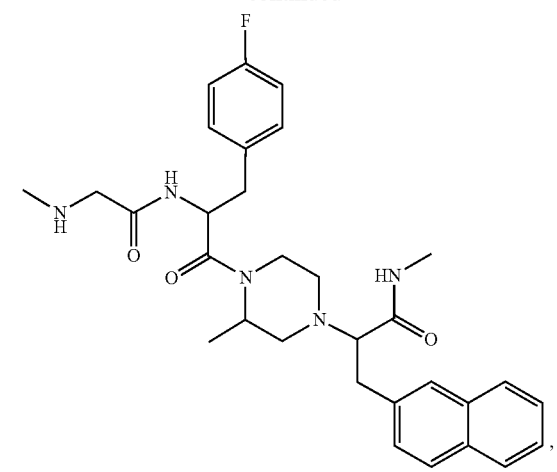
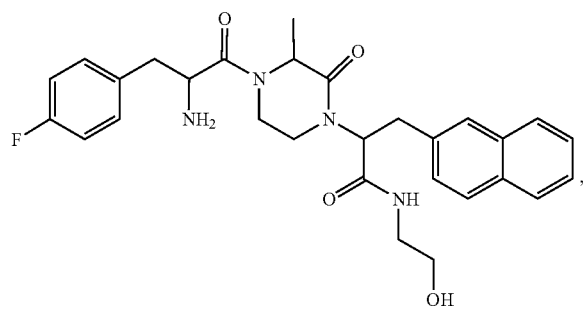
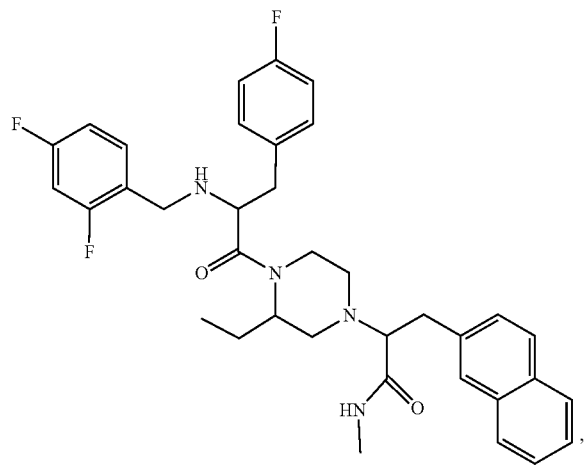
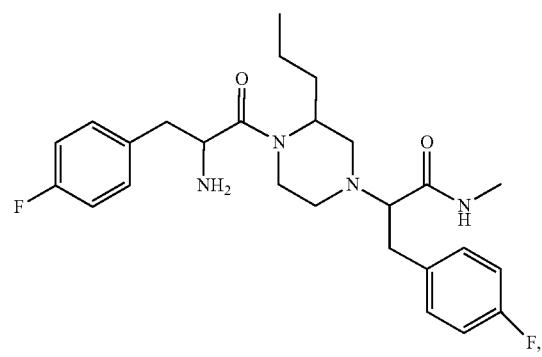
64
-continued
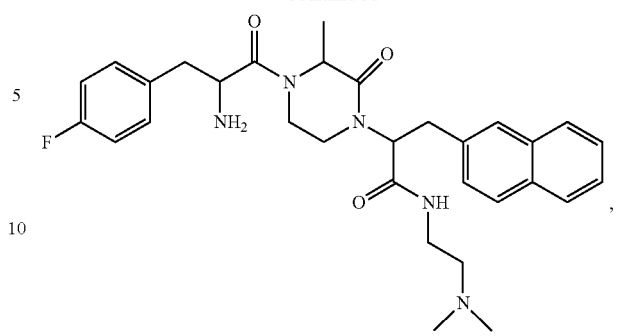
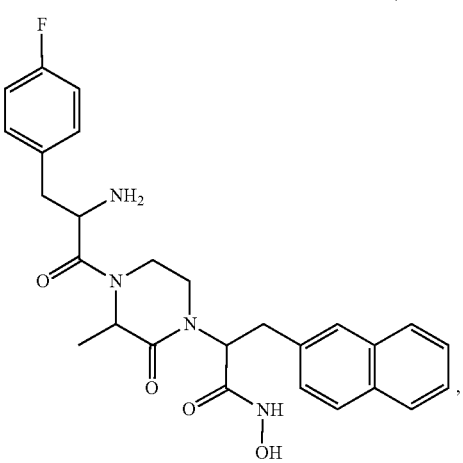
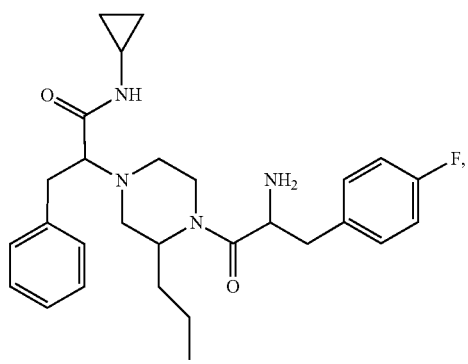
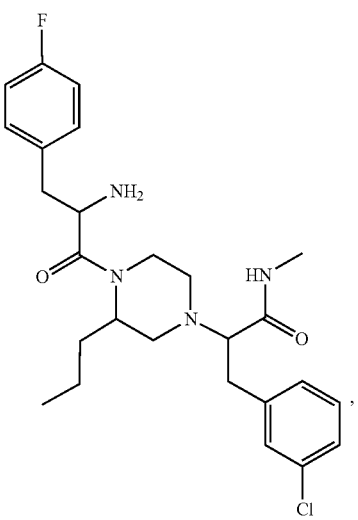

-continued

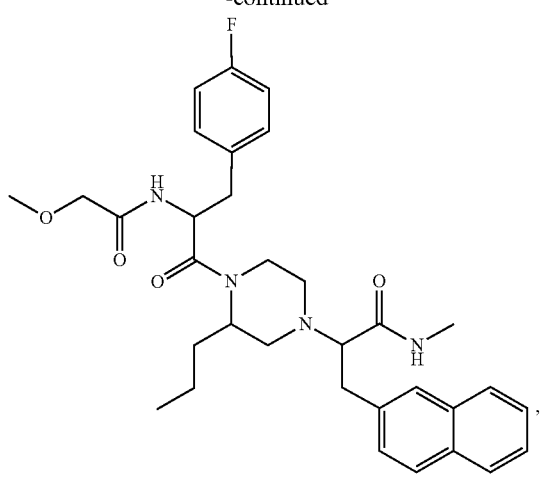

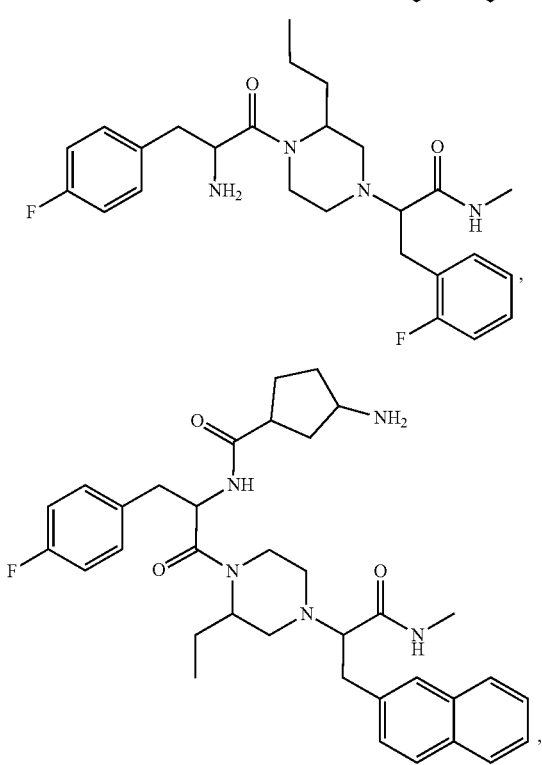

-continued

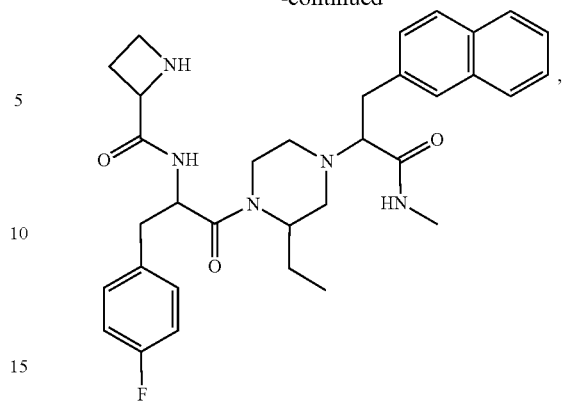

and pharmaceutically acceptable salts thereof.

7. The method of claim 1, the compound comprising the formula:

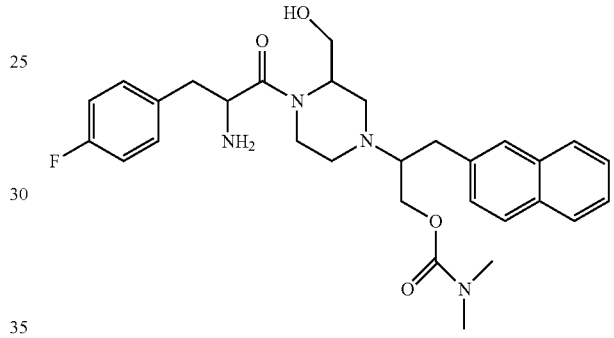

and pharmaceutically acceptable salts thereof.

8. The method of claim 1, wherein the Bcl-2 associated cancer is selected from the group consisting of chronic lymphocytic leukemia (CLL), follicular lymphoma, diffuse large B-cell lymphoma, and multiple myeloma (MM).

9. The method of claim 3, the second agent comprising at least one of a chromene, a thiazolidine, a benzensulfony, a benzenesulfonamide, an antimycin, a dibenzodiazocine, a terphenyl, an indole, gossypol, an apogossypol, an epigallocatechingallate, or a theaflavanin.

10. The method of claim 3, the second agent comprising at least one of N-(4-(4-(4'-chloro-biphenyl-2-ylmethyl)-piperazin-1-yl)-bezoyl)-4-(3-dimethylamino-1-phenylsulfanyl-methyl-propylamino)-3-nitro-benzenesulfonamide, ABT-737, ABT-263, or ABT-199.

* * * * *